( 12 ) United States Patent
Chou

(10) Patent No.: US 7,258,974 B2
(45) Date of Patent: Aug. 21, 2007

(54) TRANSCRIPTION FACTOR NETWORK DISCOVERY METHODS

(75) Inventor: Michael F. Chou, 205 Third Ave., Apt. 11N, New York, NY (US) 10003

(73) Assignee: Michael F. Chou, Brookline, MA (US)

( * ) Notice: Subject to any disclaimer, the term of this patent is extended or adjusted under 35 U.S.C. 154(b) by 236 days.

(21) Appl. No.: 10/128,652

(22) Filed: Apr. 23, 2002

(65) Prior Publication Data

US 2004/0053227 A1    Mar. 18, 2004

Related U.S. Application Data

(60) Provisional application No. 60/285,716, filed on Apr. 23, 2001.

(51) Int. Cl.
*C12Q 1/68* (2006.01)

(52) U.S. Cl. .................... 435/6; 435/287.1; 435/287.2

(58) Field of Classification Search ................... 435/6, 435/7.1, 69.1, 7.31; 536/25.3, 23.1
See application file for complete search history.

(56) References Cited

U.S. PATENT DOCUMENTS

| 5,143,854 | A | | 9/1992 | Pirrung et al. |
| 5,556,752 | A | | 9/1996 | Lockhart et al. |
| 5,770,722 | A | * | 6/1998 | Lockhart et al. ........... 536/25.3 |
| 5,800,992 | A | | 9/1998 | Fodor et al. |
| 6,165,709 | A | * | 12/2000 | Friend et al. ................... 435/4 |
| 6,582,908 | B2 | * | 6/2003 | Fodor et al. ................... 435/6 |

OTHER PUBLICATIONS

Larry Gold et al., Annu. Rev. Biochem., 64:763-797 (1995).
Martin Tompa et al., Nature Biotechnology, 23:137-144 (2005).
E. Wingender et al., Nucleic Acids Research, 24:238-241 (1996).
Pennacchio et al., Genomic Strategies To Identify Mammalian Regulatory Sequences, Nature Reviews/Genetics, 2:100-109 (2001).
Wasserman et al., Applied Bioinformatics For The Identification Of Regulatory Elements, Nature Reviews/Genetics, 5:276-287 (2004).

* cited by examiner

*Primary Examiner*—Teresa E. Strzelecka
*Assistant Examiner*—Heather G. Calamita
(74) *Attorney, Agent, or Firm*—Klauber & Jackson

(57) ABSTRACT

The invention is a new method to analyze nucleic acid-protein binding data in a systematic or statistical manner in order to determine the DNA binding regions for proteins which bind to DNA and are usually involved in the regulation of the expression of genes, and may enhance, promote or repress the expression of the gene.

22 Claims, 22 Drawing Sheets

| Mapping of TFs to Genes with matching regulatory regions | | Gene expression analysis results by classical microarray or other assay | Preliminary interpretation |
|---|---|---|---|
| TF A | gene a | Expressed | TFA enhances expression of *gene a* |
| | gene b | Not Expressed | *gene b* not affected by TFA or TFB |
| | gene c | Expressed | *gene c* is constitutively expressed or affected by some other TF's |
| TF B | gene d | Not Expressed | TFA or TFB may be repressing the expression of *gene d* |
| | gene e | Not Expressed | *gene e* not affected by TFA or TFB |
| | gene f | Expressed | expression of *gene f* is enhanced by TFB |
| | gene g | Not Expressed | *gene g* is repressed by TFB |

Figure 10

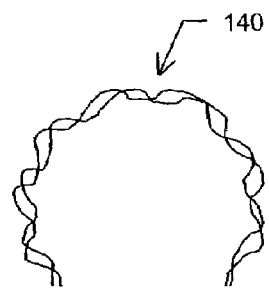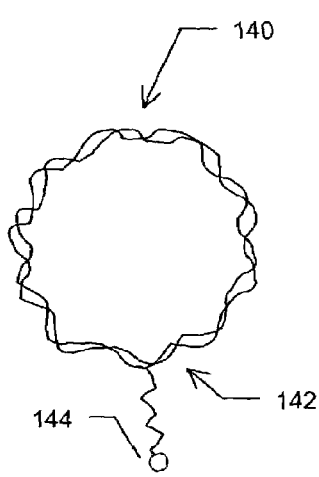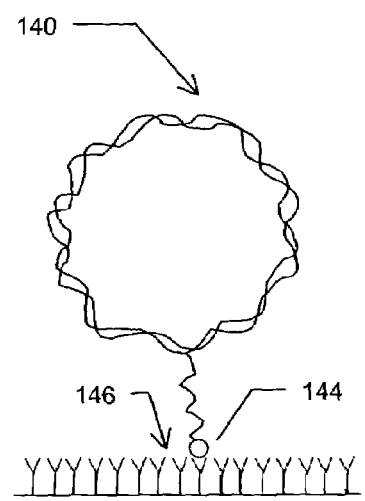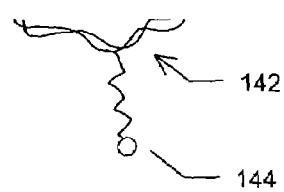
Figure 12A  Figure 12B  Figure 12C
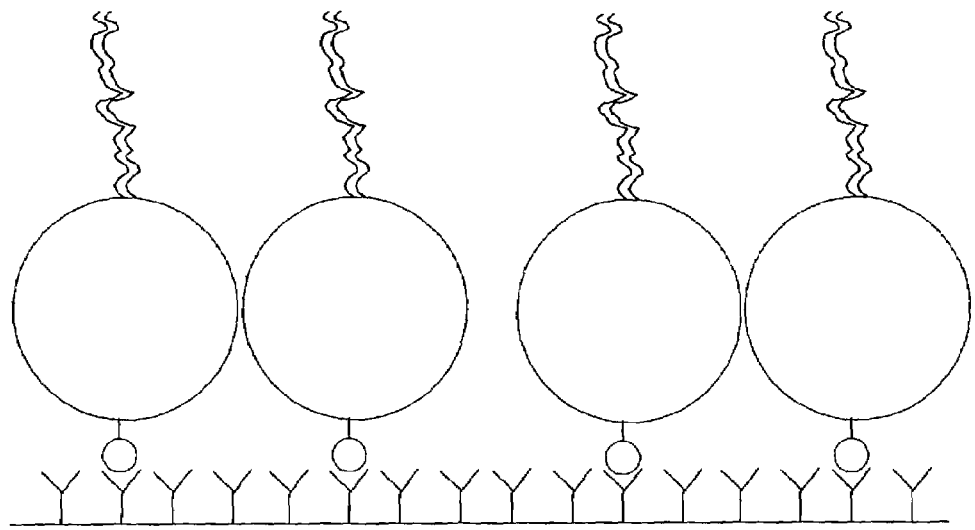
Figure 13

Step 1
Generate physical probes using combinatorial chemistry methods to generate probes of a certain minimal length with or without random sequences. (e.g. using phosporamidite synthesis, all probes with a constant primer region plus substantially all random sequences of length 10 followed by another constant region. Use a constant region to generate dsDNA using primers complementary to one or more constant regions, DNA polymerase and dNTPs.) (160)

Step 2
Perform probe binding assay (i.e. Incubate with solution containing potential probe targets such as purified proteins, cell lysate or other molecules such as drug candidates) (162)

Step 3
1. Read probes bound (e.g. fluorescence, competitive binding)
2. Determine probe sequences (If probes were generated on uniquely tagged beads, then read the tag, and determine the probe sequence. If probes were free in solution, then sequence bound probes using iterative Sanger sequencing (described herein) or other traditional method such as plasmid transfection followed by colony sequencing. (164)

Step 4
List of all possible probe sequences (from Step 1) with bound and unbound status of each the original probes (with optional binding affinity). This is the 'Gross Binding Site Output'. (166)

Figure 15

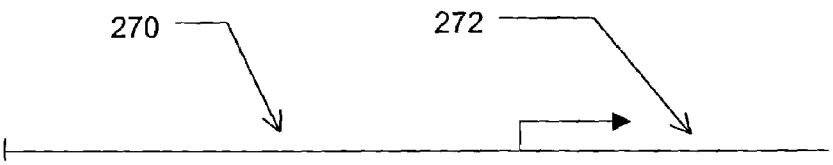
Figure 22A
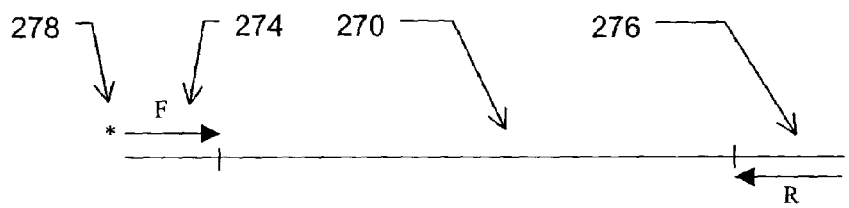
Figure 22B
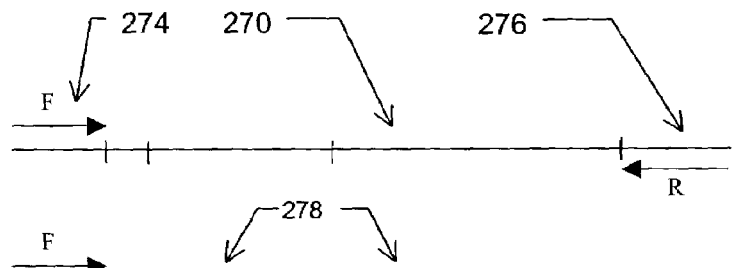
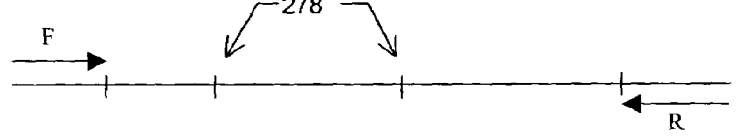
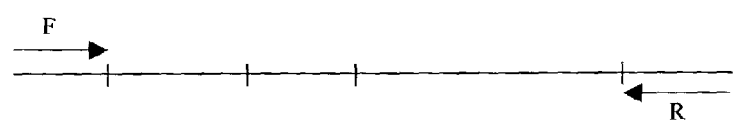
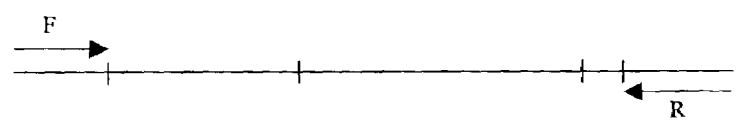
Figure 22C

SEQUENCE LISTING

<160> NUMBER OF SEQ ID NOS: 29

<210> SEQ ID NO 1
<211> LENGTH: 33
<212> TYPE: DNA
<213> ORGANISM: Artificial Sequence
<220> FEATURE:
<223> OTHER INFORMATION: Hypothetical Sequence

<400> SEQUENCE: 1
atctgctcgc tgctgggtct agcttagcta gct                                    33

<210> SEQ ID NO 2
<211> LENGTH: 33
<212> TYPE: DNA
<213> ORGANISM: Artificial Sequence
<220> FEATURE:
<223> OTHER INFORMATION: Hypothetical Sequence

<400> SEQUENCE: 2
atctgcgcgc tgctgggact agcttagcta gct                                    33

<210> SEQ ID NO 3
<211> LENGTH: 33
<212> TYPE: DNA
<213> ORGANISM: Artificial Sequence
<220> FEATURE:
<223> OTHER INFORMATION: Hypothetical Sequence

<400> SEQUENCE: 3
atctgctcgg tgctgggtct agcttagcta gct                                    33

<210> SEQ ID NO 4
<211> LENGTH: 33
<212> TYPE: DNA
<213> ORGANISM: Artificial Sequence
<220> FEATURE:
<223> OTHER INFORMATION: Hypothetical Sequence

<400> SEQUENCE: 4
atctgctcgc tgctgggtct agcttagcta gct                                    33

<210> SEQ ID NO 5
<211> LENGTH: 33
<212> TYPE: DNA
<213> ORGANISM: Artificial Sequence
<220> FEATURE:
<223> OTHER INFORMATION: Hypothetical Sequence

<400> SEQUENCE: 5
atctgctcgc tgctgggtct agcttagcta gct                                    33

<210> SEQ ID NO 6
<211> LENGTH: 31
<212> TYPE: DNA
<213> ORGANISM: Artificial Sequence
<220> FEATURE:
<223> OTHER INFORMATION: Hypothetical Sequence

<400> SEQUENCE: 6
ctgctcgctg ctgggtctag cttagctagc t                                      31

<210> SEQ ID NO 7
<211> LENGTH: 31

<212> TYPE: DNA
<213> ORGANISM: Artificial Sequence
<220> FEATURE:
<223> OTHER INFORMATION: Hypothetical Sequence

<400> SEQUENCE: 7
ctgctcgctg ctgggtctag cttagctagc t                                31

<210> SEQ ID NO 8
<211> LENGTH: 31
<212> TYPE: DNA
<213> ORGANISM: Artificial Sequence
<220> FEATURE:
<223> OTHER INFORMATION: Hypothetical Sequence

<400> SEQUENCE: 8
ctgcgcgctg ctgggactag cttagctagc t                                31

<210> SEQ ID NO 9
<211> LENGTH: 28
<212> TYPE: DNA
<213> ORGANISM: Artificial Sequence
<220> FEATURE:
<223> OTHER INFORMATION: Hypothetical Sequence

<400> SEQUENCE: 9
ctcgctgctg ggtctagctt agctagct                                    28

<210> SEQ ID NO 10
<211> LENGTH: 28
<212> TYPE: DNA
<213> ORGANISM: Artificial Sequence
<220> FEATURE:
<223> OTHER INFORMATION: Hypotheticall Sequence

<400> SEQUENCE: 10
ctcggtgctg ggtctagctt agctagct                                    28

<210> SEQ ID NO 11
<211> LENGTH: 33
<212> TYPE: DNA
<213> ORGANISM: Artificial Sequence
<220> FEATURE:
<223> OTHER INFORMATION: Hypothetical Sequence
<220> FEATURE:
<221> NAME/KEY: misc_feature
<222> LOCATION: (7)...(7)
<223> OTHER INFORMATION: n represents a,t,c,g
<220> FEATURE:
<221> NAME/KEY: misc_feature
<222> LOCATION: (10)...(10)
<223> OTHER INFORMATION: n represents a,t,c,g
<220> FEATURE:
<221> NAME/KEY: misc_feature
<222> LOCATION: (18)...(18)
<223> OTHER INFORMATION: n represents a,t,c,g

<400> SEQUENCE: 11
atctgcncgn tgctgggnct agcttagcta gct                              33

<210> SEQ ID NO 12
<211> LENGTH: 31
<212> TYPE: DNA
<213> ORGANISM: Artificial Sequence
<220> FEATURE:
<223> OTHER INFORMATION: Hypothetical Sequence
<220> FEATURE:
<221> NAME/KEY: misc_feature
<222> LOCATION: (8)...(8)

<223> OTHER INFORMATION: n represents a,t,c,g

<400> SEQUENCE: 12
ctgctcgntg ctgggtctag cttagctagc t     31

<210> SEQ ID NO 13
<211> LENGTH: 28
<212> TYPE: DNA
<213> ORGANISM: Artificial Sequence
<220> FEATURE:
<223> OTHER INFORMATION: Hypothetical Sequence

<400> SEQUENCE: 13
ctcgctgctg ggtctagctt agctagct     28

<210> SEQ ID NO 14
<211> LENGTH: 28
<212> TYPE: DNA
<213> ORGANISM: Artificial Sequence
<220> FEATURE:
<223> OTHER INFORMATION: Hypothetical  Sequence

<400> SEQUENCE: 14
ctcggtgctg ggtctagctt agctagct     28

<210> SEQ ID NO 15
<211> LENGTH: 31
<212> TYPE: DNA
<213> ORGANISM: Artificial Sequence
<220> FEATURE:
<223> OTHER INFORMATION: Hypothetical  Sequence

<400> SEQUENCE: 15
ctgcgcgctg ctgggactag cttagctagc t     31

<210> SEQ ID NO 16
<211> LENGTH: 28
<212> TYPE: DNA
<213> ORGANISM: Artificial Sequence
<220> FEATURE:
<223> OTHER INFORMATION: Hypothetical Sequence

<400> SEQUENCE: 16
ctcgctgctg ggtctagctt agctagct     28

<210> SEQ ID NO 17
<211> LENGTH: 28
<212> TYPE: DNA
<213> ORGANISM: Artificial Sequence
<220> FEATURE:
<223> OTHER INFORMATION: Hypothetical Sequence

<400> SEQUENCE: 17
ctcggtgctg ggtctagctt agctagct     28

<210> SEQ ID NO 18
<211> LENGTH: 31
<212> TYPE: DNA
<213> ORGANISM: Artificial Sequence
<220> FEATURE:
<223> OTHER INFORMATION: Hypothetical Sequence

<400> SEQUENCE: 18
ctgcgcgctg ctgggactag cttagctagc t     31

```
<210> SEQ ID NO 19
<211> LENGTH: 33
<212> TYPE: DNA
<213> ORGANISM: Artificial Sequence
<220> FEATURE:
<223> OTHER INFORMATION: Hypothetical Sequence

<400> SEQUENCE: 19
atctgctcgc tgctgggtct agcttagcta gct                                    33

<210> SEQ ID NO 20
<211> LENGTH: 33
<212> TYPE: DNA
<213> ORGANISM: Artificial Sequence
<220> FEATURE:
<223> OTHER INFORMATION: Hypothetical Sequence

<400> SEQUENCE: 20
atctgcgcgc tgctgggact agcttagcta gct                                    33

<210> SEQ ID NO 21
<211> LENGTH: 33
<212> TYPE: DNA
<213> ORGANISM: Artificial Sequence
<220> FEATURE:
<223> OTHER INFORMATION: Hypothetical Sequence

<400> SEQUENCE: 21
atctgctcgg tgctgggtct agcttagcta gct                                    33

<210> SEQ ID NO 22
<211> LENGTH: 24
<212> TYPE: DNA
<213> ORGANISM: Artificial Sequence
<220> FEATURE:
<223> OTHER INFORMATION: Hypothetical Sequence

<400> SEQUENCE: 22
atctgctagg ctcgattata gctt                                              24

<210> SEQ ID NO 23
<211> LENGTH: 38
<212> TYPE: DNA
<213> ORGANISM: Artificial Sequence
<220> FEATURE:
<223> OTHER INFORMATION: Hypothetical Sequence

<400> SEQUENCE: 23
gctagcgatc agcatatcag actagctagc atacgcat                               38

<210> SEQ ID NO 24
<211> LENGTH: 24
<212> TYPE: DNA
<213> ORGANISM: Artificial Sequence
<220> FEATURE:
<223> OTHER INFORMATION: Hypothetical Sequence

<400> SEQUENCE: 24
atctcagatc aggctcgatt gcaa                                              24

<210> SEQ ID NO 25
<211> LENGTH: 38
<212> TYPE: DNA
<213> ORGANISM: Artificial Sequence
<220> FEATURE:
<223> OTHER INFORMATION: Hypothetical Sequence
```

-continued

```
<400> SEQUENCE: 25
ugucgaucua gucguauagu cugaucgauc guaugcgu                           38

<210> SEQ ID NO 26
<211> LENGTH: 37
<212> TYPE: DNA
<213> ORGANISM: Artificial Sequence
<220> FEATURE:
<223> OTHER INFORMATION: Hypothetical Sequence

<400> SEQUENCE: 26
gtcaggcagg cagctcagcg atcagcatca gcatgca                            37

<210> SEQ ID NO 27
<211> LENGTH: 24
<212> TYPE: DNA
<213> ORGANISM: Artificial Sequence
<220> FEATURE:
<223> OTHER INFORMATION: Hypothetical Sequence

<400> SEQUENCE: 27
accaggctcg attcatgcag gcga                                          24

<210> SEQ ID NO 28
<211> LENGTH: 37
<212> TYPE: DNA
<213> ORGANISM: Artificial Sequence
<220> FEATURE:
<223> OTHER INFORMATION: Hypothetical Sequence

<400> SEQUENCE: 28
gcgctatcag cacatgcatc agcatgcatc atcgatc                            37

<210> SEQ ID NO 29
<211> LENGTH: 65
<212> TYPE: DNA
<213> ORGANISM: Artificial Sequence
<220> FEATURE:
<223> OTHER INFORMATION: Hypothetical Sequence

<400> SEQUENCE: 29
atctgctagg ctcgattata gcttattaca gctagatcag catatcagac tagctagcat   60
acgca                                                               65
```

TRANSCRIPTION FACTOR NETWORK DISCOVERY METHODS

This application claims priority of U.S. provisional application 60/285,716 filed Apr. 23, 2001, which is incorporated by reference in its entirety.

BACKGROUND OF THE INVENTION

1. Field of the Invention

This invention falls within the general areas of bioinformatics, microarray analysis and DNA-protein binding assays.

2. Description of Related Art

It is known that all cells have genes that are basically on all of the time and others that are inducible or repressible via a number of mechanisms. Virtually all known mechanisms for gene regulation depend upon proteins known as transcription factors that attach to specific sequences of DNA in a region of the gene on the genome. Once these factors are attached to the DNA, they aid the cell in expressing the gene they are near. These regions of DNA are called regulatory regions. The most commonly referenced regulatory region is called a promoter because its existence in the presence of transcription factors promotes expression of the gene.

While some commonly occurring regulatory sequences have been identified (such as the well known TATA box and others), in general, promoter regions for a given gene are difficult to determine.

Since transcription factors are themselves proteins, at some point, they were also the result of gene expression. (Transcription factors can also undergo changes after they are synthesized by the cell—sometimes in response to factors external to the cell. Sometimes the transcription factor is initially inert, and it is the result of these changes which makes the transcription factor active.) In general, genes can form regulatory networks with one gene's protein product acting as a transcription factor for another gene that then acts as a transcription factor for another one, etc. Transcription factors may also act on more than one other gene, and may act to positively or negatively regulate genes that they are near (usually downstream). Finally, transcription factors frequently operate only when bound to other identical or different transcription factors—that is, it may take several transcription factors (which may be the result of different activation events) to turn on or off the expression of a gene.

It is the discovery and understanding of these networks and other control mechanisms of the cell that allows us to rationally design drugs, and to understand how diseased cells differ from normal cells.

To gain a deeper understanding of cellular mechanisms researchers are trying to measure which of the genes of a given cell are activated. Current efforts using micro-array technology attempt to measure mRNA expression level in cells by hybridization with thousands of different DNA probes—each probe is specifically created to match a specific mRNA transcript from a living cell prior to analysis. Since mRNA is much more uniform than the folded protein products (the result of translation), it is much easier to estimate protein expression by measuring mRNA levels than by trying to measure the resulting protein levels.

While this is an incredibly powerful technique, no one experimental method can tell the whole story, and in this case while we can finally see the fact that different cells express mRNA (and consequently proteins) in different quantities and at different times, we still can't see exactly why. In other words, we must still search for causality. In many cases, an experimental condition will trigger a different pattern of mRNA expression, but cells are so complicated, that it is rarely limited to one new gene expressed based on the new conditions. More likely, there is experimental noise that interferes with an already complex response to the stimulus—many genes are frequently expressed in response to even simple stimuli.

While we know that transcription factors are the intermediaries in the process of gene expression, we can't directly tell which ones are responsible for the observed expression pattern. In other words, we still can't get very precise cause and effect data for each gene which would allow us to build up a network of interactions between one transcription factor and genes expressed.

Many bioinformatic approaches are being taken to try and guess what the promoter sequences are for a given set of genes. The premise of these methods is that if we can find regulatory DNA sequences in common between several expressed genes. We can then try and deduce the transcription factors. Suppose that three hypothetical genes shown in FIG. 11B are all found to be expressed under the same conditions. Their genomic DNA (including the regulatory and the expressed regions of the genes) shows that the region marked "promoter region" (120) is the same in all three genes.

Such a determination may have been made, for example, by a bioinformatic computer program which searched for this particular sequence, or for sequences in common. This determination requires knowing the DNA sequence around the expressed region of the gene so that such analysis can be performed. Many organisms that are subjected to microarray analysis have full genome sequences available (yeast, Arabidopsis, fruit fly, etc.), however, this is far from a solved problem. While the above example may have been solvable by eye, reality is never this simple. For the following reasons among others:

- Regulatory sequences can be thousands of bases long, and the problem of determining a common sequence (consensus sequence) may not be unique.
- Genes that are expressed together may share a transcription factor, but they may not. More importantly, there are so many genes being expressed in a cell at any given time, even if we have a snapshot of these genes, it is not clear which ones are related—there are literally thousands of genes expressed at any given time in some cells—all of which might be related.
- Those genes that are not expressed might also be related but some other transcription factor acting in a repressive manner could be counteracting the effects of the transcription factor that would otherwise help to promote the expression.
- Genes are expressed by a complicated set of transcription factors—sometimes in an all-or-nothing kind of relationship. It is virtually impossible to reliably determine all of the factors especially when you don't know the a priori relationship. (see Arnone and Davidson, Development 124:151-1864)
- Many promoter sequences can vary slightly by one or more bases and still be identified by the same transcription factor—making the similarity determination much more complicated than the above example.
- We are not just trying to determine the transcription factors, we are trying to determine the relationship between the transcription factors as well. Either one would be easier to determine if the other was known.

Deducing a transcription factor from a regulatory sequence is probably an even more difficult problem than finding a consensus sequence. Even if you have the crystal structure of the transcription factor you are looking for (a costly and time consuming endeavor which isn't performed for all proteins), knowing the DNA sequence that it binds to is difficult to determine. This is like trying to tell what a key looks like by looking at a lock—while it is possible, it is still very difficult.

Current experimental methods use a method known as footprint analysis to determine the interaction between transcription factors and particular DNA sequences (see Ausubel, et al. (eds.) Short Protocols in Molecular Biology (John Wiley & Sons 1999)). This is also slow, tedious, and generally focuses on only one factor at a given time. It also requires significantly narrowing the sequence a priori and is therefore useful more as a hypothesis confirmation method than as a discovery method.

Microarray analyzers are commercially available now, and are covered by many existing patents, and public knowledge in the scientific literature (for example Shalon et al. 1996 Genome Res. 6:639-45, Schena et al. 1995 Science 270:467-470, and U.S. Pat. No. 5,143,854). DNA-protein binding detection assays using radioactive and fluorescent labeling are available as common molecular biology techniques, and are also widely described in the literature.

Practitioners of the instant invention will, generally, have an advanced degree in one or more disciplines including, but not limited to: molecular biology, biochemistry, biomathematics, bioinformatics, biostatistics, genetics, genetic engineering, computer science etc. Alternately, a practitioner will have an advanced science or engineering discipline related to the design, construction, or utilization of, or interpreting results from, systems or devices (or programming of the control software further comprising such devices or systems) utilized in such disciplines, including but not limited to: gene sequencers, microarray analyzers, and the like.

It is within the ken of those skilled in the art to design, construct, utilize, interpret results from, systems or devices (or programming of the control software further comprising such devices or systems) utilized in practicing the instant invention.

Rather than repeat details of that which known in the art, the instant application will focus on the novel arrangements and combinations of known processes and devices, and the wholly novel processes and devices, employed to practice the instant invention.

SUMMARY OF THE INVENTION

Most microarrays are used to detect mRNA expression levels. Such arrays use single stranded DNA to hybridize with single-stranded cDNA or mRNA. The arrays in this invention, on the other hand, use double-stranded DNA (dsDNA) as 'bait' to detect protein binding. Specifically, double-stranded microarrays and other probes are used in their native (non-denatured) form as targets for transcription factor/repressor proteins (hereinafter just 'transcription factors' to mean both). While dsDNA/protein-binding assays are not necessarily new, it isn't commercially being used in a microarray format (see U.S. Pat. No. 5,556,752 and Bulyk, et al. 1999 Nature Biotechnology 17:573-577). However, the real power of this idea is the use of a systematic set of DNA sequences as a screening mechanism. This is not a library of sequences, but rather an exhaustive set of all possible short oligo-nucleotides of a certain length. Because we are trying to find transcription factors, the length of the oligo can be rather short (at least the recognition sequence can be short—the actual oligo could have some spacer DNA on either side of the potential binding site.) So, for example, if we want to make an array of all possible 6 bp DNA sequences, there are exactly 4096 different sequences which represent all possibilities, and these may be easily arrayed on a chip.

Exposure of putative transcription factors to a microarray of all such possibilities will result in the specific binding of the transcription factors to one or more sites. If the transcription factor binds to one specific site, then we can use that sequence to find genes with regulatory regions that contain that particular sequence. This can be done using a bioinformatics approach using database searching, or using molecular biology approaches such as PCR amplification.

From a bioinformatics perspective, the real power comes in being able to decipher more complicated binding patterns. In particular, with longer oligos (say 7-10 bp sequences), a given transcription factor may bind to many sites, which in a single assay, can tell us which part of the sequence is required for binding, and which bases are not important. Again, such information can be used to search through the genomic DNA, for example by PCR or a database search (in vivo or in silico—if the genome has been fully sequenced which, now, many have), and then potential target genes may be identified.

One of the main benefits of this method is that it is a FORWARD, not a reverse model. That is, normally, even if we find genes that are co-expressed in a standard microarray experiment, it gives very limited ability to find causality—such as which transcription factor(s) are responsible for the expression of these genes (a REVERSE search in effect). On the other hand, this method gives a set of candidate genes in the forward direction. In fact, for a given transcription factor, only genes with the identified binding sequence in their regulatory regions can be expressed (or repressed) by the transcription factor (or repressor). In fact, this method should be able to reliably go in reverse to find a repressor.

Importantly, this is ideally suited to a genomic approach. Actually, the simultaneous analysis of mRNA transcription levels and this forward transcription factor/DNA-binding assay can yield hundreds of regulatory pathways—and easily flesh-out the entire regulatory network of a sequenced organism with a small number of microarray experiments. Understanding of such regulatory networks can lead to obvious immediate benefits in understanding disease, treatment and drug design.

It should be noted, that while the microarray format has some appeal in terms of ease of use and understanding, there are other alternative approaches which are non-microarray specific that may instead be used to obtain the raw data needed to perform the data analysis described above (See FIGS. 1 and 2). This invention does not, therefore, necessarily depend on the microarray field.

This invention exploits the experimental observation that an active transcription factor(s) which binds to a regulatory region and the expression (or repression) of a neighboring gene can be connected through the known or discoverable genomic sequence of the organism.

The invention uses diverse oligonucleotide sequences as an assay to probe for target molecules that bind to the probes. In one embodiment of the assay, the invention provides arrays of spatially restricted probes. In another embodiment, the probes are attached to a bead that overcomes some of the limitations of a two-dimensional binding surface while allowing pseudo-solution phase interactions with targets. In yet another embodiment, the probes are free to move about in solution.

Accordingly, this invention is directed to an array of nucleic acid probes attached directly or indirectly to a solid support. The probes are constructed to minimize binding interference between a first DNA-binding protein and a first probe of said array caused by one or more elements which would otherwise hinder the binding of the first DNA-binding protein to the first probe of said array, when the array is exposed to a population of DNA-binding proteins. The probes may be single-stranded nucleic acid probes or double-stranded nucleic acid probes. Thus, interference caused by any element present in the environment of the array which would hinder the binding of any one or more given DNA-binding proteins to any one or more probes on the array is minimized by the construction of the probes themselves. Elements can include a second probe of the array, a second DNA-binding protein, or the solid support itself.

In one array of this invention, binding interference is minimized because at least one of the probes in the array, or any number of probes up to the total number of probes, is a closed circular loop of nucleic acid which comprises two opposite sides, the first side of the loop containing a binding site for a DNA-binding protein and the second side of the loop containing an attachment site to a linker molecule which is itself attached to the solid support, by which attachment site the second side of the loop is attached to the solid support (by the linker molecule). The probes may be single-stranded nucleic acid probes or double-stranded nucleic acid probes.

In another array of this invention, binding interference is minimized because at least one probe is attached to the solid support by a molecular spacing structure which is bound to both the probe and to the solid support such that the binding of a DNA-binding protein to the probe is not impeded and the probe is packed less closely to neighboring probes in the array.

This invention is also directed to a method for producing any of the arrays of this invention, for example an array of nucleic acid probes attached directly or indirectly to a solid support where the probes are constructed to minimize binding interference between a first DNA-binding protein and a first probe of said array caused by one or more elements which would otherwise hinder the binding of the first DNA-binding protein to the first probe of said array, when the array is exposed to a population of DNA-binding proteins. The probes may be single-stranded nucleic acid probes or double-stranded nucleic acid probes.

Also part of this invention is a method for binding a DNA-binding protein to a nucleic acid probe in an array of nucleic acid probes attached directly or indirectly to a solid support where binding interference between the DNA-binding protein and the probe caused by one or more elements which would otherwise hinder their binding when the array is exposed to a population of DNA-binding proteins, is minimized because of the manner in which the probes are constructed. The probes may be single-stranded nucleic acid probes or double-stranded nucleic acid probes.

Also part of this invention is a method for determining the nucleic acid sequence specificity of a DNA-binding protein by (a) providing a plurality of double-stranded nucleic acid probes which represent substantially all combinations of sequences of N base pairs in length, which may be in solution or in an immobilized state on a solid support, (b) contacting the double-stranded nucleic acid probes with a DNA-binding protein under conditions such that the DNA-binding protein binds to one or more specific double-stranded nucleic acid probes of the plurality of double-stranded nucleic acid probes provided in step (a); and (c) determining the sequences of the specific double-stranded nucleic acid sequence to which the DNA-binding protein has bound in step (b); thus determining the nucleic acid sequence specificity of the DNA-binding protein.

Also part of this invention are analysis methods, which can be used to analyze the sequence information regarding nucleic acid probes bound by DNA-binding proteins obtained by assays of this invention, to elucidate further information such as natural binding sites for such proteins.

Accordingly, part of this invention is a method for determining a set of potential double-stranded DNA binding site sequences equal to or less than a probe length L, of a protein, for example a DNA-binding protein, which has been exposed to a set of nucleic acid probes P, and has bound to subset B of said set P wherein, for each possible nucleotide sequence Ti of non-zero length and shorter or equal to length L, the following steps are performed: (a) comparing said sequence Ti to the sequence of each member Pj of set P and, if Ti is a subsequence of the sequence of Pj; then, (b) adding Pj to a set Hi of hypothetical probes corresponding to sequence Ti, and if Hi is a subset of set B; then, (c) adding sequence Ti to a set A of actual bound sequences.

Another such method is a method for determining a set of potential double-stranded DNA binding site sequences equal to or less than a probe length L, of a DNA-binding protein which has been exposed to a set of nucleic acid probes P comprising substantially all possible sequences of length L, said protein having bound to subset B of said set P, by performing multiple sequence alignment analysis on the sequences of set B.

A related method is a method for determining a set of potential double-stranded DNA binding site sequences equal to or less than a probe length L, of a DNA-binding protein which has been exposed to a set of nucleic acid probes P comprising substantially all possible sequences of length L, said protein having bound to subset B of said set P, by using set B as an address into a pre-computed data structure wherein the contents of said data structure are sets of binding site sequences corresponding to said addresses.

Yet another method is a method of representing genes potentially affected by transcription factors comprising a data structure substantially equivalent to a directed graph wherein (a) at least one source node represents a DNA-binding protein identified as being bound to particular double-stranded DNA binding site sequences; and, (b) at least one target node represents a gene which is adjacent to a potential binding sequence for said protein.

Another method provides a process for determining a correspondence between the expression levels of genes and binding of DNA-binding proteins to double-stranded DNA binding site sequences by (a) running essentially simultaneously from portions of the same first sample a first mRNA expression analysis and a first double-stranded DNA binding analysis; (b) running essentially simultaneously from portions of the same second sample a second mRNA expression analysis and a second double-stranded DNA binding analysis; (c) comparing the change in results between said first mRNA analyses and said second mRNA analyses to identify a set G of genes which have changed in their expression level; and, (d) comparing the change in results between said first double-stranded DNA analyses and said second double-stranded DNA analyses to identify a set B of binding sites which have changed in their level of binding.

A method for producing a directed graph containing a representation of a substantially entire network of transcriptional activation and repression by combining a multiplicity of smaller graphs produced by an appropriate method described herein is also part of this invention.

Yet another method of this invention is a method for determining sequences containing the sequences of promoters of genes activated in a cell at a moment in time, by (a) contacting total mRNA isolated from the cell at the moment in time with a plurality of single-stranded total genomic nucleic acid probes, which may be in solution or in an immobilized state on a solid support and determining from analysis of the plurality which genes of the cell are being expressed, (b) contacting the total protein population isolated from the cell at the moment in time with a plurality of double-stranded nucleic acid probes which represent substantially all combinations of sequences of N base pairs in length, determining from analysis of the array the double-stranded nucleic acid probes which have been bound by a DNA-binding protein from the total protein population of the cell, and c) determining the nucleic acid sequences of the bound double-stranded nucleic acid probes, and thereby obtaining sequences containing the sequences of promoters activated in a cell at the moment in time.

A related method is a method for comparing gene activation in a first cell and a second cell, which comprises (a) contacting total mRNA isolated from a first cell with a plurality of single-stranded total genomic nucleic acid probes in solution or in an immobilized state on a solid support and determining from analysis of said plurality which genes of the cell are being expressed and contacting total mRNA isolated from a second cell with a plurality of single-stranded total genomic nucleic acid probes in solution or in an immobilized state on a solid support and determining from analysis of said plurality which genes of the cell are being expressed, (b) contacting the total protein population isolated said first cell with a plurality of double-stranded nucleic acid probes which represent substantially all combinations of sequences of length N in solution or in an immobilized state on a solid support and determining from analysis of said plurality the double-stranded nucleic acid probes which have been bound by a DNA-binding protein from the total protein population of said first cell; and contacting the total protein population isolated from said second cell with a plurality of double-stranded nucleic acid probes which represent substantially all combinations of sequences of length N in solution or in an immobilized state on a solid support and determining from analysis of said plurality the double-stranded nucleic acid probes which have been bound by a DNA-binding protein from the total protein population of said second cell,(c) determining the nucleic acid sequences of the bound double-stranded nucleic acid probes for said first cell, and thereby obtaining sequences containing the sequences of promoters activated in said first cell and determining the nucleic acid sequences of the bound double-stranded nucleic acid probes for said second cell, and thereby obtaining sequences containing the sequences of promoters activated in said second cell; and (d) comparing the sequences obtained for said first cell with the sequences obtained for said second cell, to determine gene activation in the first cell and in the second cell.

A further method of this invention is a method for obtaining a protein which binds to a specific double-stranded nucleic acid sequence by (a) providing a plurality of double-stranded nucleic acid probes which represent substantially all combinations of sequences of N base pairs in length, either in solution or in an immobilized state on a solid support, (b) contacting the double-stranded nucleic acid probes with a protein under conditions such that the protein binds to a specific double-stranded nucleic acid sequence of the plurality of double-stranded nucleic acid probes provided in step (a), and (c) separating the protein bound in step (b) from the specific double-stranded nucleic acid sequence to which the protein has bound in step (b) to obtain a protein which binds to a specific double-stranded nucleic acid sequence.

Another method of this invention is a method for obtaining a sequence containing the sequence of the promoter to which a transcription factor binds by (a) providing a plurality of double-stranded nucleic acid probes which represent substantially all combinations of sequences of N base pairs in length, either in solution or in an immobilized state on a solid support, (b) contacting the double-stranded nucleic acid probes with a transcription factor under conditions such that the transcription factor binds to a specific double-stranded nucleic acid sequence of the plurality of double-stranded nucleic acid probes provided in step (a); and (c) determining the specific double-stranded nucleic acid sequence to which the transcription factor has bound in step (b), thus obtaining a sequence containing the sequence of the promoter to which the transcription factor binds. Examples of solid supports are arrays or beads.

Also part of this invention is a method for determining that a protein is a double-stranded DNA-binding protein by (a) providing a plurality of double-stranded nucleic acid probes which represent substantially all combinations of sequences of N base pairs in length, either in solution or immobilized on a solid support, (b) contacting the double-stranded nucleic acid probes with the protein under which nucleic acid-binding proteins bind to double-stranded DNA, and (c) determining whether the protein has bound to a double-stranded nucleic acid sequence, thus determining that the protein is a double-stranded DNA binding protein.

Also part of this invention is a method for determining whether two double-stranded DNA-binding proteins bind to the same binding sites which comprises: (a) providing a first plurality of double-stranded nucleic acid probes which represent substantially all combinations of sequences of N base pairs in length, either in solution or immobilized on a solid support, (b) contacting the first plurality of double-stranded nucleic acid probes with the first protein under conditions appropriate for binding, (c) providing a second plurality of double-stranded nucleic acid probes which represent substantially all combinations of sequences of N base pairs in length, either in solution or immobilized on a solid support, (d) contacting the second plurality of double-stranded nucleic acid probes with the second protein under conditions appropriate for binding, and (e) determining the sequences of the probes to which the first and second proteins have bound, and (f) narrowing the bindng sites for each protein by analysis of the probe sequences, and (g) determining whether the two proteins bind to the same binding site by determining whether the two proteins have bound to the same subsequences of any bound probes.

BRIEF DESCRIPTION OF THE DRAWINGS

FIG. 1A: A Microarray Chip with single-stranded probes bound. Planar support (20) has a plurality of single-stranded probes. Probes (22) will typically be grouped into spots containing the same sequence, and the sequence of each spot's positions across the surface of the array will map to a known sequence for probes at that spot.

FIG. 1B: Beads with single-stranded probes bound. Beads (24) each have a plurality of single-stranded DNA attached as probes. Any given bead has only one DNA sequence of probes attached. Other beads in the solution typically have other DNA probe sequences on them.

FIG. 2A: DNA/tag hybrid. Tag (30) is attached to optional linker molecule (32) which is attached to DNA containing probe (34);

FIG. 2B: DNA alone—later purified and sequenced. A plurality of dsDNA probes containing different sequences (36) are free to bind to transcription factors (TF) in solution (38) if they are recognized by the transcription factor.

FIG. 10: One possible interpretation of the combined analysis of TF binding analysis and gene expression analysis. The gene expression analysis can be performed using microarray analysis techniques or other methods currently in use or which may yet be invented.

FIG. 11A: Diagram of gene activation via transcription factor and regulatory region showing the Promoter Region (120) of a hypothetical gene sequence, the Coding Region (122). Depicted in this FIG. are SEQ ID NO:29, and SEQ ID NO:25 (mRNA).

FIG. 11B: Three hypothetical genes and their promoter and Coding regions. Gene 1 is SEQ ID NOS:22-23; Gene 2 is SEQ ID NOS: 24, 26; Gene 3 is SEQ ID NOS:27-28.

FIGS. 12A, 12B and 12C: Use of DNA loops to present the probe substantially opposite to the binding site for the overall loop.

FIG. 13: Probes attached to a solid support via an Improved Linker molecule

FIG. 15: Flowchart showing a method for determining the Gross Binding Site Output using methods that do not permit determination of probe sequences using a spatially addressable mechanism.

FIGS. 19A, 19B and 19C: Venn Diagrams showing hypothetical cooperativity between binding site data. Area 220 in all figures is the universe of possible binding sites we are assaying for.

FIG. 19A: Venn Diagram showing (A) the Refined Binding Site sequences for Factor A.

FIG. 19B: Venn Diagram showing (B) the Refined Binding Site sequences for Factor B.

FIG. 19C: Venn Diagram showing (A), (B) and (A+B) the Refined Binding Site sequences for Factor A, Factor B and the Combined Factors A and B respectively. The extra binding Site sequences (A+B) demonstrates a cooperative binding effect between the two Factors not present when either one alone is exposed to the binding site assay.

FIGS. 22A, 22B and 22C: Promoter probe with random mutations.

FIG. 22A: The original gene with Promoter Region (270) and coding region (272)

FIG. 22B: The original gene's Promoter Region (270) with a forward flanking primer sequence (274) and a reverse primer region (276) that have been ligated onto the original Promoter Region. The forward primer (274) in the unmutated promoter may be flagged with a radioactive or fluorescent label (278).

FIG. 22C: Various instances of a whole population of mutated fragments created through random mutagenesis, such as PCR mutagenesis. Mutations (278) are shown schematically for the population of fragments which is intended to have many mutations in each position of the Promoter Region.

FIG. 23A: A standard Sanger sequencing gel showing the promoter region alone with primers such as shown in FIG. 22B.

FIG. 23B: What a sequencing gel would look like if it were run on a plurality of mutated promoters as shown in FIGS. 22C. At each band on the gel, a degeneracy of multiple bases would be seen (280). Primer ends, if sequenced, would remain fixed as shown by the area (282) in the top portion of the gel.

FIG. 23C: What a sequencing gel would look like if the randomly mutated sequences of FIG. 22C were subjected to selection by transcription factors, purified to obtain only those sequences that were bound to the transcription factors, and then sequenced. (One purification process would use the labeled promoter region to determine which band from a preparatory gel shift assay where promoters and transcription factors are presumably bound.) The bands of the sequencing gel where less than all of the bases are represented, for example, area (286) are bases offsets in the promoter region that demonstrate a transcription factor specificity. Bands of the gel still showing all bases, for example, area (284) are indicative of base offsets which transcription factors presumably do not bind. The DNA sequences of each member of the plurality can obtained by using the method of Iterated Sanger sequencing described in this application.

Figure 1A:
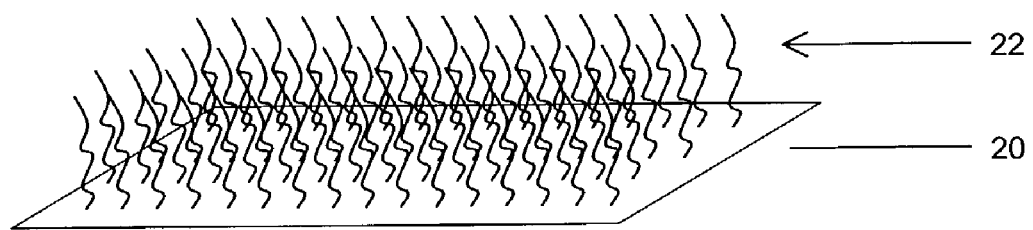
FIGS. 1A and 1B: Various known methods of attaching single-stranded DNA to solid supports.

In the drawings, a Transcription Factor, abbreviated TF, is meant to include factors that enhance, promote, repress or otherwise bind DNA or other TF's that do bind to DNA.

DETAILED DESCRIPTION OF THE INVENTION

Any terms not otherwise defined shall be given their standard meaning, in particular as used in Sambrook and Russell, Molecular Cloning: A Laboratory Manual Third Edition (Cold Spring Harbor Press, 2001). If appearing herein, the following terms shall have the definitions set out below. Nucleic acid molecule s include DNA and RNA as her e defined. DNA refers to a nucleic acid molecule which is a nucleotide monomer, or is the phosphate ester polymeric form of deoxyribonucleosides (the bases deoxyadenosine (A), deoxyguanosine (G), deoxythymidine (T), or deoxycytidine (C), and also any modified deoxyribonucleosides, such as inosine, or any alkylated (preferably methylated) or acylated, deoxyribonucleosides, or any phosphoester analogs thereof, such as phosphorothioates and thioesters, in single or double-stranded form. RNA refers to a nucleic acid molecule which is a nucleotide monomer, or is the phosphate ester polymeric form of ribonucleosides (the bases adenosine (A), guanosine(G), uridine (U) or cytidine(C) and also any modified ribonucleosides, for example methylated or acylated ribonucleosides) or any phosphoester analogs thereof, such as phosphorothioates and thioesters, in single or double-stranded form. Double stranded DNA-DNA, DNA-RNA and RNA-RNA helices are possible. Double-stranded means two strands of nucleic acid hybridized to each other via hydrogen bonding between their component bases (to form base pairs). In general a nucleic acid molecule is "hybridizable" to another nucleic acid molecule, such as a cDNA, genomic DNA, or RNA, when a single stranded form of the nucleic acid molecule can anneal to the other nucleic acid molecule under the appropriate conditions of temperature and solution ionic strength (see Sambrook, Fritsch, and Maniatis, Molecular Cloning: A Laboratory Manual Second Edition. (Cold Spring Harbor Press, 1989); and Sambrook and Russell, Molecular Cloning: A Laboratory Manual Third Edition (Cold Spring Harbor Press, 2001)). The conditions of temperature and ionic strength determine the "stringency" of the hybridization. For preliminary screening for homologous nucleic acids, low stringency hybridization conditions, corresponding to a $T_m$ of 55 degrees C., can be used, e.g., 5×SSC, 0.1% SDS, 0.25% milk, and no formamide; or 30% formamide, 5×SSC, 0.5% SDS. Moderate stringency hybridization conditions correspond to a higher $T_m$, e.g., 40% formamide, with 5× or 6×SCC. High stringency hybridization conditions correspond to the highest $T_m$, e.g., 50% formamide, 5× or 6×SCC. Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of $T_m$ for hybrids of nucleic acids having those sequences. The relative stability (corresponding to higher $T_m$) of nucleic acid hybridizations decreases in the following order: RNA:RNA, DNA:RNA, DNA:DNA. For hybrids of greater than 100 nucleotides in length, equations for calculating $T_m$ have been derived (see Sambrook et al. 1989, supra, 9.50-0.51). For hybridization with shorter nucleic acids, i.e., oligonucleotides, the position of mismatches becomes more important, and the length of the oligonucleotide determines its specificity (see Sambrook et al.,supra, 11.7-11.8). {A C G T} or {A C G U} is taken to include unmodified and modified nucleotides as described above.

The terms refer only to the primary and secondary structure of the molecule, and do not limit it to any particular tertiary forms. Thus, this term includes double-stranded DNA found, for example, in linear or circular DNA molecules (e.g., restriction fragments), plasmids, and chromosomes. In discussing the structure of particular double-stranded DNA molecules, sequences may be described herein according to the normal convention of giving only the sequence in the 5' to 3' direction along the non-transcribed strand of DNA (i.e., the strand having a sequence homologous to the mRNA). A recombinant nucleic acid molecule is a nucleic acid molecule that has undergone a molecular biological manipulation.

Unless otherwise specified, gene for purposes of these definitions includes the entirety of a sequence necessary for transcription and translation of a given protein, including 3' and 5' regulatory and flanking regions, and coding region.

A nucleic acid probe is a segment of DNA or RNA as defined above, for use in detecting its interaction with other molecules, in particular when used for an assay of this invention. More specifically, a single-stranded DNA probe is a single strand of DNA as described above. A double-stranded probe is a segment of double-stranded DNA as defined above. For purposes of this invention, this term includes RNA/RNA, or DNA/RNA segments. A plurality of probes is more than one such probe when used together in an assay of this invention, for example when grouped on a solid support or used together in solution for purposes of an assay of this invention. The probes may be obtained by conventional methods, such as cloning, PCR (polymerase chain reaction), or direct synthesis. For any probe of this invention, RNA is also contemplated, for example single-stranded, double-stranded, and closed circular loop probes, both in general and as limited by length or other characteristics.

A plurality of probes means nucleic acid molecules grouped together for purposes of this invention, e.g. a library. These probes may be attached in some way to a solid support, or may be together in solution. A target probe refers to a probe to which a given DNA-binding protein binds.

The length of the single or double-stranded nucleic acid probe may be any length "N" that allows a DNA-binding protein to bind. Preferably, the probe is at least three base pairs in length, and can be over one thousand base pairs in length. Convenient lengths are from about three through about ten, from about eleven through about seventeen, from about four through about thirty, or is from about seventeen through about one hundred. Thus N is preferably a number from three through ten, from eleven through seventeen, from four through thirty, or from seventeen through one hundred. The number of probes of a plurality will depend on various factors. Often, it is desired that the probes include substantially all combinations of sequences of N base pairs in length. For example the probes of the plurality may represent all possible three base pair sequences to all possible ten base pair sequences, all possible four base pair sequence to all possible eight base pair sequences, etc. The number of probes of a plurality will also depend to a certain extent on the nature of the plurality. For example, when the plurality is a support such as an array, spatial considerations may dictate the total number of probes. If the plurality is supported on beads, the spatial considerations are less limiting, while if the plurality is in solution, spatial considerations are even less limiting.

The actual sequence of a specific probe may be determined before it is used in an assay of this invention, or may be determined by standard methods after the assay has been run, preferably only if the probe has bound to a DNA-binding protein. For example, a random plurality of probes may be used in an assay. The sequences of the probes are not known beforehand. After the assay has been run, then any probe that has bound to a protein may then be sequenced by standard method. Thus, the probe sequences are not known in advance but are "knowable".

A DNA-binding protein is a natural or nonnatural (for example synthesized) protein capable of binding to a double-stranded DNA molecule (and under some circumstances to a double-stranded RNA molecule). The binding affinity of the protein for its binding site is normally represented by a $K_D$ of on the order of $10^{-9}$ to $10^{-10}$, although other binding affinities are possible and detectable. Examples of such proteins are proteins which interact naturally with DNA, such as proteins which bind to the regulatory regions of a genomic DNA molecule, e.g. to promoters (including enhancers), repressors, and the like. Examples of such proteins or peptides include transcription factors, DNA and RNA polymerases, and other trans-activating factors. Such proteins may be individual proteins, or a complex of proteins. For example, a DNA-binding protein includes a complex of proteins which bind to different regions of a DNA molecule but interact with each other, such as histones. DNA-binding drugs are considered DNA-binding proteins for purposes of this definition. Examples of such drugs are chloroquine, doxorubicin, actinomycin D, anthracyclines, amsacrine, cisplatin, experimental DNA-binding drugs such as recombinant zinc-finger proteins and polyamides (see Dervan and Burli Current Opinion in Chemical Biology 3: 688-693), and nonspecific dyes such as Hoechst 33258, ethidium bromide or DAPI, SYBR Green and SYBR Gold (Molecular Probes, Inc, Eugene, Oreg.), Methylene Blue.

A population of DNA-binding proteins for purposes of this invention may be a single purified protein, a preparation of multiple isolated proteins, or a preparation that contains proteins such as a cell lysate. Preferably molecules which would interfere with the binding of the DNA-binding proteins to their target probes are removed from the protein preparation prior performing a given assay of this invention. A target DNA-binding protein refers to a DNA-binding protein to which a given nucleic acid probe binds. It is useful to remove nonspecific DNA-binding proteins, which are proteins which bind anywhere on a DNA molecule and not at a specific sequence. This is done by conventional methods such as the use of poly dIdC (deoxy I/deoxy C), and manipulations of the stringency of hybridization conditions.

A population of DNA-binding proteins may be labeled before an assay of this invention is performed to facilitate detection and/or isolation of such proteins when bound to their target probes. Labeling may be done by conventional methods, and is further described below.

By binding is meant the attachment of one molecule to another as a result of natural forces which dictate such events. In the context of an assay of this invention, binding describes the interaction of a DNA-binding protein with its target nucleic acid probe, i.e. the probe which contains the natural binding site of the protein.

A transcription factor is a DNA-binding protein or a member of a DNA-binding protein complex which binds to one or more promoter sequences and thereby specifically influences the expression of the gene or genes regulated by the promoter sequence or sequences. Repressors are sequences which also have these properties and are included in the definition of transcription factors for purposes of this invention. Such factors may include RNA sequences or other non-protein moeities that act as co-factors for expression or repression.

A promoter region is a genomic DNA sequence that may be bound by a protein (a promoter, for example) which in turn influences the expression of nearby genes (i.e. of the coding region). Promoter regions may contain subregions to which a repressor protein binds. Enhancer regions are included in this definition. Enhancer regions may be located at a distance of up to fifty to one hundred kilobase pairs in a 3' or 5' direction from the start of the transcription site of the gene they influence. Promoter regions include the specific definition of promoter as a regulatory region capable of binding RNA polymerase in a cell and initiating transcription of a downstream (3' direction) coding sequence. Promoter regions include the minimum number of bases or elements necessary to initiate transcription at levels detectable above background. Within the promoter region will be found a transcription initiation site as well as protein binding domains responsible for the binding of RNA polymerase. Although promoter regions are typically found flanking the coding region of their gene, they may also be found within introns.

The natural binding site for the DNA-binding protein is that DNA sequence to which the DNA-binding protein binds in nature, for example the sequence of the promoter to which a transcription factor binds. The phrase "double-stranded DNA binding site sequences" as used below refers to the sequence of the natural binding site unless otherwise indicated.

The nucleic acid sequence specificity of a DNA-binding protein refers to the nucleic acid sequence of the particular individual or group of double-stranded nucleic acid probes to which the DNA-binding protein binds such that the binding is detectable in an assay of this invention. The sequence of the natural binding site described above may be identical to the sequence of the double-stranded nucleic acid probe, or may fall within that probe, i.e. when the probe is longer than the natural binding site. The probe may also be shorter than the natural binding site. A sequence is contained by a double-stranded nucleic acid probe when that sequence is consecutively present in the probe, i.e. is a subsequence of the entire sequence of the probe.

A solid support refers to any chemical structure to which an array of probes can be directly or indirectly attached. Upon such attachment the probes are considered to be immobilized. Exemplary solid supports are arrays such as described in U.S. Pat. No. 5,143,854. An array generally accommodates about one to ten thousand probes, although an amount of probes exceeding one million is possible with advances in miniaturization. Glass is a typical array material. Beads are another example of a solid support. Beads may be made of various materials, such as polystyrene. (For examples of attachment chemistry, see Hermanson, et al., Immobilized Affinity Ligand Techniques (Academic Press 1992); Fodor, et al. 1991 Science 251:767-773.)

It is not necessary for the probes to be immobilized in assays of this invention. For example, the plurality of probes may be combined with the target DNA-binding protein population when both are in solution. Conditions may be adjusted to enhance targeted binding. It will generally be desirable to mimic natural cellular conditions such as salt content, pH, protein concentration, and other factors. For example, conditions similar to those used for Gel Shift Assays and are applicable to this method (See Short protocols in molecular biology, 4$^{th}$ Edition, Frederick M. Ausubel et al. eds. John Wiley & Sons (1999); and Molina, D. et al. *Nucleic Acids Research* 29: 479-487, 2001.)

By attached directly or indirectly to a solid support is meant that each member of the plurality of nucleic acid probes is connected to the solid support either by one of its own moieties or by way of a linker molecule that is connected to both the nucleic acid probe and to the solid support. See Hermanson, supra.

By elements is meant all the components existing in an assay environment during the performance of the assay. These components include the probes on the solid support, the solid support itself, the DNA-binding proteins in the DNA-binding protein preparation, any other molecules that might be present in the DNA-binding protein preparation. Examples are zinc, salts, bovine serum albumin, and other conventional components of a protein preparation or a cell lysate.

Binding interference refers to any physical or chemical impediments, preferably on a molecular scale, that would hinder the binding of a DNA-binding protein to its target nucleic acid probe in an array of this invention which has been designed to minimize such binding interference. Two particular forms of binding interference are steric (spatial) and electrostatic.

By methods disclosed herein, such binding interference can be minimized. By minimized is meant that there is less binding interference in an array of this invention, than in an array which is otherwise similar but where binding interference has not been minimized. The reduction in binding interference may be determined by performing the same assay on an array of this invention where binding interference has been minimized, and on a conventional array with no minimization, preferably with a preparation limited to one target protein (i.e. just one species of DNA-binding protein). The arrays are then compared, and the binding quantified by any standard method. More target proteins will have bound to the array of this invention than to the other array, demonstrating minimization of binding interference in the array of this invention.

A moment in time use with reference to a cell refers to cells in a given state which can be assayed by methods of this invention to determine, for example, what genes have been activated to elucidate an activation pattern for the cell in that given state. The "moment in time" refers to the cell's state at the time the mRNA and proteins of this cell are harvested for purposes of assay. These cellular components need not be assayed immediately. For example the components may be frozen for assay at a later time. The "moment in time" would not be the time of the assay, but that time, even in the past, that the components were harvested. For example, cells can be arrested at a particular stage in their cell cycles by known methods. The point of arrest would be the moment in time for purposes of this invention. Cells may be exposed to certain conditions prior to assay. Any time after the exposure to the conditions and just before the assay begins is also a moment in time in this invention. In addition, cells which have not been treated in any particular way are considered to be at a "moment in time" at any given time at which they are sampled. This invention also contemplates that cells can be assayed together which are at different "moments in time".

The term "cell" refers to any known cell, including eukaryotic and prokaryotic cells, cells of unicellular microorganisms, and cells of multicellular organisms, including cells of specific tissues, and cells in specific stages or conditions (for example a transformed cell, a cancer cell, a stem cell). When cell is referred to in the context of an assay such as the above, cell is generally taken to mean a cell population.

In general throughout this application, cell lysates may be obtained and prepared by known methods, depending on cell type and organism (for example in plant cells the cell wall would have to be broken down). Cells may be mitotically synchronized. Yeast cells, in particular synchronized yeast cells, are useful. Whole cell lysates, nuclear extracts, cytoplasmic extracts, and any cell extract containing DNA, RNA, and transcription factors is useful. Preferably the extract is in near-native conditions, and no denaturing conditions prevail. EDTA may be initially used to stop proteolysis. Mild conditions simulating natural conditions are preferable. Alternatively, total proteins can be purified from cells or generated using recombinant DNA techniques by conventional methods for use.

In accordance with the present invention there may be employed conventional techniques in the relevant art, including data analysis, array technology, molecular biology, microbiology, protein chemistry, and recombinant DNA within the skill of the art. Such techniques are explained fully in the literature. See, e.g., Sambrook, Fritsch & Maniatis, *Molecular Cloning: A Laboratory Manual*, Second Edition (1989) Cold Spring Harbor Laboratory Press, Cold Spring Harbor, N.Y. (herein "Sambrook et al., 1989"); Sambrook and Russell, Molecular Cloning: A Laboratory Manual Third Edition (Cold Spring Harbor Press, 2001), *DNA Cloning: A Practical Approach*, Volumes I and II (D. N. Glover ed. 1985); *Oligonucleotide Synthesis* (M. J. Gait ed. 1984); *Nucleic Acid Hybridization* [B. D. Hames & S. J. Higgins eds. (1985)]; *Transcription And Translation* [B. D. Hames & S. J. Higgins, eds. (1984)]; *Animal Cell Culture* [R. I. Freshney, ed. (1986)]; *Immobilized Cells And Enzymes* [IRL Press, (1986)]; B. Perbal, *A Practical Guide To Molecular Cloning* (1984); F. M. Ausubel et al. (eds.), *Current Protocols in Molecular Biology*, John Wiley & Sons, Inc. (1994); Stryer, Biochemistry Fourth Edition (1995), U.S. Pat. No. 5,143,854

In one aspect, this invention is directed to an array of nucleic acid probes attached directly or indirectly to a solid support. Although this array is particularly useful for screening DNA-binding proteins, other entities may also be assayed. For example other proteins which are not identified DNA-binding proteins may be assayed on the arrays of this invention. Fragments of proteins may also be used. Other chemical entities may be used, for example pharmaceutically active nonprotein compounds may be assayed using the arrays of this invention Synthetically generated nucleic acid sequences are widely available commercially, and methods of synthesizing desired single stranded DNA sequences are well known to those of skill in the art. Methods of forming large arrays of spatially restricted (e.g. on a planar surface) single-stranded and double-stranded oligonucleotides have been described in the literature, and in particular, by Pirrung et al. in U.S.

Pat. No. 5,143,854; Fodor et al., *Science*, 251:767-777 (1991); and Lockhart et al. U.S. Pat. No. 5,556,752, Bulyk, M. et al., *Nature Biotechnology* 17: 573-577 (1999), which are incorporated herein by reference.

Methods of synthesis of single-stranded and double-stranded DNA combinatorial libraries that may be used for assays of the current invention are well covered in the literature. While the beads have not been widely used for dsDNA binding assays, details on the in situ synthesis of oligonucleotide probes on beaded solid supports is described in U.S. Pat. No. 5,846,719 (Brenner et al.); U.S. Pat. No. 6,013,445 (Albrecht et al.); U.S. Pat. No. 5,604,097 (Brenner); Needels, M. C. et al. *PNAS* 90: 10700-10704 (1993); Brenner S. et al., *PNAS* 97:1665-1670 (2000); and Brenner S. et al. *Nature Biotechnology* 18: 630-634 (2000) which are incorporated herein by reference.

The probes are constructed to minimize binding interference between any one or more DNA-binding proteins and any probe of the array for which the DNA-binding protein is specific (i.e. can bind), when the binding interference is caused by one or more elements which would otherwise (i.e. if the probes had not been constructed to minimize binding interference) hinder the binding of the first DNA-binding protein to the first probe of said array, when the array is exposed to a population of DNA-binding proteins. This can be determined by, for example, performing the same assay on a nonminimized array, and an otherwise identical array on which binding interference has been minimized, and comparing desirable binding on each. It will be seen that in the array of this invention, desirable binding is enhanced.

Particular elements to which binding interference is minimized include other probes of the array, DNA-binding proteins, and any part of the solid support itself. Any array of this invention may contain a plurality of nucleic acid probes which represent substantially all combinations of sequences of N base pairs in length. For any of these arrays, the nucleic acid probes used may be single or double-stranded RNA or DNA probes, and are preferably double-stranded DNA probes. Also part of this invention is a method of producing any of these arrays.

Minimization of binding interference is accomplished by working with the nucleic acid probes of the array. For example the probes can be designed to be more compact, to be distanced from their attachment site on the array, to be less densely packed with the other probes. To achieve minimized binding interference, at least one probe on the array should be so designed, and preferably about 60% to 100% of the probes on the array should be so designed. See FIGS. 12 and 13.

One means of minimizing binding interference is to use closed circular loops of nucleic acid as probes. These closed circular loops can be made by conventional methods, and may range from about fifty base pairs to about two or three hundred base pairs in length, although longer loops are possible. As shown in FIG. 12, each loop has two opposite sides, by which is meant one side is one half the total number of base pairs from the other. The first side and the second side can each contain one or more functional sites, which may be different or the same. Preferably the nucleic acid loop is attached to the solid support (directly or indirectly) by a functional site on the "first" side, and has its binding site for a DNA-binding protein on the opposite or "second" side. "First" and "second" are used here simply for convenience to distinguish the two sides and have no other significance. Either side can be the first or second side.

Another means of minimizing binding interference is to attach the nucleic acid probes to the array via a linker molecule which is attached to the probe by an attachment site, and also attached to the solid support. A linker effectuates a linkage between two molecules. The nature of the linkage can be any known chemical or physical method for linking to molecular moeities to each other. For example the linkage can be a chemical bond such as a covalent bond, or can be an affinity linkage, which includes electrostatic types of linkage, ionic bonds, hydrogen bonds, bonds involving Van der Waal's forces, any combination of these, and the like. An example is biotin or a site equivalent to biotin, and avidin or streptavidin. Thus the nucleic acid probe can be biotinylated, i.e. have an attachment site which is biotin or an equivalent, and the linker would effectively be avidin or streptavidin which is modified such as to bind it to the array. Conventional methods may be used.

In more detail, it is possible that steric interference caused by high density probes attached to the solid support in microarrays could interfere with efficient binding of the Target (i.e the molecule intended for binding to the probe, such as a nucleic acid, or an affinity molecule such as a ligand or antibody, or a protein as disclosed herein) to the probes. In classical microarrays the probes are single stranded nucleic acids and the Targets in general are nucleic acids, and linker molecules made from extra nucleotides or other linear molecules, such as an aliphatic carbon chain placed between the solid support and the nucleic acid probe before hybridization are sufficient to deal with the steric interference.

When targeting larger molecules (such as proteins), and/ or when using double-stranded probes, these known linker sequences may not be sufficient to avoid steric interference or electrostatic interference between neighboring probes on the solid support (usually a chip or glass slide) a molecular spacing structure, is used. Preferably this molecule has a slightly larger surface area than the steric or electrostatic interference area.

There are a number of known molecules which could serve this function including, for example, many globular proteins (found in nature, or synthetic), polystyrene or resin beads (made for example from the same polymers as that used in chromatographic columns designed for low non-specific binding affinity—available from, for example, the Pierce Chemical company, Rockford, Ill.), carbon nanotubes or "buckyballs".

If this molecular spacing structure is relatively large (e.g. has a large "footprint"), there will be a low density of probes, if it is relatively small, then it will allow a high density of probes. The primary purpose of the molecular spacing structure in this application is to reduce the density of probes below that which occurs naturally by binding probes directly to the solid support, or via a conventional very small linker (e.g. with a very small footprint). In this way, the solid support may be functionalized to allow the covalent (or strong non-covalent) binding of the molecular spacing structure to the surface, and the probe can be arranged to be on substantially the opposite side of the molecular spacing structure from the solid support binding face. See FIG. 13.

Preferably the molecular spacing structure would have the following characteristics:

1) The molecular spacing structure should be inert with respect to the Target of interest (preferably a DNA-binding protein), or known affinity should be controlled for and accounted for in some cases;

2) The molecular spacing structure should similarly not repel the Targets of interest;

3) The molecular spacing structure should have a larger footprint than the Target of interest so that the Targets, if bound, will not repel or displace one another;
4) The molecular spacing structure should be of such a nature that it can be chemically manipulated such that once the molecular spacing structure is bound to the solid support on one of its surfaces, the probe can be projecting substantially away from the solid support to allow for the free, unencumbered hybridization of Target molecules.

Molecules that are now known which can satisfy these criteria include antibodies and other naturally occurring proteins that are known to bind very specifically to other molecules. Therefore, if the Target molecules are transcription factors, antibodies, which are shown to be inert with respect to the target (i.e. are not specific for the transcription factors), may be used. One means of attachment involves the treatment of the solid support with a high density of antigens which also do not interact with the targets of interest, attaching nucleic acid probes via a short traditional linker to the Fab antibody fragments on the non-binding end, and spotting the Fab/probe molecule onto the solid support. Washing to remove excess unbound Fab/probe fragments will leave a solid support with a maximum density of probes equal to the maximum density of Fab fragments on the surface. In general, this will be lower than the density of probes obtained by functionalizing the surface with a substance designed to bind the probes directly.

The steps outlined above are an example only, and are not meant to limit the invention in any way. Other means of using molecular spacing structures include:
1) Attaching the probe to the molecular spacing structure first and then attaching the molecular spacing structure to the solid support (described above).
2) Attaching the molecular spacing structure to the solid support first, and adding the probes to the molecular spacing structure second.
3) Simultaneous attachment of molecular spacing structure to support and to probe via the use of specific binding sites for each on substantially opposite sides of the molecule.
4) The use of a number of sites for probe on the molecular spacing structure which are naturally separated, and one or more sites for binding to the support.
5) The use of various sizes of molecular spacing structures for different applications.
6) The use of molecular spacing structures of different geometry or structure such that the ideal probe placement is not opposite the solid support, but rather in some other orientation or geometry. One application of this might be non-planar solid supports. Another application might involve tests for the sensitivity of target molecules to steric or electrostatic interference by intentional design of probe placement in 'non-ideal' positions.
7) The use of molecular spacing structures which are themselves an assembly of smaller molecules (i.e. a complex of covalently bound molecules such as a viral capsule particle or other multi-subunit structure.)
8) The combination of this technique with light-activated probe development such as that described in U.S. Pat. No. 5,143,854 and Shalon et al. 1995 Science 270:467-470.
9) to extend single-stranded probes in-place from the solution-facing side of the molecular spacing structure. Such probes would have the benefits of the light-activated extension with the lower density afforded by the molecular spacing structure molecules.
10) Any of these other specialized applications may violate some of the principles of the "idealized" molecular spacing structure above—particularly if the intent is to test the effect of varying one of those parameters—as in (item 6 of this list).
11) This method applies when the probes are double-stranded DNA, single-stranded DNA, single-stranded RNA, double-stranded RNA, DNA/RNA hybrids, proteins, ligands, antigens, or any other molecule.

For references to proteins that may be used, see *Introduction to Protein Structure and Function*, Second edition, by Carl Branden & John Tooze, (Garland Publishing, 1999).

As noted above, another approach to allowing access to probe binding domains in cases where steric or electrostatic interference may be a problem is to use nucleic acid (such as DNA) loops instead of linear strands. Such loops would ideally have the probe domain of the molecule farthest away from the solid support by using a loop wherein the substantially opposite side of the loop (i.e. ½ the total number of base pairs away from the probe site) is bound to the solid support, and the probe sequence is allowed to hybridize freely to factors or other nucleic acids in solution.

One possible embodiment is illustrated in FIG. 12. In this case, short linear DNA molecules may be synthesized containing the probe sequence, and then ligated to another DNA strand in a circular manner. The second DNA strand in this case already contains a solid support-binding moiety. Upon spotting of these circular fragments to the solid support, the support-binding moiety can be covalently or non-covalently attached as appropriate.

Alternate embodiments include:
1) The use of complementary and specific pairs of molecules on the substrate binding region of the loop, and the surface such as biotin and streptavidin or avidin.
2) If DNA is to be used to complete the loop, and the Target molecules are, for example transcription factors (TF's), then it is reasonable to assume that some of the TF's might bind to the non-probe region of these loops. At least two alternate approaches are possible to deal with this issue:
   a) Use only DNA sequences for the non-probe region of the loop which are known not to bind any targets—this may be determined, for example by iterative applications of the DNA motif detection algorithm (described elsewhere in this patent, and/or
   b) Use known sequences, and allow the algorithm to consider the entire loop sequence when determining putative binding motifs.

For both of the above methods to minimize binding interference, known methods of protein or DNA synthesis chemistry, organic covalent binding reactions and activating and protecting various groups in order to prevent or promote binding may be used. At the moment, the literature abounds with methods for activating solid supports, and for attachment of molecules to supports. For example, see Hermanson, et al. Immobilized Affinity Ligand Techniques (Academic Press 1992). In addition, antibodies are very often covalently attached to resins and chromatography columns for purification by methods known in the art.

In a preferred embodiment, one or more probes of the array are closed circular loops of nucleic acid, one or more of which is attached to the solid support via a linker molecule. In a preferable design for such a closed circular loop nucleic acid probe, there is an attachment site on one side to a linker molecule which itself attached to the solid support, by which that side of the loop is attached to the solid support. On the opposite side is the binding site for a DNA-binding protein. It is possible to have any combination of unmodified probes, circular loop probes, and probes attached by linkers in one array. However, in a specific embodiment all the probes are circular loops of nucleic acid and all these probes are attached to the array by a linker molecule. In one embodiment, the linker is an affinity linker, for example biotin, and the linker is avidin or streptavidin, as described immediately above. Such a probe may be produced by known methods of automated nucleic acid synthesis, for example by synthesizing as single strands the two "halves" of the probe as known sequences, and between the two "halves", the first and second sides. On the first side may be placed the DNA-binding protein binding site, which may be for example a random sequence, or one sequence among the N sequences as defined elsewhere, and on the other side may be placed the attachment site, which may be a specific functional sequence as desired. See FIG. 12. The single strands can be made double-stranded by known methods as described elsewhere. The loops are then made by ligating the ends of the double-stranded probes to each other using conventional technology. In more detail, when the single-stranded probes may be synthesized to have specific "sticky ends" to obtain specific ligation of the ends to each other to create loops.

As detailed above, yet another method for minimizing binding interference is to attach the nucleic acid probes (which may optionally be in the form of closed circular loops) to the array via a molecular spacing structure. Any molecular spacing structure which causes the probes to be packed less closely than in an array lacking the molecular spacing structure, and which does not impede binding of DNA-binding proteins to probe, may be used as long as it is chemically suitable. A protein is one example of a suitable spacing structure. In one embodiment, a globular protein is used. Other protein shapes are also useful, for example proteins that are roughly cubical or spherical in shape. Preferably the nucleic acid probe is attached to the protein and the protein attached to the solid support in such a way that the probe is oriented approximately perpendicular to the solid support. For example the probe may be oriented in a position precisely perpendicular to the solid support, or within a range of about 80 degrees to about 110 degrees.

The binding interference may be steric or electrostatic. In one array of this invention, binding interference is minimized because at least one of the probes in the array, or any number of probes up to the total number of probes, is a closed circular loop of nucleic acid which comprises two opposite sides, the first side of the loop containing a binding site for a DNA-binding protein and the second side of the loop containing an attachment site to a linker molecule which linker molecule is itself attached to the solid support, by which attachment site the second side of the loop is attached to the solid support. The closed circular loops may be single or double-stranded RNA and/or DNA, and are preferably double-stranded DNA. A method of producing any of these arrays is also part of this invention.

The closed circular loop probe may be any size that minimizes binding interference as above, and is preferably from about 50 to about 300 base pairs in length. Lengths greater than 300 base pairs are also contemplated. Convenient lengths range from about 50 to about 100 base pairs, and from about 100 to about 300 base pairs. In one embodiment, the probe and the linker may be attached by a covalent linkage. Thus the second side of the closed circular loop probe may be attached to the solid support via a linker molecule which provides a covalent link between the attachment site on the second side of the loop and the corresponding attachment site on the linker molecule. In another embodiment, the probe and linker may be attached by affinity binding. Thus the second side of the closed circular loop probe has an attachment site for an affinity linker which linker is attached to the solid support, by which attachment site for the affinity linker the closed circular loop is accordingly indirectly attached to the solid support. For example, in one embodiment the attachment site for an affinity linker is biotin and the affinity linker is avidin or streptavidin, the avidin or streptavidin being directly attached to the solid support. A method of producing any of these arrays is also part of this invention. Avidin and biotin may be bound to nucleic acids and solid supports such as glass by known methods. Other conventional binding pairs can also be used (see, for example, Hermanson, et al. Immobilized Affinity Ligand Techniques (Academic Press 1992), and the Special Issue on (strept)avidin-biotin in *Biomolecular Engineering* volume 16, 1999.)

In another array of this invention, binding interference is minimized because at least one probe is attached to the solid support by a molecular spacing structure which is bound to both the probe and to the solid support such that the binding of a DNA-binding protein to the probe is not impeded and the probe is packed less closely to neighboring probes in the array. In one embodiment, the molecular spacing structure is a protein, in particular a globular protein. Proteins of other shapes may also be used. Roughly spherical or cubical proteins are also useful molecular spacing structures. The probe may preferably be oriented approximately perpendicular to the solid support, but can be oriented in any position within the physical limitations of the environment.

Another part of this invention is a method for binding a DNA-binding protein to a nucleic acid probe in an array of nucleic acid probes attached directly or indirectly to a solid support where binding interference between the DNA-binding protein and the probe caused by one or more elements which would otherwise hinder their binding when the array is exposed to a population of DNA-binding proteins, is minimized because of the manner in which the probes are constructed. The nucleic acid probes used may be single or double-stranded RNA and/or DNA probes, and are preferably double-stranded DNA probes. The array may contain a plurality of nucleic acid probes which represent substantially all combinations of sequences of length N. Examples of possible sources of binding interference are steric and electrostatic.

In one such method at least one of the probes in the array, or any number of probes up to the total number of probes, is a closed circular loop of nucleic acid which comprises two opposite sides, the first side of the loop containing a binding site for a DNA-binding protein and the second side of the loop containing an attachment site to the solid support by a linker molecule by which the second side of the loop is attached to the solid support by a corresponding attachment site on the solid support. The probe is preferably from about fifty to about three hundred base pairs in length, but lengths greater than 300 base pairs are also contemplated. Convenient lengths are from about 50 to about 100 base pairs, and from about 100 to about 300 base pairs.

In one embodiment of this method, the probe and the linker may be attached by a covalent linkage. Thus the second side of the closed circular loop probe may be attached to the solid support via a linker molecule which provides a covalent link between the attachment site on the second side of the loop and the linker molecule which is itself attached to the solid support, by which attachment site the second side of the loop is indirectly attached to the solid support. In another embodiment, the probe and linker may be attached by affinity binding. Thus the second side of the closed circular loop probe has an attachment site for an affinity linker and the linker molecule has a corresponding attachment site for the affinity linker. For example, in one embodiment the attachment site for an affinity linker is biotin and the affinity linker is avidin or streptavidin which is directly attached to the solid support.

In another embodiment of this method, binding interference is minimized because at least one probe is attached to the solid support by a molecular spacing structure which is bound to both the probe and to the solid support such that the binding of a DNA-binding protein to the probe is not impeded and the probe is packed less closely to neighboring probes in the array. In one embodiment, the molecular spacing structure is a protein, in particular a globular protein. Proteins of other shapes may also be used. Roughly spherical or cubical proteins are also useful molecular spacing structures. The probe may be oriented approximately perpendicular to the solid support. For example the probe may be oriented in a position precisely perpendicular to the solid support, or within a range of about 80 degrees to about 110 degrees. A method of producing any of these arrays is part of this invention as described above.

Also part of this invention are various methods wherein double-stranded nucleic acid probes are used to obtain or investigate the properties of DNA-binding proteins. Although these methods are particularly useful for DNA-binding proteins, other entities may also be assayed using the methods described herein. For example other proteins which are not identified DNA-binding proteins may be used in methods of this invention. Fragments of proteins may also be used. Other chemical entities may be used, for example pharmaceutically active nonprotein compounds may be assayed using the methods of this invention For any of these methods, the nucleic acid probes used may be double-stranded RNA and/or DNA probes, and are preferably double-stranded DNA probes. That a DNA-binding protein has bound to one or more double-stranded nucleic acid probes of a plurality of such probes may be determined by a number of conventional methods. For example, spectroscopic characteristics indicative of proteins bound to a probe may be detected by fluorescent tags, absorbance, nuclear magnetic resonance (NMR), or other known methods of detection. In these methods, the nucleic acid probes may be in solution or immobilized on a solid support, such as an array. When the nucleic acid probes are on an array, in one embodiment the array may be an array of this invention as described above, where binding interference has been minimized.

The information produced by completing the assays of this invention may be considered Gross Binding Site Data, which Data may be used in the analytic methods of this invention to further refine the information obtained about binding specificity. Gross Binding Site Data means in general the sequences of all the probes used in an assay and which of those probes have bound to the Target.

The protein may have a naturally measurable characteristic, or can be modified by known methods to make it spectroscopically detectable. For example, the protein may be modified to contain radioactive isotopes so that its binding can be detected by such known techniques as autoradiography, fluorescent phosphor imaging, or other conventional radioactive detection methods. Mass spectrometry may also be used.

Competitive detection methods may be used, for example competing proteins or molecules which are known to bind to a sequence contained by the double-stranded nucleic acid probe may be suitably labeled and detected by any of the above methods, where the presence of the competing protein or other molecule indicates the absence of the DNA-binding protein, or the absence of the competing protein or other molecule indicates the presence of the DNA-binding protein. As stated above, for any of these methods, particularly as described below, the nucleic acid probes used may be double-stranded RNA and/or DNA probes, and are preferably double-stranded DNA probes.

In the methods of this invention, the plurality of probes may be selected according to any criteria. For example the plurality of probes may be generated randomly by well known methods. Alternatively, the plurality of probes may be selected to represent substantially all combinations of sequences of N base pairs in length, or the plurality may be selected based on different criteria. With regard to the former, the plurality may represent a selected subset of sequences of N base pairs in length, or a combination of subsets of such probes, for example a number of probes three base pairs in length and a number of probes of five base pairs in length, or other combinations. The plurality may also be selected on the basis of specific criteria, for example based on some amount of prior knowledge as to what type of sequence a DNA-binding protein to be assayed binds.

For example, a method of this invention for determining the nucleic acid sequence specificity of a DNA-binding protein by (a) providing a plurality of double-stranded nucleic acid probes, which may be selected according to any criteria, but which preferably represent substantially all combinations of sequences of N base pairs in length or subsets thereof, either in solution or in an immobilized state on a solid support, (b) contacting the double-stranded nucleic acid probes with a DNA-binding protein under conditions such that the DNA-binding protein binds to one or more specific double-stranded nucleic acid probes of the plurality of double-stranded nucleic acid probes provided in step (a), and (c) determining the sequences of the specific double-stranded nucleic acid sequence to which the DNA-binding protein has bound in step (b); thus determining the nucleic acid sequence specificity of the DNA-binding protein. Examples of solid supports are arrays and beads. The sequence of the nucleic acid probe may be determined before the assay is performed, or may be determined afterwards, for example if it is a probe to which a DNA-binding protein has bound. Conventional conditions such as those used in gel shift assays are preferable. Conditions sometimes used in some types of foot-printing assays may be too harsh.

N may be any number which operates in this method, but preferably N is a number from three through ten, from eleven through seventeen, or is from seventeen through one hundred.

The above method may also include a prescreening step (a-1), after the probes are obtained and before the protein is added, in which the double-stranded nucleic acid binding probes are prescreened to remove those probes which are known not to bind to the DNA-binding protein whose specificity is to be determined.

The double-stranded nucleic acid probes of this method may be directly attached to the solid support, or may be attached to the solid support by a double-stranded nucleic acid linker which is known to lack any binding site for the DNA-binding protein whose specificity is to be determined. Alternatively, the double-stranded nucleic acid probes may be attached to the solid support a by double-stranded nucleic acid linker whose sequence is known and can therefore be discounted if bound by a DNA binding protein.

For example, to determine that a probe is inert, a preliminary assay is run and any probe that is not bound by the target protein is inert and may be used as a linker in the next assay. Alternatively, the sequence of the probe may be determined and this sequence may then be "discounted" from the data analysis once the assay is run, by using for example the focusing algorithm provided below.

In one embodiment of this method, N is selected to be longer than the expected length of the binding site of the DNA-binding protein whose specificity is to be determined. Experimental evidence may be used to estimate binding site length. In general about 17 base pairs long is the maximum for a single factor. In order to further elucidate the natural binding site for the DNA-binding protein, step (d) may additionally be performed in which the nucleic acid sequence specificity of the DNA-binding protein which has bound to a set of probes longer than its natural binding site is determined to provide the sequence of the natural binding site.

As stated above, this invention includes analysis methods described below which may be used independently, but preferably are used in conjunction with assays of this invention, in particular assays using double-stranded DNA probes. Accordingly the data used for these analysis methods is conveniently obtained from the assays described herein for example Gross Binding Site Data). In particular, data on the potential nucleic acid sequences (although double-stranded DNA sequences are specified, any nucleic acid sequence for which Gross Binding Site Data is obtained may be used) to which DNA-binding proteins bind, may be obtained as described in the assays of this invention. Although these methods are particularly useful for DNA-binding proteins, other entities may also be assayed using the methods described herein. For example other proteins which are not identified DNA-binding proteins may be used in methods of this invention. Fragments of proteins may also be used. Other chemical entities may be used, for example pharmaceutically active nonprotein compounds may be assayed using the methods of this invention Part of this invention is a method for determining a set of potential nucleic acid sequences, in particular double-stranded DNA binding site sequences equal to or less than a probe length L, of a protein, for example a DNA-binding protein, which has been exposed to a set of nucleic acid probes P, and has bound to subset B of said set P wherein, for each possible nucleotide sequence Ti of non-zero length and shorter or equal to length L, the following steps are performed: (a) comparing said sequence Ti to the sequence of each member Pj of set P and, if Ti is a subsequence of the sequence of Pj; then, (b) adding Pj to a set Hi of hypothetical probes corresponding to sequence Ti, and if Hi is a subset of set B; then, (c) adding sequence Ti to a set A of actual bound sequences. A step comprising the process of eliminating any sequences in set A which contain within them other sequences in set A may be added at any point in this method. With or without the elimination step, a preferred set of probes P comprises substantially all possible sequences of length L. A subset of substantially all possible sequences of length L is all possible sequences of length L, which is another alternative of use in this method. Substantially all possible sequences of length L includes all possible sequences and also includes less than all possible sequences. In this context less than all means a majority of all possible sequences, or at least 50% or more, preferably 80% to 99%.

When the above method is performed with the elimination step, one embodiment is a method of identifying genes proximal to potential double-stranded DNA binding sites using a library of probes which comprise substantially all probe sequences needed to determine any unknown binding sequence of length L (this may be mathematically determined by a person skilled in the art), or alternatively substantially all the possible sequences of length L. The identification may be performed by an electronic database search through a database containing genomic data containing gene coding sequences and their neighboring noncoding sequences. Alternatively, it may be performed by using primers corresponding to said binding sequences under conditions of a polymerase chain reaction in order to amplify nearby genes for isolation and identification, or may be performed by using said binding sequences as sites for restriction enzymes and isolating the resulting adjacent gene. For PCR methods, primers with the binding site sequence (a good length is L=17) may be used. In searching in a gene database, the binding sites may be smaller, or used in combinations which would be prohibitively difficult using PCR.

It is possible to add a step to both variants of the method above (i.e.with or without the elimination step) before step (a) in which (a-1) if set A of actual bound sequences does not already contain a subsequence of Ti proceed to step (a), otherwise proceed to the next Ti. In any variant of this method, the sequences of Ti are preferably composed from the set {A C G T }, or are composed from the set {A C G T X} where X is the do not care condition. In particular the sequences of Ti may be composed from a set which is itself a subset of a set of 16 symbols each of which match any of the members of a distinct one of the subsets of the set {A C G T}. This may be expressed as the method where (a) the sequences of Ti are composed from a subset of a set of 16 symbols; and, (b) each of said 16 symbols matches any of the members of a distinct one of the 16 possible subsets of the set {A C G T}, or the method where (a) the sequences of Ti are composed from a subset of a set of 16 symbols;(b) each of said 16 symbols corresponds to a distinct one of the 16 possible subsets of the set {A C G T}; and,(c) each of said 16 symbols matches any of the members of said one of the 16 possible subsets of the set of {A C G T} to which it corresponds. The set {A C G U} or {A C G T U} may also be used in any of the relevant methods described herein. Also throughout this application, sets including modified bases such as inosine, or other modified bases, may also be used. Note that the 16 possible subsets correspond to a four-membered set. For a larger set, the number of possible subsets will increase accordingly.

Also part of this invention is a method for determining a set of potential double-stranded DNA binding site sequences equal to or less than a probe length L, of a DNA-binding protein which has been exposed to a set of nucleic acid probes P comprising substantially all possible sequences of length L, said protein having bound to subset B of said set P, by performing multiple sequence alignment analysis on the sequences of set B. In one embodiment the set of probes P comprises all possible sequences of length L.

Also part of this invention is a method for determining a set of potential double-stranded DNA binding site sequences equal to or less than a probe length L, of a DNA-binding protein which has been exposed to a set of nucleic acid probes P comprising substantially all possible sequences of length L, said protein having bound to subset B of said set P, by using set B as an address into a pre-computed data structure wherein the contents of said data structure are sets of binding site sequences corresponding to said addresses. In one embodiment, the set of probes P comprises all possible sequences of length L. In another embodiment, if an address corresponding to a set B does not exactly match an address that has associated with it a non-empty set of binding site sequences, then a set of binding site sequences is retrieved from at least one nearest neighbor within the entire address space which does have associated with it a non-empty set of binding site sequences. A preferred precomputed data structure for these methods is computed with binding site sequences composed from the set {A C G T} or from the set {A C G T X } where X is the do not care condition, or the precomputed data structure may be computed with binding site sequences composed from a set which is itself a subset of a set of 16 symbols each of which match any of the members of a distinct one of the subsets of the set {A C G T} (or {ACGU} or {ACGTU}).

Part of this invention is a method of representing genes potentially affected by transcription factors comprising a data structure substantially equivalent to a directed graph where (a) at least one source node represents a DNA-binding protein identified as being bound to particular double-stranded DNA binding site sequences; and,(b) at least one target node represents a gene which is adjacent to a potential binding sequence for said protein. In this method, attributes may be added to at least some of the edges of the directed graph. In one embodiment, these attributes represent data comprising the transfer function between quantities of one or more DNA-binding proteins putatively bound to potential binding sequences and the expression level of one or more genes neighboring such potential binding sequences. In another embodiment the attributes represent data comprising transfer functions of order and position of DNA-binding proteins putatively bound to potential binding sequences for a given set of potential binding sequences neighboring a gene. In yet another embodiment, the attributes represent data comprising the optimal putative order and position of the corresponding DNA binding proteins at any given point in time. In a further embodiment, the attributes represent data comprising the activity on gene expression for each DNA-binding protein. The activity can be repressive, enhancing, or neutral. Repressive activity reduces gene expression, enhancing activity increases gene expression, and neutral activity has no perceptible effect on gene expression. A method for producing a directed graph containing a representation of a substantially entire network of transcriptional activation and repression by combining a multiplicity of smaller graphs produced by the above method is included.

In the above method, at least one structure comprising (a) a source node representing a gene; (b) a target node representing a protein arising from the translation of said gene; and, (c) a directed edge from (a) to (b) may be added. The protein may arise with or without post-translational modification. A method for producing a directed graph containing a representation of a substantially entire network of transcriptional activation and repression by combining a multiplicity of smaller graphs produced by the above method is included. The sequence of the gene which encodes the protein for which data has been obtained (for example a transcription factor) is useful here, since this gene by encoding a TF affects genes to which the TF binds).

Other structures may be added, for example a structure comprising (a) a source node representing a first protein;(b) a target node representing a second protein arising from a modification of said first protein; and,(c) a directed edge from (a) to (b). To this structure may be added another structure comprising (d) a source node representing a first protein; (e). a target node representing a second protein arising from a modification of said first protein; and, (f) a directed edge from (d) to (e). A method for producing a directed graph containing a representation of a substantially entire network of transcriptional activation and repression by combining a multiplicity of smaller graphs produced by the above method is included. Data from a fully sequenced organism is helpful in this context.

Part of this invention is a process for determining a correspondence between the expression levels of genes and binding of DNA-binding proteins to double-stranded DNA binding site sequences by (a) running essentially simultaneously from portions of the same first sample a first mRNA expression analysis and a first double-stranded DNA binding analysis; (b) running essentially simultaneously from portions of the same second sample a second mRNA expression analysis and a second double-stranded DNA binding analysis; (c) comparing the change in results between said first mRNA analyses and said second mRNA analyses to identify a set G of genes which have changed in their expression level; and, (d) comparing the change in results between said first double-stranded DNA analyses and said second double-stranded DNA analyses to identify a set B of binding sites which have changed in their level of binding.

To use this method for determining a correspondence between the expression levels of genes and potential genomic binding sites, the additional step of searching, in the promoter regions of each of the genes in set G, for each of the binding sites in set B, in order to create a mapping BG from individual binding sites in B and individual genes in G may be added. To use this method for determining a correspondence between transcription factors and genomic binding sites, these additional steps may be added, (f) data, comprising a correspondence between a set of transcription factors T and their binding sites, is consulted to create a mapping TB from individual transcription factor proteins and individual genomic binding sites; and,(g) combining, via common set B, map TB and map BG to create map TG of potential transcription factors responsible for control of gene expression. In these processes, the data of step f. is derived by assaying at least one purified protein using at least one library of double-stranded DNA probes, and at least one of said at least one library may comprise substantially all possible sequences of double-stranded DNA probes of length N.

Yet another method of this invention is a method for determining sequences containing the sequences of promoters of genes activated in a cell at a moment in time, by (a) contacting total mRNA isolated from the cell at the moment in time with a plurality of single-stranded total genomic nucleic acid probes, in solution or in an immobilized state on a solid support and determining from analysis of the plurality which genes of the cell are being expressed, (b) contacting the total protein population isolated from the cell at the moment in time with a plurality of double-stranded nucleic acid probes, which may be selected according to any criteria, but which preferably represent substantially all combinations of sequences of N base pairs in length or subsets thereof, determining from analysis of the plurality the double-stranded nucleic acid probes which have been bound by a DNA-binding protein from the total protein population of the cell, and c) determining the nucleic acid sequences of the bound double-stranded nucleic acid probes, and thereby obtaining sequences containing the sequences of promoters activated in a cell at the moment in time. The steps provided herein are for convenience but need not be performed in this sequence. For example step (b) may be performed before or after step (a). As can be seen for both this method and the related method described below, assays of this invention are used to perform step (b). The total protein population may be processed by conventional methods to remove extraneous materials or otherwise prepare the protein population for assay. Also, as stated above, the mRNA and protein population can be harvested from cells at any time and in any order and preserved for later use.

A related method is a method for comparing gene activation in a first cell and a second cell. The information obtained is useful for comparing and analyzing gene activation patterns in any context. It is possible to make multiple comparisons by carrying out this method on a number of cell populations, i.e. not just a first and second cell, but as many different cells as desired. The first and second cell populations may be differentiated by any one or more factors, for example the cells may be of different tissue types, may be engineered or natural, may be a healthy and diseased cell, may be the same cell type or state from different animals or family members or from different individuals, or from the same individual at different times, or healthy and diseased cells from the same individual, and the like. This method involves (a) contacting total mRNA isolated from a first cell with a plurality of single-stranded total genomic nucleic acid probes in solution or in an immobilized state on a solid support and determining from analysis of said plurality which genes of the cell are being expressed and contacting total mRNA isolated from a second cell with a plurality of single-stranded total genomic nucleic acid probes in solution or in an immobilized state on a solid support and determining from analysis of said plurality which genes of the cell are being expressed, (b) contacting the total protein population isolated from said first cell with a plurality of double-stranded nucleic acid probes which represent substantially all combinations of sequences of length N in solution or in an immobilized state on a solid support and determining from analysis of said plurality the double-stranded nucleic acid probes which have been bound by a DNA-binding protein from the total protein population of said first cell; and contacting the total protein population isolated from said second cell with a plurality of double-stranded nucleic acid probes which represent substantially all combinations of sequences of length N in solution or in an immobilized state on a solid support and determining from analysis of said plurality the double-stranded nucleic acid probes which have been bound by a DNA-binding protein from the total protein population of said second cell, (c) determining the nucleic acid sequences of the bound double-stranded nucleic acid probes for said first cell, and thereby obtaining sequences containing the sequences of promoters activated in said first cell and determining the nucleic acid sequences of the bound double-stranded nucleic acid probes for said second cell, and thereby obtaining sequences containing the sequences of promoters activated in said second cell; and(d) comparing the sequences obtained for said first cell with the sequences obtained for said second cell to determine gene activation in the first cell and in the second cell. Again, as stated above it is not necessary that the sequence of steps be as written here. Although (c) and (d) necessarily follow (a) and (b), these steps can be done in any order. In addition, "first" and "second" cell are used for convenience, clearly the order of obtaining and processing the mRNA and protein populations from the first cell and the second cell can be reversed without significance.

A further method of this invention is a method for obtaining a protein which binds to a specific double-stranded nucleic acid sequence by (a) providing a plurality of double-stranded nucleic acid probes which may be selected according to any criteria, but which preferably represent substantially all combinations of sequences of N base pairs in length or subsets thereof, in solution or in an immobilized state on a solid support, (b) contacting the double-stranded nucleic acid probes with a protein under conditions such that the protein binds to a specific double-stranded nucleic acid sequence of the plurality of double-stranded nucleic acid probes provided in step (a), and (c) separating the protein bound in step (b) from the specific double-stranded nucleic acid sequence to which the protein has bound in step (b) to obtain a protein which binds to a specific double-stranded nucleic acid sequence. Such isolation can be done by conventional methods. In particular, if the probes are on beads, then the nucleic acids can be cleaved off the beads by known methods, then run on denaturing gels to separate the bound probes (see for example Molina 2001 Nucleic Acids Research 29:479-487).

Another method of this invention is a method for obtaining a sequence containing the sequence of the promoter to which a transcription factor binds by (a) providing a plurality of double-stranded nucleic acid probes, which may be selected according to any criteria, but which preferably represent substantially all combinations of sequences of N base pairs in length or subsets thereof, in solution or in an immobilized state on a solid support, (b) contacting the double-stranded nucleic acid probes with a transcription factor under conditions such that the transcription factor binds to a specific immobilized double-stranded nucleic acid sequence of the plurality of double-stranded nucleic acid probes provided in step (a); and (c) determining the specific double-stranded nucleic acid sequence to which the transcription factor has bound in step (b), thus obtaining a sequence containing the sequence of the promoter to which the transcription factor binds. Examples of solid supports are arrays or beads.

Preferably, the double-stranded nucleic acid probes represent all possible three base pair sequences to all possible ten base pair sequences, more preferably all possible four base pair sequence to all possible eight base pair sequences.

Also part of this invention is a method for determining that a protein is a double-stranded DNA-binding protein by (a) providing a plurality of double-stranded nucleic acid probes, which may be selected according to any criteria, but which preferably represent substantially all combinations of sequences of N base pairs in length or subsets thereof, either in solution or immobilized on a solid support, (b) contacting the double-stranded nucleic acid probes with the protein under which DNA-binding proteins bind to double-stranded nucleic acid, and (c) determining whether the protein has bound to a double-stranded nucleic acid sequence, thus determining that the protein is a double-stranded DNA binding protein.

Also part of this invention is a method for determining whether two double-stranded nucleic acid-binding proteins bind to the same binding sites which comprises: (a) providing a first plurality of double-stranded nucleic acid probes, which may be selected according to any criteria, but which preferably represent substantially all combinations of sequences of N base pairs in length or subsets thereof, in solution or immobilized on a solid support, (b) contacting the first plurality of double-stranded nucleic acid probes with the first protein under conditions appropriate for binding, (c) providing a second plurality of double-stranded nucleic acid probes which may be selected according to any criteria, but which preferably represent substantially all combinations of sequences of N base pairs in length or subsets thereof, in solution or immobilized on a solid support, (d) contacting the second plurality of immobilized double-stranded nucleic acid probes with the second protein under conditions appropriate for binding, (e) determining the sequences of the probes to which the first and second proteins have bound, (f) narrowing the binding sites for each protein by analysis of the probe sequences, and (g) determining whether the two proteins bind to the same binding site by determining whether the two proteins have bound to the same subsequences of any bound probes.

Also part of this invention are active compounds isolated as a result of the assays and methods disclosed herein. The active compounds of this invention are capable of modulating gene expression. These compounds include DNA-binding proteins isolated as described above, and active compounds developed from elucidation of the functional domains of these proteins. Examples of such compounds are antagonists and agonists of the activity of the parent protein.

In more detail, this invention uses existing microarray technology in a different way than is currently used. Conventional microarray techniques start with single- or denatured double-stranded DNA probes on an array, and hybridize denatured cDNA derived from cells. In contrast to conventional uses of microarrays, we use arrays of double-stranded DNA probes under normal nuclear cellular conditions, incubate them with putative DNA binding proteins and measure probe binding. While conventional approaches to using microarrays attempt to measure gene expression level (specifically by measuring mRNA) instead we use them to take a snapshot of bound transcription factors.

Proteins bound to the double-stranded probes on the microarray can be measured using a variety of methods such as fluorescence, radioactive labeling or combinations with labeled competitive non-sequence specific factors. These bound proteins are presumed to be transcription factors— simply due to the fact that they specifically bind to DNA. In addition, they will only bind to sequences that they are specifically targeted for. By carefully selecting known probe sequences for the microarray, very specific sequence information for these transcription factors can be deduced.

For example, if we take a single transcription factor that is known to bind to the double-stranded DNA sequence:

$$5'-GATT-3'$$
$$3'-CTAA-5'$$

and we incubate it with a microarray containing all 4096 possible 6 base-pair sequences, then we would expect it to bind to 48 out of the 4096 sequences where this sequence appears. There is really only one recognition sequence that will show this pattern of binding (and its reverse complement which may result in 96 binding sites)—an unknown transcription factor which binds to another 4 base-pair recognition sequences will show a different pattern of 48 binding sites.

This example is not completely realistic because in order to be effective and targeted, transcription factors are presumably more specific than 4 base pairs. Typically, they are found to target 6-7 base pairs as a recognition site. In other words, we would probably scale this to a higher number of base pairs, and the number of bindings would be fewer and more specific (e.g. a 6 bp recognition sequence on a 6 bp array would have exactly one binding site). However, this simple example illustrates the method.

Given a recognition sequence for a given transcription factor allows us to search for this sequence in the genome of the organism under study. If the sequence is long enough, we can use it as a primer sequence in a PCR amplification experiment. That is, we can try and amplify the DNA adjacent to this sequence. It may result in several amplified sequences if the original transcription factor binds to many genes so that they are all expressed in a coordinated manner. This amplified DNA can be sequenced to determine the genes that are possibly affected by the transcription factor.

If the organism has had its genome completely sequenced, we can perform much more rapid and reliable searches using a genome database by searching for the expression pattern in genes which are adjacent to these sequences.

Searching using either of these methods allows us to find regulatory regions that may be used by the organism for enhancing or suppressing the expression of the nearby gene. Further classical genetic confirmatory tests can be performed to confirm the regulatory relationship.

Benefits of this method are as follows:

This is a direct (forward) method to determine promoter sites directly from transcription factors without a detailed knowledge of the protein structure, and without trying to use mRNA data to go (backwards) to find the promoter regions. Those other methods still won't find the transcription factors. Candidate transcription factors can even be synthesized from genes so that both the transcription factor sequence and the genes it controls can be known. In turn, those genes may be synthesized and the process repeated until the regulatory network has been determined (pathway walking).

Computer searches for these sequences can be performed in the regulatory regions of substantially sequenced organisms.

Regulatory regions tend to be short (<10 bp) sequences— sometimes separated by up to thousands of base pairs. Even within these regions, some of these bases may not be significant. Careful array design will allow determination of sensitive and insensitive bases even within this region. One such design involves arrays using all $4^{10}$ possible sequences. Analysis of the binding results will directly show sensitivity and specificity of the binding region. It will also show if the binding region is 10 bp long, or shorter. Realistically, $4^6$ is very practical (only 4096 probes) without using photo-lithographic techniques. Unfortunately, photo-lithographic techniques cannot synthesize double-stranded DNA, but techniques to convert these chips to double-stranded DNA have been discussed in the literature.

If the genome sequence is not known, regulatory regions that are identified can be used to pick genes out of a genomic DNA library or used as a PCR primer in a standard molecular biological approach. Genes so identified can then be expressed and run using this method, etc. It is arguable that by this repeated pathway walking, (vs. Genome walking) one can identify the small important part of eukaryotic genes that are actually expressed. This is a little like the cDNA approach to determining the important genes.

Frequently, a transcription factor may bind to a regulatory region, but may be indifferent to one or more of the bases in, say, a 6 base pair sequence. These would be characterized as don't-care bases in the sequence. This method can immediately report which sequences are important to the binding and which aren't. This is due to combinatorial analysis of the exhaustive sequences represented on the array.

Even if there are many transcription factors responsible for the expression of a given gene, one or more of them must recognize DNA alone or in a di-mer, tri-mer, tetra-mer or other form. Starting with the one that binds most tightly to the DNA (the innermost factor), the complex can be built in vitro. We can also identify competitive sequences that may be overlapping, or sequences that build upon other pre-bound sequences.

While it is clear that this method can be used to analyze a single transcription factor, it can also be first used at a gross genomic level by incubating unpurified cellular protein extracts to the array. Ideally, we would isolate just the transcription factors. However, part of the point is to determine which proteins are transcription factors. While the above-described single-factor process may be repeatedly applied to elucidate pathways one at a time, there are many scenarios one can image between this stepwise approach and the other extreme that uses all of the cellular extracts at once. Such genomic exposure may seem to clutter the analysis of each transcription factor, however, there are a number of benefits to this approach:

We will immediately determine sequences which are NOT regulatory regions—eliminating substantial parts of the genome that are not important to our discovery of real regulatory sites. This will help us focus more quickly on real regulatory sites.
  As mentioned, some transcription factors only work in tandem with others. This will allow us to discover if combinations of transcription factors bind to particular sites.
  We can perform top-down refinements of the transcription factor/gene relationships in a classical divide and conquer manner. For example, if the data analysis just mentioned results in too many potential binding sites, then the proteins can be semi-purified and tested again against the double-stranded array. With enough refinements, it will be possible to characterize precisely which fraction of purified proteins corresponds to which binding sites. For instance, the purification steps can be somewhat arbitrary and crude as long as they divide the proteins into 2 or more sub-groups that are then re-assayed and compared with the original whole group (The important thing is that the processes not irreversibly denature the proteins.) Any proteins not bound in one of the subgroups means that it required the help of a protein in the other subgroup, and a different fractionation method may be applied. The same protein will bind to the same site in each different fractionation.
  In one assay, all of the regulatory sequences can be determined for the given cell state. Importantly, this will include the negative regulatory sequences that are invisible to the mRNA analysis approach. Even in differential array analysis, the appropriate stimulus must be used to remove a repressor protein so that a different mRNA expression level can be seen. If the stimulus has no effect on the repressor protein then no expression level changes will be seen, so no related transcription factor can be found. Some repressors are always bound except in extreme conditions that may never be created for a given experiment. This assay will allow the detection of these constitutively bound repressors and their sites. As discussed, current computer methods to try and discover repressor regions using only mRNA expression data are very intractable.
  This method is very complementary to the classical mRNA approach, and the combination provides the most powerful method to define pathways. Using computer analysis methods, we can powerfully combine data on mRNA expression from these cells with transcription factor binding site data for these same cells. Ideally, one would take the same cell extracts, and use a portion for mRNA analysis and a portion for transcription binding analysis. The cellular extract from a cell culture can be split into mRNA and other proteins. Both classical microarray and this promoter finding analysis can be performed in parallel.
  If the organism has been fully sequenced, then once the mRNA expression levels are known, we generally can know the genomic regions corresponding to each expressed gene. A search for all discovered regulatory binding sites in the promoter regions of expressed genes would quickly converge to a unique solution of what regulatory regions are active on which genes.
  One can think of this as a forward and backward search method where we know that the common meeting point is each expressed gene. If we know the genomic gene sequences, then the mRNA must correspond to a gene, and the transcription factors must also correspond to one or more gene regulatory regions. The fact that the same set of genes must be found whether we take the mRNA expression levels and go backwards to the genes, or take the promoter sequences and go forwards to the genes allows us to rapidly converge on the active promoter regions for each gene. While it is possible for some ambiguity to remain (and there are the constitutive repressors to consider), this is orders of magnitude more tractable than mRNA-based promoter finding alone.
  This powerful combination significantly narrows the solution space of the regulatory network as well as creating directionality to the relationships. In other words, we can progress from a loose network of gene correlation to much tighter cause and effect relationships.
  This method allows for exploratory and reductionist approaches to focus on given pathways while classical microarray analysis remains very powerful but still statistical and inferential.
  Individual proteins (alone or in sets) may be synthesized and assayed in vitro to narrow the relationship between a given transcription factor and the regulatory regions it recognizes. In the classical microarray approach, there are many complex factors contributing to what is considered to be a form of experimental error. This is due to the fact that we cannot currently go into a cell and turn transcription factors on or off, and see what happens. Even in cases where we can approach this ability, we must know what we are looking for first, and it is very hard to use this as an exploratory method—when you don't know what you are looking for.
  To determine if a given gene is a transcription factor, and what it potentially regulates, one can simply synthesize the mRNA (e.g. using an in vitro or in vivo T7 promoter technique), incubate it with a microarray as described and see what probes it attaches to. Any probe that it attaches to must contain a sequence that this factor has an affinity for. Searching the full genome for these sequences will identify potential candidate genes that are directly or indirectly regulated by this gene's transcription factor product.

The final and intermediate results of this process may be useful in their own right, and it is not necessary to perform all steps of this process to get meaningful results. It will depend, in part, on what other experimental methods are being used.

For instance, this application contemplates the situation where one performs Phase 1 analysis without knowing the specific TFs which are in the solution in Step 1. The reason is that without even knowing the exact identity of the TF's allows one to usefully eliminate potential binding sites which may have previously been assumed to function in gene regulation.

In another situation, one might take TF's from one organism or cell type, obtain the Phase 1 output, and then take TF's from another organism or cell type, obtain the Phase 1 output from that experiment, and compare the two. This can then be extended to experiments where more than one such set of TF's are being used.

In another situation, where one might start with a large pool of TFs, and one wants to narrow the set of TF's to determine which specific TFs bind to which specific DNA sequences, one might purify or fractionate, (using any number of appropriate well-known chemical purification techniques) the original Step 1 solution into separate pools, and repeat Step 1 for each of these fractions. The difference in the output of Phase 1 for each such pool vs. each other pool and the original will be indicative of the set of sequences which are bound to by the TFs in the original and each fraction. This may be repeated until solutions are at the desired purity to determine the desired TF to Sequence correspondences.

Note that in this analysis, there will be cases where the combined sequences in a sub-pool do not correspond to sequences in the immediately prior pool. This is indicative of potential interactions between components in each pool which may be required to form the TF shown in the original pool. In the extreme, if the original is purified down to, say, single protein molecule types, but such proteins must form a hetero-dimmer with another protein in order to act as a TF, then there will be no binding shown for the individual proteins. This information can be used as evidence of the dimerization between proteins in different pools.

Similarly, there are known cases where one protein acts to inhibit DNA binding of another protein. A case exists whereby a TF in a sub-pool is shown to bind to a DNA sequence when this was not the case when this pool was in an original or combined form with other pools. This would be indicative of an inhibitor or repressor molecule.

Note again, that TF's and their associated inhibitors or co-factors are frequently proteins, but not necessarily so, and they may also have been subject to a post-translational modification.

EXAMPLES AND DISCUSSION

The methods required to perform the assays and analysis described above are conventional in the relevant arts, and are described in the references cited herein. In addition, the material provided below gives more detailed instances and examples for the subject matter described herein.

The invention uses diverse oligonucleotide sequences as an assay to probe for target molecules that bind to the probes. In one embodiment of the assay, the invention provides arrays of spatially restricted probes. In another embodiment, the probes are attached to a bead that overcomes some of the limitations of a two-dimensional binding surface while allowing pseudo-solution phase interactions with targets. In yet another embodiment, the probes are free to move about in solution.

Synthetically generated nucleic acid sequences are widely available commercially, and methods of synthesizing desired single stranded DNA sequences are well known to those of skill in the art. Methods of forming large arrays of spatially restricted (e.g. on a planar surface) single-stranded and double-stranded oligonucleotides have been described in the literature, and in particular, by Pirrung et al. in U.S. Pat. No. 5,143,854; Fodor et al., *Science*, 251:767-777 (1991); and Lockhart et al. U.S. Pat. No. 5,556,752, Bulyk, M. et al., *Nature Biotechnology* 17: 573-577 (1999), which are incorporated herein by reference.

Methods of synthesis of single-stranded and double-stranded DNA combinatorial libraries that may be used for assays of the current invention are well covered in the literature. While the beads have not been widely used for dsDNA binding assays, details on the in situ synthesis of oligonucleotide probes on beaded solid supports is described in U.S. Pat. No. 5,846,719 (Brenner et al.); U.S. Pat. No. 6,013,445 (Albrecht et al.); U.S. Pat. No. 5,604,097 (Brenner); Needels, M. C. et al. *PNAS* 90: 10700-10704 (1993); Brenner S. et al., *PNAS* 97:1665-1670 (2000); and Brenner S. et al. *Nature Biotechnology* 18: 630-634 (2000) which are incorporated herein by reference.

In microarray nucleotide binding assays that use a planar configuration of bound probes, knowledge of the spatial location of each probe's sequence allows mapping of binding site back to the particular probe sequence at the binding location, and becomes the read-out of the binding affinity for that sequence. Methods of measuring binding of targets to probes for the microarray planar format has been described by Lockhart et al. U.S. Pat. No. 5,556,752 and Bulyk, et al., 1999 Nature Biotechnology 17: 573-577.

In assays that use either a plurality of beads each with no more than one type of probe sequence, the bound sequence must be determined after the binding event by purifying or sorting the bound beads. At the time of synthesis, beads may be marked with an identifying tag (unique coded molecules or chromophores for example) that is unique to the particular oligonucleotide or probe that is present on each bead. Upon binding detection, the bead's unique molecular tag is read in order to map the binding data back to the specific probe sequence on the bead. Alternative implementations cleave the oligonucleotides probes from bound beads, and then amplify and identify the sequences found.

In assays that use oligonucleotides in solution that are not on a solid support, the bound oligonucleotides must be read after the binding event by purifying the bound probes, and then sequencing or reading a tag on the probes so bound. Methods for determining sequences of bound probes in solution have been described by Pollock, R. and Treisman, R, Nucleic Acids Research, 18: 6197-6204 (1990) and Carey et al., Transcriptional Regulation in Eukaryotes, 2000.

In general, methods for generating single stranded DNA probes may be extended to double-stranded probes by the incorporation of a short constant sequence (typically 10-20 bases long) on the 3' end of all of the single-stranded probes. A primer which is complementary to this constant region is then used to start a polymerase-based in vitro primer extension reaction with free nucleotides and other buffer components in order to convert all single stranded probes into double-stranded probes. Primer extension reactions are well described in the literature, and is the basis for the Polymerase Chain Reaction (PCR) and Sanger Sequencing, and numerous other everyday techniques practiced by those versed in the state of the art in molecular biology. In specific, Bulyk, M. et al., Nature Biotechnology 17: 573-577 (1999) describe a primer extension method for making double-stranded DNA (dsDNA) from single-stranded DNA (ss-DNA) microarray chips from Affymetrix, Inc. (Affymetrix, Inc., Santa Clara, Calif.).

Like most technologies developed for detection of cDNA transcript abundance, Brenner et al. seem to primarily use the beads in a ssDNA probe format. However, there are many intermediate steps in their assays in which the probes do become dsDNA. In addition, others in the field have created dsDNA probes from ssDNA probes in much the same way as Bulyk et al., for example see Molina, D. et al, Nucleic Acids Research 29: 479-487 (2001) and Needels, M. C. et al. PNAS 90: 10700-10704 (1993).

Libraries of diverse nucleic acid sequences may be used as probes, for example, in screening studies for determination of binding affinity exhibited by nucleic acid binding proteins, drugs, or RNA. One aspect of the present invention involves discovery of transcription factor identities and functionality. For example, problems in the normal functionality of the p53 transcription factor in humans have been implicated in many forms of cancer. Understanding transcriptional regulation of genes is a key piece of the overall regulatory network found in living cells and organisms.

Libraries on a Single Substrate

Light-directed Methods

Flexible linking molecules such as polyethylene glycol can be incorporated in the place of nucleic acids when a linker segment is desired in the probe. Such molecules will typically having an activating group (i.e., a phosphoramidite) on one end and for planar arrays, a photolabile protecting group attached to the other end as describe in U.S. Pat. No. 5,556,752. General methods of attaching molecular probes to solid supports is discussed in detail in texts such as Hermanson et al., Immobilized Affinity Ligand Techniques (1992), that is incorporated herein by reference for all purposes. Examples of photolabile protecting groups include NVOC or MeNPOC, and examples of chemical labile protecting groups include FMOC and DMT. For more details, see Greene, et al., Protective Groups In Organic Chemistry, 2nd Ed., John Wiley & Sons, New York, N.Y., 1991, incorporated herein by reference.

The methods for focusing binding sites from Gross Binding Site Data can account for the presence of oligonucleotides that may be used as linker segments for mechanical purposes. These focusing methods work for this purpose because they essentially simulate binding conditions, which include all binding sites including the linker segments. Therefore, oligonucleotides of known (or knowable) sequences can be used for such purposes if the method for binding site focusing (described herein) is used to process the Gross Binding Site Data obtained from a nucleotide probe binding assay.

Methods of Library Screening

A library prepared according to any of the methods described above can be used to screen for targets having high affinity for specific sequences of oligonucleotides. Targets may be purified molecular species such as known transcription factors or complexes where the species are known to bind oligonucleotides, however, the exact binding sequence or set of sequences is unknown. Alternatively, potential targets may be part of a mixture, and the assay is being used not only to determine any probe binding activity, but if any is found, what are the specific probe sequences being bound by the target or targets in the mix. For example, in cell lysates, there may be hundreds or thousands of DNA binding proteins, and for these, a binding site assay will have the combined effects of all of the target molecules.

Some proteins are non-specifically binding, and are frequently not of interest in these assays. One skilled in the art will typically use non-specific competitors to the probes to effectively titrate-out the non-specific targets. For gel shift assays, for example, poly dIdC nucleotide sequences are sometimes used to reduce non-specific DNA binding. To reduce overall non-specific binding in planar or bead arrays, frequently Bovine Serum Albumin (BSA) is used (See Sambrook et al., Molecular Cloning, 2001 Ausubel et al., Short protocols in molecular biology, 4$^{th}$ Ed., 1999, and Carey et al., Transcriptional Regulation in Eukaryotes, 2000.)

For some assays, it will be possible to label the targets. Suitable labels include, but are not limited to, radiolabels, chromophores, fluorophores, chemiluminescent moieties and transition metals. It may be possible to generate the target with the label if, for instance, targets are being synthesized through a tagged fusion protein method that is known not to affect their binding activity.

Alternatively, they may be recognizable by an established antibody if the identity is known, and an antibody for that target exists. Numerous ways are described in the literature to detect the antibody that has in turn detected the presence of a target that is bound to a probe (See E. Harlow et al., 1999). Unknown proteins may be labeled from cell lysate if it is possible to grow the culture under conditions that incorporate radioactive amino acids in the cell's peptides.

In order to screen the targets with the library, generally, a solution containing labeled targets is introduced to the library and incubated for a suitable period of time. The library is then washed free of unbound targets and the probes or double-stranded oligonucleotides having high affinity for the receptor are identified by identifying those regions on the surface of the library where labels are located.

If a planar microarray format is used, radioactivity as a measure of binding strength may be assayed using phosphorimagers or autoradiography to identify radiolabeled targets bound to specific probes. Fluorescent markers are detectable by fluorescence microscopy or laser scanning, or in the cases of beads, flow cytometry can be used for bead sorting. Other techniques to obtain binding assay results will be readily apparent to those skilled in the art.

An alternate to techniques that require labeling the targets or having an antibody to the targets is to use a competitive binding assay method. In this method, a labeled competitor that has an affinity for the type of nucleotide probes being used in a non-sequence specific manner. While this is a well-established biochemical technique, use of the method in this context is novel because most researchers have been searching for DNA-binding proteins using a non-exhaustive library approach.

The use of a library with substantially all the probes of length N with a non-sequence-specific dye competitor (such as Hoechst 33258, Ethidium Bromide, Methylene Blue, DAPI, or SYBR Green/Gold (Molecular Probes, Inc, Eugene, Oreg.)) allows the immediate determination of the bound library sequences. By subtracting the set of labeled sequences from the complete set of sequences one arrives at the set of bound sequences. Strength of binding may also be determined by inverting of the measured labeled binding affinity. Measurement of the competitor should be done in conditions that favor target binding over competitor binding to allow targets with low probe affinity to bind. The precise conditions for performing these steps will be apparent to one skilled in the art.

The principle advantage of competitive labeling is that there is no need to label DNA binding proteins which in many cases are either completely unknown, would require fusion protein labeling using time-consuming recombinant DNA techniques or would alter the affinity of the molecule for the probes. Finally, in many cases, the targets may be activated by subtle mechanisms in vivo. One of the objects of this invention is to enable the discovery of what these activation mechanisms might be, and what the circumstances are under which they occur. Labeling of naturally occurring transcription factors by any method (with the possible exception of radiolabeling which also has disadvantages) is likely to be invasive by definition.

Finally, nucleic acid probe/target binding measurement may be performed by methods based on Surface Plasmon Resonance developed by (Biacore International AB, Sweden).

Method for Determining DNA Binding Sequence(s) Given a Plurality of Probe Sequences, and Qualitative or Quantitative Binding Information:

Limitations in microscopy and the tedium and inexactitude of some other methods has led to determination of specific binding sequences by one or more DNA Binding Proteins ("DBP's") using other methods. A number of companies and researchers are using single-stranded DNA probes bonded to microscopic styrene beads as a way to detect gene expression in different cellular populations (For example, U.S. Pat. Nos. 5,604,097 and 5,846,719). As in classical microarray technology on planar solid supports, the differences in cDNA or mRNA are measured by detecting differences in hybridization to the single stranded probe population. Typically, the probes have been purified, or are synthesized in situ via chemical or photo-chemical methods (U.S. Pat. No. 5,556,752).

Gross information about which dsDNA probe sequences that have been bound can be determined by a number of methods including:

1. Modifications to standard microarrays to make them double stranded before using them to detect binding of transcription factors (see Bulyk et al. 1999 Nature Biotechnology 17:573-577), incubating with a liquid phase possibly containing transcription factors and then detecting binding using methods described herein;
2. Modifications to single stranded beaded combinatorial libraries (see U.S. Pat. No. 5,846,719) to make them double stranded before using them to detect binding of transcription factors, incubating with a liquid phase possibly containing transcription factors and then detecting binding using methods described herein;
3. Methods described herein to determine DNA-specific binding using double stranded DNA in solution that:
   a. contain substantially all possible sequences of random DNA of a certain length or
   b. certain probes with some mutations in competition with the probes such as a promoter region from a gene and mutations thereof; or
   c. contain random DNA sequences enriched using the modified PCR method described by Pollack and Treisman in Nucleic Acids Research 18:6197-6204, 1990.
4. followed by sequencing unknown probes by:
   a. generating a classical plasmid library with these sequences ligated into them, transfecting in *E. coli* and sequencing them, or
   b. using the iterated Sanger sequencing method described herein.

Methods of Identifying Array Binding Sites

Method 1: A single purified protein or protein complex may be tested for dsDNA binding using any of the described methods for doing so. Then, the subsequence binding information can be determined from the sequence and binding information using an algorithm such as that described above. This allows the mapping of an activated transcription factor (TF) or DNA-bindng protein (DBP) to one or more specific sequences. This is a vast improvement over foot-printing analysis that is the current state of the art way to determine DNA binding sequences. Not only is the footprint method tedious and time consuming, it also depends on an educated guess to determine the sequence unless all possible sequences are to be tested which, as a practical matter, is not done. Furthermore, subsequence specificity is not generally found using this method because a DNA degradation enzyme must be able to penetrate the binding site at 'don't care' bases. While this may mean that the protein is not tightly bound at this point, it still may not allow access of the DNA degradation enzyme to see this.

Method 2: An undetermined mixture of proteins (typically cellular extract with an inhibitor for DNAase) that may include some DBP's is assayed as in Method 1, however, in this case, we will end up with a number of subsequences which represent all of the possible binding sites of the set of proteins in the mix. This may be used in further experiments on fractions of the original mix to determine which subsequences were bound by which fraction.

Method 3: Using the approach of Method 2, one can obtain different sets of subsequences depending upon, for example, different cell types or cell culture treatment conditions. Subsequences found in the first experiment, but not in the second experiment are candidate cis-elements which were actively bound by a DBP in the first set of cells, and not in the second. The reverse is also true.

Method 4: Using the approach of Method 3, one can simultaneously assay for gene expression using mRNA transcript detection assays (ideally using single stranded microarrays [e.g. U.S. Pat. No. 5,556,752, Schena, et al. 1995 Science 270:467-470; Shalon et al. 1996 Genome Research 6:639-645) or alternatively Northern Blots, dot blots, or RT-PCR [see Roche Lightcycler, manufacturer's information]) starting with the same cell lysates from each experimental condition. By coupling differences in candidate cis-elements with differences in gene expression level by using mRNA analysis and comparing the gene expression levels in each experiment, one can infer that the cis-elements identified may effect the observed changes in gene expression levels within the normal tolerance of experimental error. In particular, if one has already performed Method 1 analysis for substantially all of the organism's activated DBP's, then one can draw conclusions about which of the DBP's may be absent or present under the various experimental conditions, and therefore which genes it is regulating.

Note that there are other factors which can influence gene expression levels, including: histone modifications, the modification of non-DNA binding proteins or domains of DNA binding proteins that can activate or suppress transcription, DNA methylation, and other epigenetic effects such as gene silencing.

Method 5: Using Method 4, it is not always clear if genes expressed differently between the two conditions are directly or indirectly affected by the DBP's targeting the candidate cis-elements. That is, some genes are so called 'early response' genes because they are expressed first in response to a changing condition. These early response genes may in-turn affect other gene expression levels via DBP's or other methods as indicated above. This may be partially resolved using a time course experiment with many sampling time points, however, this is not always possible such as in comparisons between different cell types. Another way to disambiguate the DBP's directly affecting particular genes is through the use of genomic sequence information. That is, if the promoter or enhancer region of genes which are up or down regulated contain the candidate cis-elements of the difference set, then it gives strong support to the direct effect of a DBP on the expression of a gene. The promoter or enhancer region sequence for a given gene may be obtained by (a) database search if the sequence has already been determined, (b) PCR amplification then sequencing of the neighborhood of the coding part of the gene. Alternatively to (b), one may begin with a candidate cis-element sequence and use PCR amplification then sequencing of the neighborhood to identify genes that may be affected by the cis-element. In either case, some chromosome walking may be required to locate and sequence all of the sequence information required for this analysis.

The table below shows a possible interpretation of the combined DBP and mRNA expression data sets.

For each cis-element identified as new to this experimental condition, and each set of genes with altered expression containing the cis-element in their promoter region, the following table illustrates some of the possible hypotheses (indicated by H:) arising from each combination of a given cis-element and genes whose expression level have changed.

| Changes in cis-element binding identified by Method 4 | Expression levels of genes containing this cis-element in their promoter/enhancer region are ... | | Expression levels of genes not containing this cis-element in their promoter/enhancer region are ... |
|---|---|---|---|
| | up-regulated | down-regulated | either up- or down-regulated |
| The cis-element is now bound. | H: DBP bound to the cis element is an activator | H: DBP bound to the cis element is a repressor | H: Changes in gene expression level are due to (i) cis-elements other than this one, (ii) changes other than changes in DNA binding affinity such as changes in activation domain, (iii) changes to other proteins in the transcriptional complex, (iv) epigenetic affects, biological or experimental noise or (v) other explanations. |
| The cis-element is no longer bound. | H: DBP bound to the cis element was a repressor | H: DBP bound to the cis element was an activator | |

Based on numerous studies on in vivo transcriptional activation, it is clear that the overall recognition of the promoter and enhancer regions (hereinafter just called promoter region to mean both) by sets of proteins is crucial to gene expression of proximal genes. The recognition of certain parts of the promoter region is based upon the composition of the proteins that are collectively part of the transcriptional complex. In any given complex, different proteins within the complex may bind to different DNA sequences within the promoter region. Stretches of the promoter region ranging from a single base long up through thousands of bases long may either be unbound by the complex, or may be bound but in a way not specific to the identity of the particular nucleotide(s) in those stretches.

When the complexes are broken down using various experimental techniques, it has been shown that some factors in the complex contain DNA binding portions, and some do not. There are cases where the DNA-binding of a particular isolated species changes its affinity (and theoretically can also change its specificity) based on the cooperative effects of another species within the complex. In this way, the most specific and highest affinity for the DNA sequences may be achieved only by combinations of factors in a complex. However, most of what is now known about nature's transcriptional activation machinery was learned though the isolation of specific DNA binding proteins (i.e. Transcription Factors) in isolation in vitro.

It is clear from these studies that occasionally, the equilibrium of individual factor binding must be shifted to the right somewhat in order to see the DNA-Protein binding effects in vitro. Gel shift assays are thought to cause a partially dehydrated caged environment which effectively shifts the equilibrium constant of the binding reaction towards the bound state.

In the assays to determine the specificity of single or individual factor binding there may be conditions that need to be changed in order to shift this equilibrium to the bound state in order to practically detect transcription factor binding activity.

In an ideal situation, the detection technology will be sensitive enough to detect DNA binding of proteins in conditions that most closely approximate the natural conditions in which the genomic DNA finds itself in a cell. In vitro conditions will naturally be different than cellular conditions, however, many researchers have found workable buffer and hybridization conditions which work well empirically. These include conditions used for gel retardation assays designed to optimize TF-DNA binding and these conditions will work for these assays as well.

Depending upon the sensitivity of the detection methods (radioactive, fluorescent, Surface Plasmon Resonance (SPR) or other), in order to improve the readout signal of the assay, the affinity of proteins for their DNA binding targets may be increased by one skilled in the art of molecular biology by changing buffering and hybridization conditions. Such changes may involve increasing concentration of the proteins in hybridization solution, changing the salt content or pH of the reaction, and adding effective dehydrating agents such as polyethylene glycol (PEG), dextran sulfate or agarose. Some or all of these methods may help to produce a better signal, however, these are not meant to imply that they are necessary steps. Again the preferred embodiment achieves the desired read-out of DNA-Protein interactions through the use of buffered conditions which approximate nature, and a sensitive measurement assay to determine which probes are bound.

Cooperative binding effects could potentially be utilized, and be improved if probes that closely mimic those in nature could be used. For instance, if a collection of 2000 bp probes were used to test for hybridization, with TF's, then the cooperative binding effects of complexes would improve the sensitivity of the assay.

As this invention is not limited in either the size of probes or any requirement that they be the same length, there are two additional improvements to any dsDNA probe technique (those now in existence as well as those proposed herein) which are a direct result of this ability.

Solution-based Footprinting

Another preferred embodiment of this aspect of the invention is to synthesize random DNA fragments that represent substantially all dsDNA sequences of length N. Allowing these fragments to bind in solution by incubating an excess quantity of them with cell lysates or expected TFs.

Binding of random fragments may be driven in the direction of association by providing the fragments in large excess. Known non-denaturing protein purification steps such as gel electrophoresis can be used to resolve proteins into complexes bound to DNA. The complexes are then isolated individually, the bound DNA can be liberated from the proteins under denaturing conditions (such as SDS-PAGE) and the previously bound DNA sequence and each protein component can be identified.

For example, the random probes may be end-labeled with a fluorescent tag (such as cy5) or radioactively labeled by incorporating radioactive nucleotides in the original synthesis, by known methods. This labeling allows auto-radiography, phosphorimaging, or fluorescent detection of DNA associated protein complexes which may then be further cut out of a gel, or fractionated for further identification of the components as described in general above.

Alternatively, the first separation step is performed after a prior fractionation step using ultracentrifugation with each of the fractions being run in separate lanes.

In another example, the first separation step is performed after a purification step to remove the free DNA fragments that may be performed using a non-denaturing gel or other methods, and followed by an enrichment step using co-precipitating DNA-bound proteins using a DNA affinity column. This affinity column can be designed using (a) a bound poly-nucleotide which is known to hybridize to a constant region of all the DNA fragments; (b) another tag on all the original fragments which may be selected using affinity chromatography (e.g. biotin with a cleavable streptavidin); or (c) a non-specific DNA binding molecule on the column. Further purification of this reduced set of protein complexes and their bound DNA can then be performed as described above or by other preferred embodiments.

Or the first separation step may be performed directly without a prior fractionation step in conditions identical to those known for Gel Retardation assays. In this case, however, free DNA is allowed to run off the end of the gel, or is ignored, and bound complexes can be seen because they are marked. Free DNA may be detected in this case by using a control lane with a sample of the original random fragment population.

Alternatively, the DNA fragments are end-labeled, but not labeled in the middle. After purification of protein-DNA complexes, the DNA can be purified, and because the DNA is already end-labeled, it can be directly sequenced using the Maxim-Gilbert chemical degradation sequencing method.

In many cases, there will not be sufficient quantities of DNA after the first purification reaction, in which case, an amplification step may be required. To facilitate this amplification step, the original random probe set can contain uniform primer sequences on each end that can be used for a PCR to amplify any DNA fragments that were bound to proteins using. Such amplified DNA will be in populations specific to a complex, but they might be a mixed population of sequences depending on the sequence specificity of the protein complex that bound to them. If the DNA is unambiguously sequenced, then only one sequence bound. Sequences may be determined for all of the members of this sub-population as described below (Iterated Sanger Sequencing) for sequencing mixed populations of DNA fragments.

In another embodiment, one may obtain the genome-wide (or aggregate) promoter 'footprint' by determining the sequences of all bound fragments and then using the sub-population sequencing method (or an alternative sequencing strategy). The genome-wide or aggregate footprint method would be performed after incubation of the random populations of fragments with the cell lysates or other source containing DNA-binding proteins. The first step is to purify the mixture by removing any non-bound DNA fragments that may confound later analysis. This can be done by using: (a) a size fractionation column which allows the small unbound DNA fragments to preferentially pass-through followed by elution of proteins; (b) non-denaturing gel electrophoresis allowing all fast migrating unbound DNA separate away from the protein and protein bound-DNA components; or (c) by ultracentrifugation and removal of the DNA-only fractions. Next, the remaining DNA and protein mix is separated into purified DNA that had been protein-bound. This can be done by using standard DNA purification methods such as Phenol:Chloroform extraction and further standard methods of DNA purification known to those versed in the state of the art. Next, the resulting fragments can be optionally amplified (if there is not sufficient quantity to resolve them by using PCR or other amplification methods). Next, the sub-populations are sequenced as described below or using other methods. Finally, the sequences may be searched for a total set of footprints using the computer algorithms described herein, or proprietary or freely available alignment programs.

Variable length sequences can be used with the above, and even the primer regions outside the probe region can be automatically included in the binding site focusing program described herein.

Promoter Site Mutagenesis Footprinting

Identification of the transcription factors that bind to a particular promoter region may be done experimentally as follows:

1. Use the promoter region (500-2,000 bp) DNA fragment for a gene of interest in a gel shift assay with cellular extract (Ausubel et al, Supra, and its references for details on Gel Shift assays).
2. Make random or systematic mutations in base pairs along the DNA, and perform this same experiment with a population of such mutated DNA fragments (See FIGS. 22A-C).
3. Perform a gross DNA sequence of the bound probes and the original population of mutant probes. Degenerate sequences are expected throughout the original set if mutagenesis was performed properly. However, among the probes what were bound as part of the shifted band, degenerate sequences are expected only in non-binding regions (See FIG. 23C).

If such an assay is done using cell lysate, the band of interest containing the factors, and both the original promoter and all variants that bind will be located in the same shifted band of the gel because they are the same length.

DNA probes may be separated from the bound complexes using a standard phenol-chloroform extraction. Identification of the bound transcription factors may be determined using standard methods by extracting the complex from the gel shift and subjecting it to MALDI-TOF or Edmund Degradation protein sequence analysis (See Schevchenko, A. et al. *Anal. Chem.* 68: 850-858, 1996)

A single promoter region (typically 2000 bp or less) can be mildly point mutated with approximately or exactly equal probability at each of its positions and in a manner such that such mutated fragments are substantially all the same length (See Sambrook et al., Supra for methods of mutagenesis, preferably using PCR-based methods). A population of such mutated sequences can then be incubated with a solution thought to contain transcription factors for that promoter region. After the above analysis of bound DNA sequences, and purification as described above, a straightforward analysis of sensitivity of each position of the promoter region to transcription factors can be obtained by aligning all bound fragments which differ in only a few base pairs each, and determining the most conserved regions amongst this population of fragments. Multiple sequence alignment is easily performed using many readily available software packages such as the program known as Clustal.

Figure 23A:
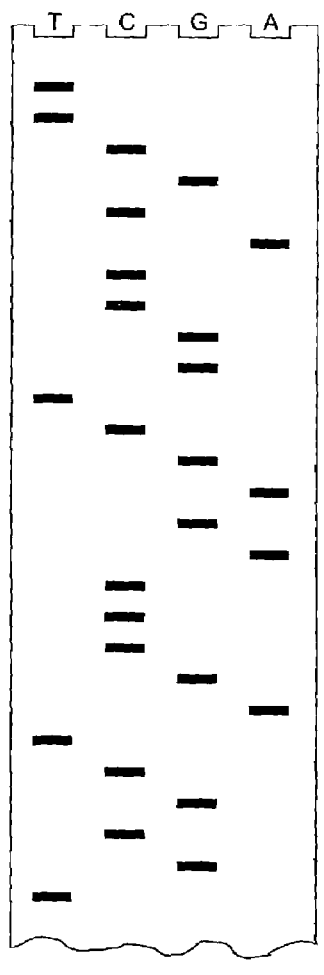
FIGS. 23A, 23B and 23C: Hypothetical sequencing gel schematics for footprint analysis
Figure 23B:
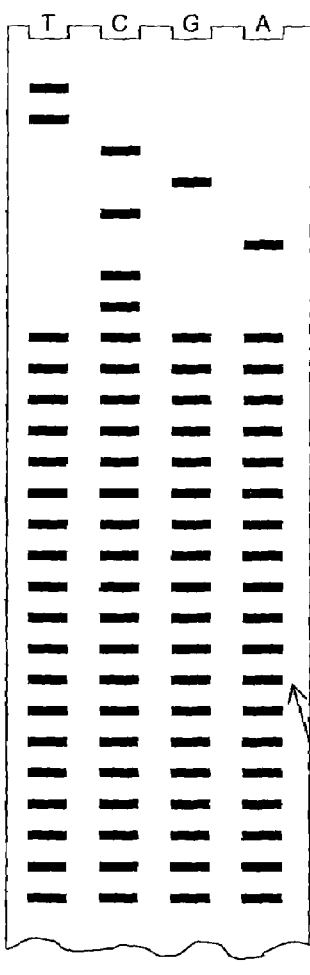
Figure 23C:
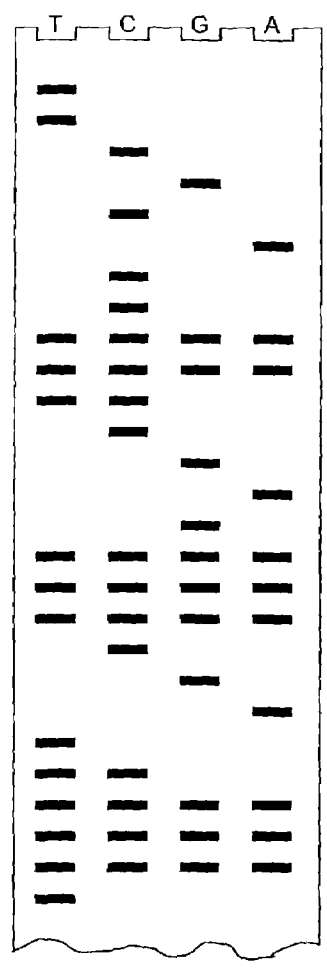

See FIGS. 22A-C showing use of the promoter mutation technique using PCR primers and creation of a plurality of probes which have mutations within the promoter region. See FIGS. 23A-C for a schematic view of what sequencing gels would look like for each stage of a random probe experiment. FIG. 23A shows a known probe, and FIG. 23B shows a plurality of probes such as one would see with the promoter method or the sequences of length N method described previously, and FIG. 23C shows the foot print of the DNA-Binding factor after purification of the bound probes.

Method of Genomic Discovery

Method for Mapping Binding Sites to Relevant Gene Promoter Regions.

A significant challenge in molecular biology today is the determination of the transcriptional control mechanisms that may be employed by a particular gene in a particular organism. A very large number of transcription factors in any given organism change their control of gene expression for nearby genes by changing their binding affinity for the promoter region of such controlled genes. There are also other control mechanisms involving other changes to the transcriptional machinery that may not directly involve changes in DNA binding such as changes in the activating domain of a transcription factor. For example, in the well known Galactose metabolic genes in yeast, the Gal4 transcription factor normally promotes expression of the Gal1 gene by binding to the Gal4 affects gene expression by binding to the $UAS_G$ binding site on the Gal1 gene in inducing its expression. However, upon binding by the Gal80 repressor, the activating domain of the Gal4 protein is silenced while the Gal4 DNA binding region remains unchanged. The GAL80 co-factor does not bind DNA, and the DNA binding footprint may remain unchanged for differences in expression level. (For a review of Prokaryotic and Eukaryotic gene regulation, see Ptashne, A Genetic Switch $2^{nd}$ edition, Cell Press and Blackwell Scientific, 1992.) The assay methods described in the present invention enable the researcher to determine both scenarios.

For a given gene, with no knowledge of transcription factor DNA binding site specificity it is very hard to identify which transcription factors may be binding. Given known binding sites for transcription factors, determined by any number of the methods described in this patent and given the DNA sequences (which can be determined by sequencing of genes of interest if the entire genome of the organism is unknown) in the promoter region of a gene one can begin to make connections between binding sites and genes which may be affected. For example, the DNA-binding transcription factor GCN4 binds to a particular 6 base-pair DNA sequences in yeast TGACTC in either orientation on the genome. This particular sequence is found throughout the yeast genome in the promoter region of many genes. However, the genes that are actually responsive at any one time is a subset of these. The algorithms and methods of this patent rapidly identify DNA-binding sequences (and information on the binding specificity and affinity) of these sequences using cell extracts or some other source of purified or non-purified transcription factors.

In addition to the foregoing, if the sequences of one or more promoter regions is known (in the case of many organisms, virtually the entire genome is known), these sites may be easily located within each promoter region.

Given the small size of many DNA binding sites, by sheer random chance, these sequences would appear more often than every $4^N$ bases (where N is 6 in this case). However, we know from numerous studies that not only are these DNA-binding sequences important, the promoter regions of any given gene are not in fact entirely random. Identification of a known or experimentally determined DNA binding site is rarely enough specificity to activate (or repress) nearby gene expression. Experimental studies have determined that quite often, several DNA-binding factors must work cooperatively to effect gene expression at any significant level (in biochemical terms, this frequently leads to a non-unity Hill coefficient—see Ptashne, A Genetic Switch $2^{nd}$ edition, Cell Press and Blackwell Scientific, 1992 and Fabio M. V. Rossi et al., Transcriptional Control: Rheostat Converted to On/Off Switch Molecular *Cell* 6:723-728 (2000)).

With information obtained from individual short binding sites (such as the GCN4 footprint) combined with mRNA transcriptional levels for a neighboring genes, we develop a profile of which subsets of sites correlate with gene activation. The algorithm works as follows:

1. All known binding sites found to be active in cells (or in vitro simulation) in a given experimental condition X (where this is a particular treatment condition, homogeneous cell population, certain point in time, or a single cell) are determined using one of the methods of this patent or any other method.
2. This set of binding sites is searched throughout the promoter regions of genes of interest. This can be a single gene up to the size of the whole genome.
3. Gene transcript expression levels are assayed by mRNA level (using northern blots, real-time PCR (available instruments from Perkin-Elmer, Roche and others, or classical microarray experiments).
4. For each gene's promoter region, a table is constructed containing an entry for each experimental condition. Such entries contain a list of all of the active binding sites for the gene (as identified in step 1), and an indicator of the transcriptional activity of the gene for this condition.
5. Further analysis of this data may take many routes depending upon the interests of the researcher performing the analysis, however, there are some summary results which may be performed, and which may lead to further experiments and conclusions:
6. For each site described in the table, it may be scored in statistical terms as having positive, negative or either affect on gene expression, and if so, how strongly.
7. Sites that have exhibited little or no effect on any expression level, high or low can be considered to be non-functional in the context of the experimental conditions explored.
8. Sites which have positive and negative effects are candidates for:
   a. More than one transcription factor binding. In one case it may be an activator, in another case, it may be a repressor.
   b. There may be an influence on transcriptional activation based on some non-DNA binding factor.
   c. Patterns of certain sites that have a high score in the positive or negative direction may be working cooperatively with one another.

d. Potential binding sites on genes whose expression level has never significantly changed in all experimental conditions thus far cannot be rejected with a high degree of confidence.
e. Competition between binding sites can be determined by examining the overlap in binding site sequences. Different table entries containing binding sites with overlapping binding sites are likely to be competitive with one another.
9. If this analysis is performed for multiple genes (either in independent or the same actual experiments) and the results over several genes combined, one can rank the most common combinations and their effect in multiple instances. Finding the same combination working in the same manner on other gene promoter regions is good evidence of a modular control mechanism at work where the components of the module are some group of transcription factors working together and binding certain site combinations.

Of course, everything that was said for the individual gene level can be generalized to the genome level where one has a collection of genes.

Ideally, experimental conditions are able to test all combinations of binding sites that lie in the promoter region of a gene. Practically speaking, this would be difficult at best, however, by determining the individual binding sites for each transcription factor individually, and in all forms and site affinities, then the problem becomes more tractable.

In the preferred embodiment of this invention, it would be best if the mRNA analysis and the active promoter region analysis were performed on fractions of cellular extract from the same cell(s). In an instance where that is not practical, separate experiments with identical conditions may suffice however, it may also add noise to the analysis. Furthermore, the source of the material need not be an in vivo culture if experimental methods progress to the point where transcriptional control in vitro is possible for the system under study.

In the preferred embodiment for transcription factor, the mRNA expression levels can be determined by microarray analysis because it is easier to get information on many genes simultaneously, and differential expression can be determined more easily and accurately. For example, if two experimental conditions are changed, and the binding sites change, then this change can be correlated with the change in expression levels of genes as described above.

Such change in expression levels combined with the change in binding site preferences from one experiment to allows one to infer causality. Importantly, binding sites on a particular gene promoter region that have changed receive a low confidence score of having any effect on the cognate gene's expression level.

In general, longer sites are better than shorter ones to discover cooperative binding effects. However, shorter sites are better than longer sites to find binding sites for individual transcription factors and their binding sites in the absence of cooperative effects. Cooperative effects can be economically tested by creating DNA probes which consist of combinations of individual binding site sequences, and integrating that information with any other DNA-binding and expression data.

First, with current technology, the number of exhaustive probes that can be practically attached to a chip is limited to on the order of 10-100,000 probes per chip. This will allow an exhaustive set of DNA probes of length 8, but not higher. While advances in this technology will undoubtedly allow for the manufacture of chips with higher densities of probes over time, at present, new alternate methods for assaying using a larger set of probes are described below.

Method of Causal Binding Site Determination

Starting with:

Gene expression levels E(i, j) for each gene i we are assaying in each condition j Expression levels are assumed to be normalized to be at least qualitatively comparable (i.e. Northern Blots or better.) and Potentially active binding sites B(i, j) for gene i in condition j. Each site in the set B(i, j) would be distinguished by its offset from a standard location with respect to the gene, and its length or alternatively its sequence and length at that site. By 'active' we mean it has an effect on gene expression either positively or negatively.

where
i=the gene number from 1 to N (may be 1 to thousands), and
j=the Experiment number from 1 to M Pseudo code:

For each gene i (from 1 to N) {
Create set C(i) and initially set it to the empty set { }.

```
For j = 1 to M {
    For k = 1 to M {
        For each potential binding site D in set B(i, j) and not in set B(i, k) {
            if (E(i, j) < (E(i, k) - epsilon)) {
                Add site D to the set C(i) with the flag '-'
            }
            else if (E(i, j) > (E(i, k) + epsilon) ) {
                Add site D to the set C(i) with the flag '+'
            }
        }
    }
}
}
``` where
epsilon is some small amount related to noise or desired significance level threshold Each Set C(i) corresponding to each gene i contains a set of binding sites that appear to affect regulation of gene i in the direction indicated. In other words, they are truly 'active'. That is, a '−' flag would indicate evidence of down-regulation by a factor associated with this site, and a '+' flag would indicate evidence of up-regulation by a factor associated with this site. Both flags associated with a particular site would mean there is evidence that this site is being used in both up and down regulation. Potential hypotheses include repressors and activators competing for the same site, or other non-DNA binding factors that may convert a particular binding site from an activator to a repressor.

A modification to the above algorithm would gather quantitative expression data pertaining to each site instead of '+' and '−' flags. In this manner, each difference in expression level could be associated with the binding site for a particular gene. Such values may then be statistically analyzed. Among other things, useful analyses are likely to be averaging of the differences in expression levels, and generation of a histogram to determine bimodal patterns of regulation associated with the particular site.

Each experiment that generates potential binding site data is limited by the maximum length of the probes used in the experiment. Experiments with longer probes can be combined with experiments with longer probes to obtain information regarding co-operativity between various bound factors at each site.

For example: Suppose a 'short probe' binding experiment has identified site1 and site2 on Gene X to both influence expression in some up or down direction. Suppose further that in another 'long probe' binding experiment, a binding site3 has been found also for Gene X that completely overlaps site1 and site2. The longer binding site expression level may be higher than the expression level associated with site1 or site2 or the sum of both. In other words, site1 and site2 are not acting independently, but rather in a cooperative manner.

One caveat of this algorithm is that unless enough experimental conditions j are performed to generate many sets B(i, j) and E(i, j), it is possible to miss binding sites which have an effect on a particular gene, but are constitutively active. There are two resolutions to this problem.

First, if there is an active binding site, it must be a member of the set of potentially active sites B(i, j) if the probes used to generate B(i, j) were long enough to capture all relevant factors that bind DNA, experimental conditions were correct, etc. Therefore, in vivo genetic mutation experiments may be used to target these potentially active binding sites vs. the entire promoter region for a given gene.

Second, 'Promoter Site Mutagenesis foot-printing' using the method described herein to determine potential binding sites for a given promoter region can be performed to narrow the set B(i, j) further.

Another modification to the above algorithm groups sites into seemingly cooperative sets. So, instead of '+' and '−' flags for each potential binding site, gather into C(i) data of the form: Expression change, sites newly bound, sites newly released, potentially constitutive sites.

where

Expression change=E(i, j)−E(i, k)

sites newly bound=all potential binding sites in B(i, j) not in B(i, k)

sites newly unbound=all potential binding sites in B(i, k) not in B(i, j) and potentially constitutive sites=the intersection of sites B(i, j) and B(i, k)

This treats binding sites as a group vs. independently, which, with cooperative binding, may be more informative for seeing gross patterns in regulation of a given gene. In this manner, each difference in expression level could be associated with gross changes in the binding sites for a particular gene.

Potential binding sites will contain a lot of noise due to the random frequency of binding sites in the genome. One way to filter the potential binding sites that may be active for a particular gene is to eliminate any potential binding sites for a gene to those which fall within its Promoter Mutagenesis Footprint (see description herein).

Longer Strands are Superior

Direct effects of cooperative binding may be assayed for by the use of longer probes. If there are technical or practical limitations that prevent the creation of and exhaustive set of probes over a certain length then, longer probes with combinations of subsequences known to bind some DNA-binding proteins can be generated as an alternate to an exhaustive set of sequences.

Methods for Focusing Binding Regions from Gross Binding Site Output

Further analysis of such information, and any additional knowledge about sequences that were not bound, can be used to focus in on what subsequences may be the real targets of such binding by the DNA-binding proteins.

A number of algorithms for this analysis are possible, and two of them are described below. An implementation of the first algorithm written in the Perl programming language is given in Appendix I.

Both algorithms assume an input data set consisting of the sequences of all of the probes in the assay and a Boolean or qualitative indication of the binding affinity of the target DNA-binding protein for each of the probes. Let set A represent all probes, and let set B represent all bound probes (by definition B must be a subset of A).

VII A. Algorithm 1 (in Silico Simulation Method)

Here is the pseudo-code for the first algorithm:

```
Initialize set H = { }
For each possible subsequence Ti of length <= N comprised of the
probe's possible nucleotide bases (usually {ACGT}), where N is the
length of the shortest probe {
    Initialize C = { }
    Search for the subsequence Ti through each of the probe
    sequences corresponding to each of the probes in the complete
    set of probes, A. Whenever Ti is found within a probe
    sequence, add the probe to set C. If set C is a subset of B,
    then add Ti to the set of hypothetical binding sites H
    }
// Comment: At this point, set H contains all binding sites that are
// consistent with the actual binding site data in B.
```

In a pruning step, all hypothetical candidate binding sequences in H that contain within them other candidate sequences are eliminated until such condition no longer exists.

Sites remaining in Set H represent the focused binding sites generated by the algorithm from Gross Binding Site Data.

The steps above are simplified for purposes of discussion, however, optimizations may certainly be performed by those skilled in the art of computer programming and mathematics. For example, the pruning step can be folded into the first step where a subsequence is chosen to perform the computerized search through the probe sequences. In that case, a test subsequence, Ti, which already contains within it, a sequence in set H, should be skipped and discarded. This optimization pre-supposes that shorter subsequences are tested before longer subsequences.

Figure 18:
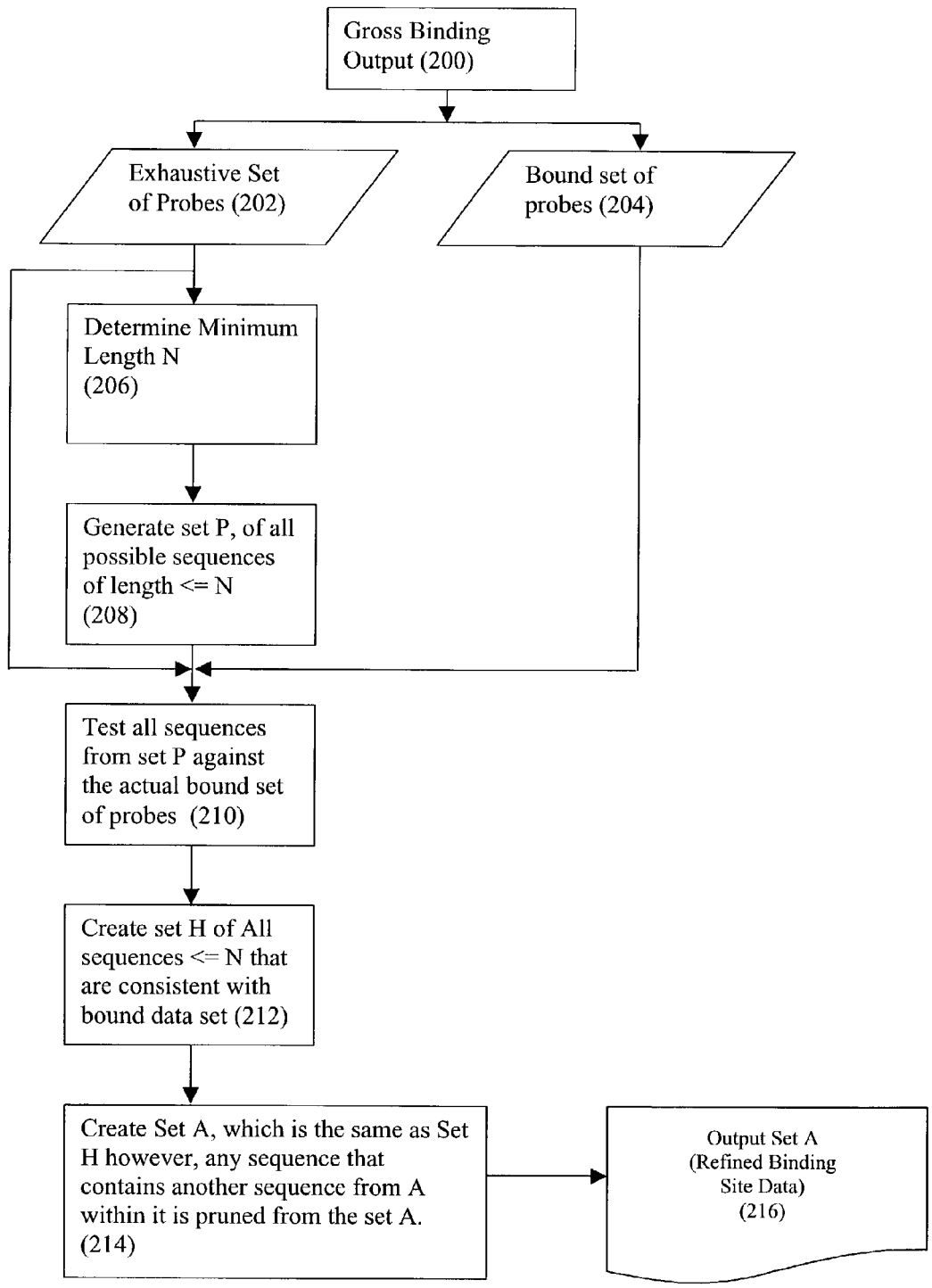
FIG. 18: Flowchart of Algorithm 1 for focusing Gross Binding Site Data into Refined Binding Site Data.
Figure 19A:
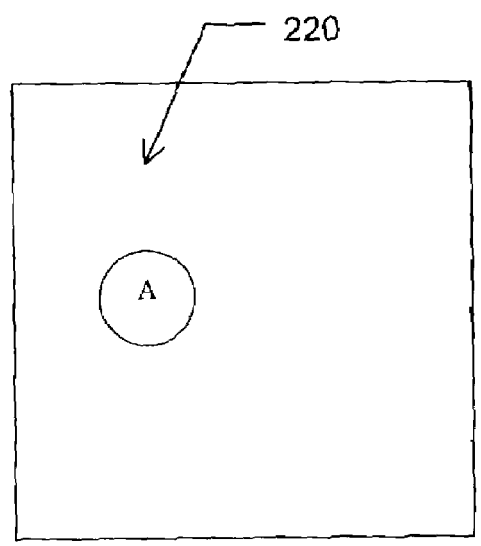
Figure 19B:
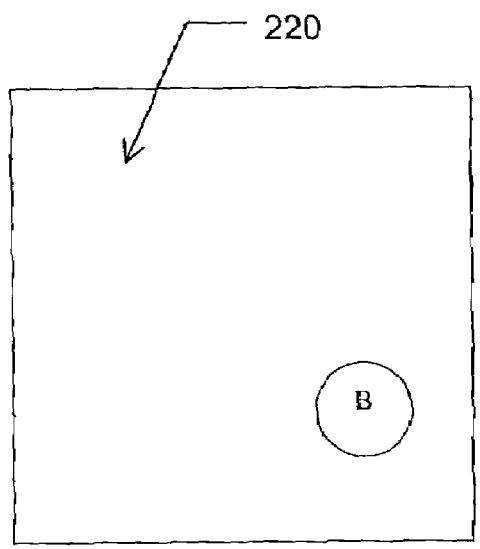
Figure 19C:
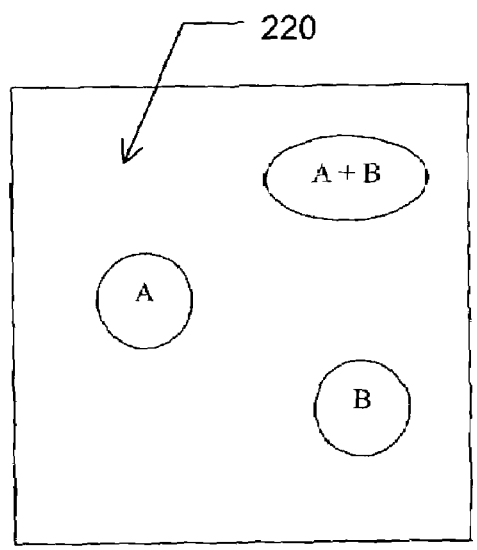
Figure 20:
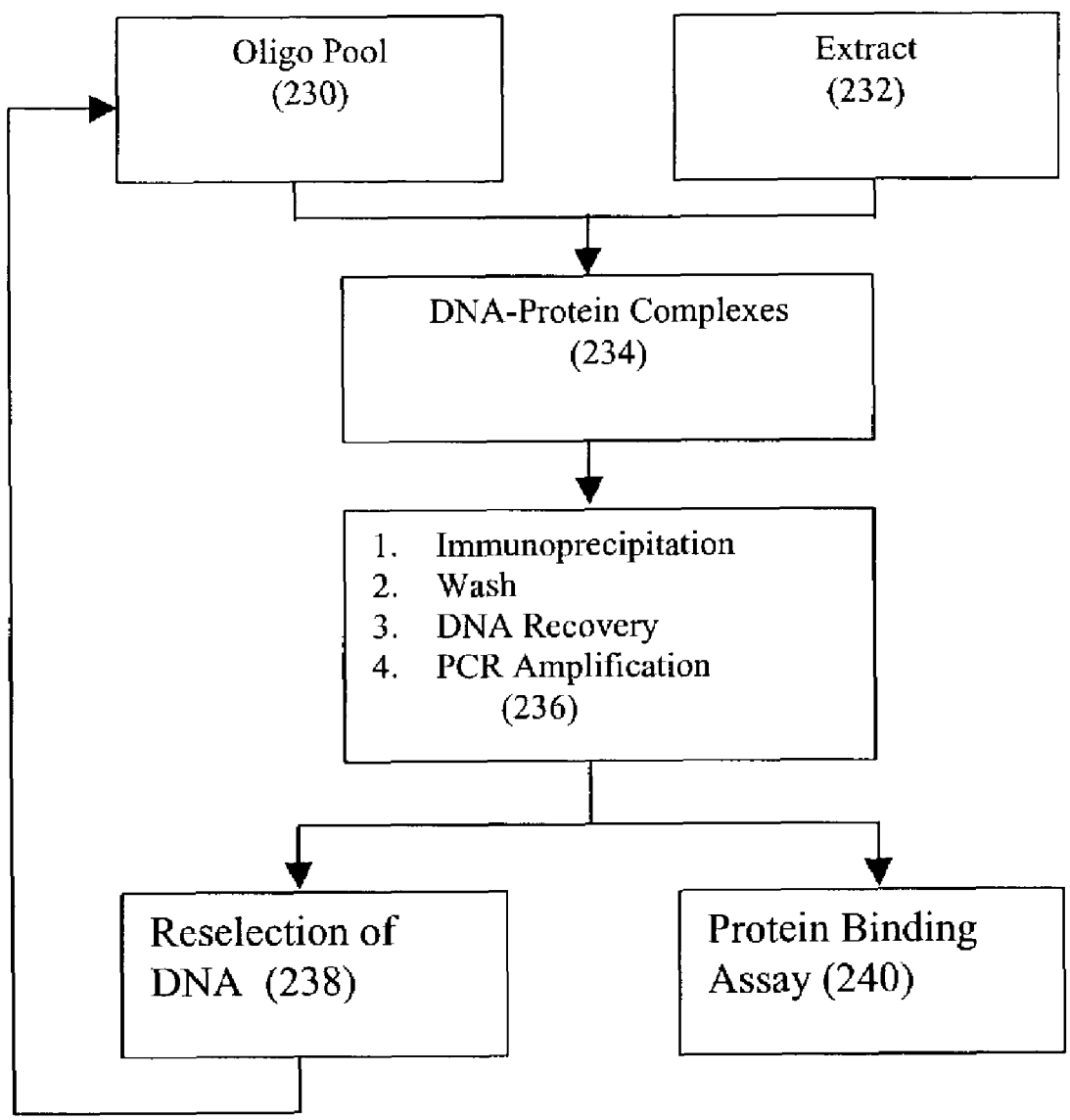
FIG. 20: Flowchart of the method by Pollock, R. and Treisman, R, A sensitive method for the determination of protein-DNA binding specificity. From *Nucleic Acids Research*, 18: 6197-6204, 1990.

See FIG. 18 for a flowchart of the algorithm, however, the symbols in the flowchart do not necessarily correspond exactly to the algorithm described immediately above.

Appendix I contains an implementation of the algorithm written in the Perl programming language.

Method 2 (Associative Memory Lookup Method)

An alternative algorithm involves the use of sparse matrices in an "associative memory" programming model. This method relies upon the fact that with an exhaustive set of probes of length N, each subsequence of length <=N will create a unique signature based upon the set of these probes of length N that contain that subsequence. For example, GATT in a set of 4096 dsDNA probes representing each of the exhaustive set of $4^6$ probes will identify 48 sequences on one strand direction, and 48 probes in the opposite strand direction (in some cases, for odd length probes, a palindrome may result altering this number slightly). This set of 96 probes is unique for this sequence. By a hash table, b-tree or other data structures designed to store and retrieve sparse data sets, one can use the empirically determined probe sets to map back to the subsequence which would have given rise to that signature pattern.

In both methods, the algorithms may be extended to account for imperfect experimental conditions and the reality that not all probes are bound with the same affinity, kinetics or efficiency. This leads to more quantitative treatment of the data. In the case of the first algorithm, experimental strengths of binding to particular subsequences may be inferred from the strengths of binding to the actual probes containing these subsequences. In the case of the second algorithm, non-perfect signatures, or questionably included probes may both be handled by using methods to determine the nearest neighboring signature to the one found. For example, if experimentally, one finds only 94 probes are bound, then using different metrics for distance to a nearby signature can be used. The signature may be thought of as a vector in hyperspace corresponding to (in this example) one of $2^{4096}$ possible signatures. This is a highly over-specified space because on the order of $4^7$ sequences must sparsely map into that space in a 1:1 mapping. Therefore, there is a great deal of 'disallowed' space between points in the larger space, so experiments with noise are likely to be nearer to one point or the other in the larger space. If an experimental point is determined to lie between these idealized signature points, then one possible interpretation is that the real binding affinity lies somewhere between the binding for each point. In fact, the first algorithm while possibly more computationally expensive, can allow for the possibility of multiple different binding sites which may occur simultaneously.

Method of Iterative Sanger Sequencing for Non-Pure Populations

Figure 21:
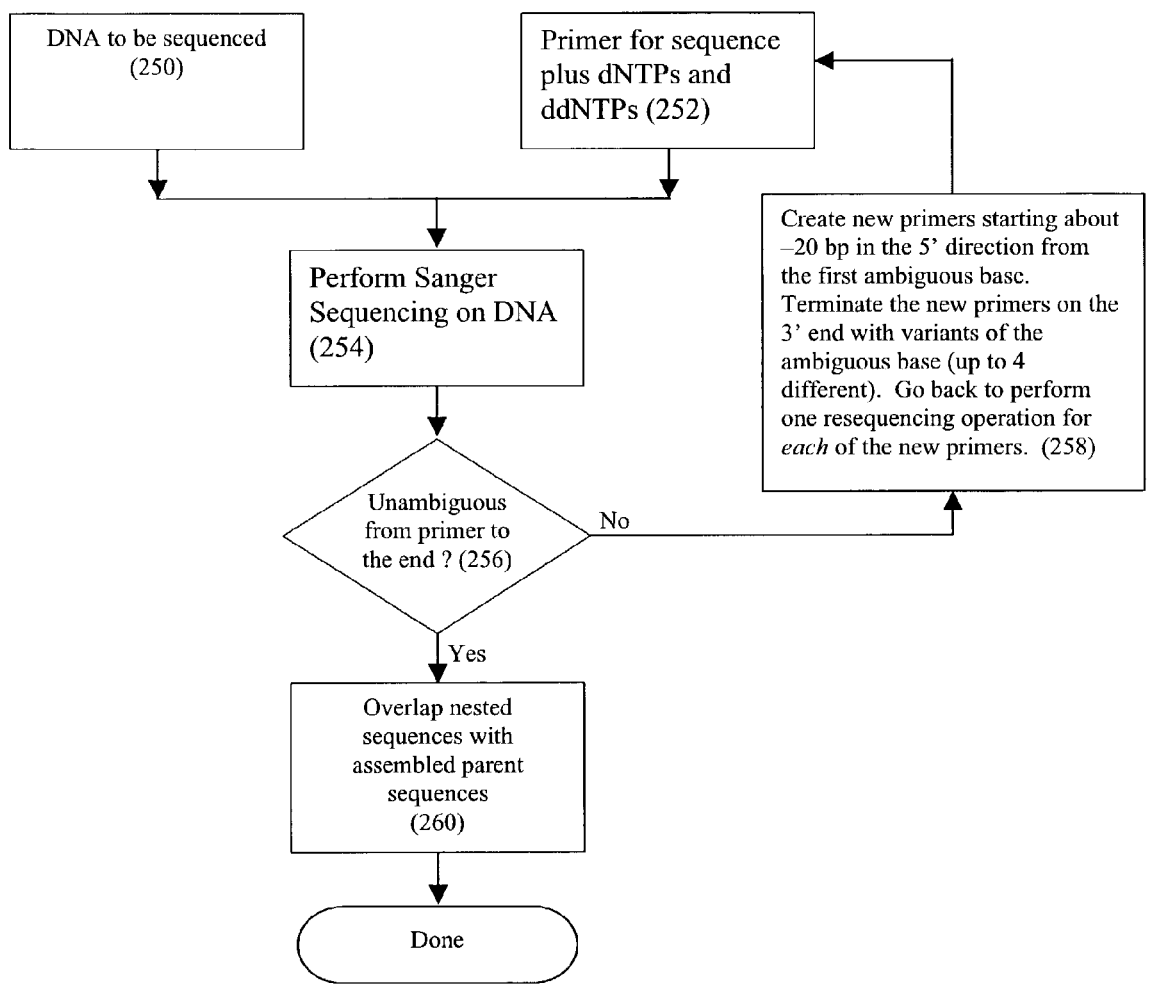
FIG. 21: Iterated Sanger Sequencing flowchart.

In the case of attempting to sequence a non-separable set of DNA sub-populations with different sequences the preferred embodiment of the method follows (FIG. 21 shows a flowchart of the method):

1. Standard Sanger Sequencing (Sambrook et al., Supra, and Sanger, F. *PNAS* 74: 5463-5467, 1977) is performed on the population using dye-termination chemistry.
2. a) If there are no ambiguous bases in the sequence (as evidenced by only one dye tag represented at each position), then the sequence is complete for that sub-population. b) If there is a base pair position that is ambiguous due to the fact that there are two or more bases in the read-out for that position, then up to 4 new Sanger sequence primers are designed such that they will hybridize to the region in the 5' direction from the ambiguous site, but they will differ in the last base position. With these new primers, the original sequence pool is aliquoted with each new sequencing primer and sequenced again. This is repeated for each sub-pool until a tree of sequences with no ambiguity is achieved or the region of interest is determined, and can be stopped.
3. If another ambiguous base arises, continue to perform this resequencing recursively until the end of all sequences is reached with no more ambiguous bases. Overlap all nested sequences with the parent sequences to determine the sequences of each strand of the population.

This method is highly applicable to the methods of random fragment foot-printing described herein, but it clearly has other applications such as in the analysis of a population of different alleles that are not separable by length or other means.

Example: 3 Fragments in Solution (Note: We are Using Short Sequences and Primers and we are Showing the Sequencing of the Primer Sequence Just to Illustrate the Principle.)

```
                                              SEQ ID NO:1
ATCTGCTCGCTGCTGGGTCTAGCTTAGCTAGCT             (frag 1)

SEQ ID NO:2
ATCTGCGCGCTGCTGGGACTAGCTTAGCTAGCT             (frag 2)

SEQ ID NO:3
ATCTGCTCGGTGCTGGGTCTAGCTTAGCTAGCT             (frag 3)
```

Stage 1: Primer: ATCTG

First Pass Sequencing Output:

```
                                      SEQ ID NO:4
ATCTGCTCGCTGCTGGGTCTAGCTTAGCTAGCT
     G          A
     T  G
```

Which will be indistinguishable from:

```
                                      SEQ ID NO:5
ATCTGCTCGCTGCTGGGTCTAGCTTAGCTAGCT
     G  G       A
```

Which could mean that there are at most 2×2×2=8 different strands. Next, we generate a new primer up to and including the first degenerate base.

Stage 2: Two New Primers: CTGCT and CTGCG

```
Stage 2a sequencing output (Primer: CTGCT)
                                     SEQ ID NO:6
CTGCTCGCTGCTGGGTCTAGCTTAGCTAGCT
   T  G
```

Which will be indistinguishable from:

```
                                    SEQ ID NO:7
CTGCTCGCTGCTGGGTCTAGCTTAGCTAGCT
      G
```

Stage 2b sequencing output (Primer: CTGCG)

CTGCGCGCTGCTGGGACTAGTTAGCTAGCT SEQ ID NO:8 (Unambiguous. Done!)

Stage 3: Two New Primers: CTCGC and CTCGG

Stage 3a Sequencing Output (Primer: CTCGC)

CTCGCTGCTGGGTCTAGCTTAGCTAGCT SEQ ID NO:9 (Unambiguous. Done!)

Stage 3b Sequencing Output (Primer: CTCGG)

CTCGGTGCTGGGTCTAGCTTAGCTAGCT SEQ ID NO:10 (Unambiguous. Done!)

Final Alignment:

```
                                         SEQ ID NO:11
    ATCTGC?CG?TGCTGGG?CTAGCTTAGCTAGCT

SEQ ID NO:12
    CTGCTCG?TGCTGGGTCTAGCTTAGCTAGCT

SEQ ID NO:13
    CTCGCTGCTGGGTCTAGCTTAGCTAGCT

SEQ ID NO:14
    CTCGGTGCTGGGTCTAGCTTAGCTAGCT

SEQ ID NO:15
    CTGCGCGCTGCTGGGACTAGCTTAGCTAGCT
```

Assembling Unambiguous Parts from the 5' Direction:

```
    ATCTGC

CTGCTCG

SEQ ID NO:16
        CTCGCTGCTGGGTCTAGCTTAGCTAGCT     (frag 1)

SEQ ID NO:17
        CTCGGTGCTGGGTCTAGCTTAGCTAGCT     (frag 2)

SEQ ID NO:18
        CTGCGCGCTGCTGGGACTAGCTTAGCTAGCT  (frag 3)
```

Final Assembly (Original Sequences Recovered):

```
                                         SEQ ID NO:19
    ATCTGCTCGCTGCTGGGTCTAGCTTAGCTAGCT    (frag 1)

SEQ ID NO:20
    ATCTGCGCGCTGCTGGGACTAGCTTAGCTAGCT    (frag 2)

SEQ ID NO:21
    ATCTGCTCGGTGCTGGGTCTAGCTTAGCTAGCT    (frag 3)
```

Both forward and reverse complement sequences may be represented on a chip with all possible bp sequences of a given length. This may be used as a built in replicate check, and also may help resolve any asymmetric binding patterns for a given TF.

Figure 1B:
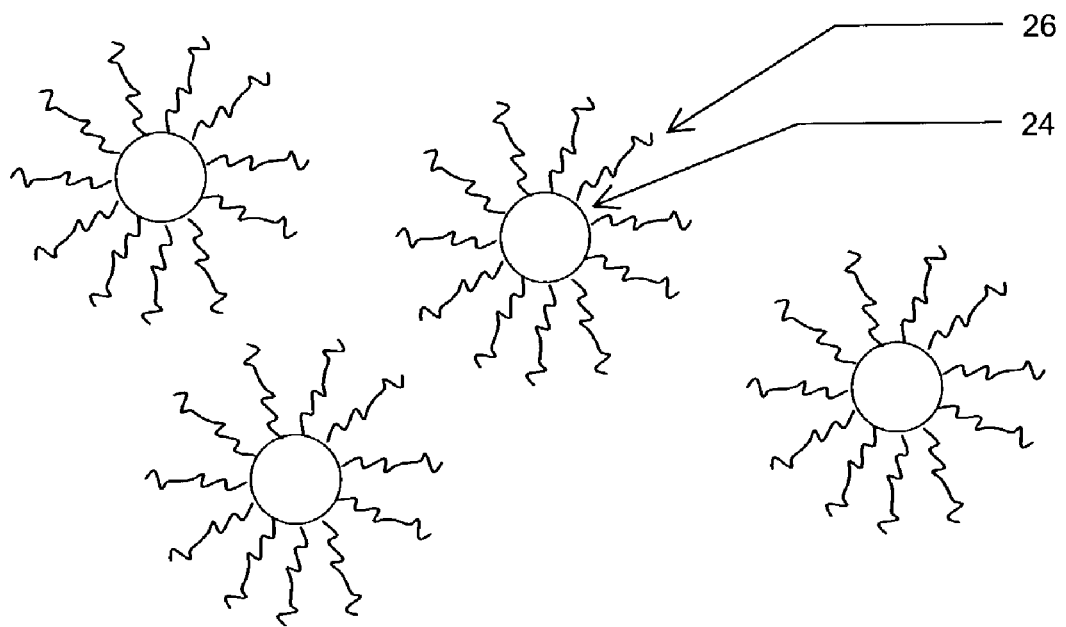
Figure 2A:
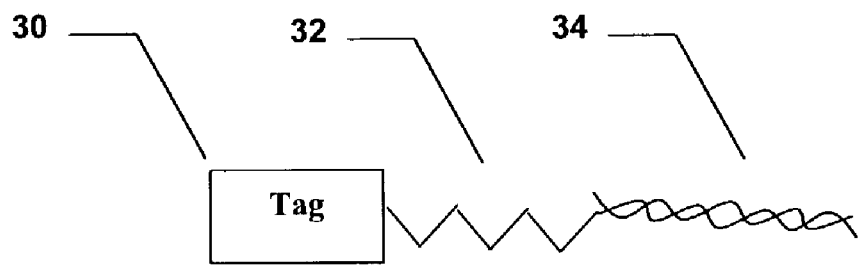
FIGS. 2A and 2B: Various methods of determining double-stranded DNA that may be later bound to proteins
Figure 2B:
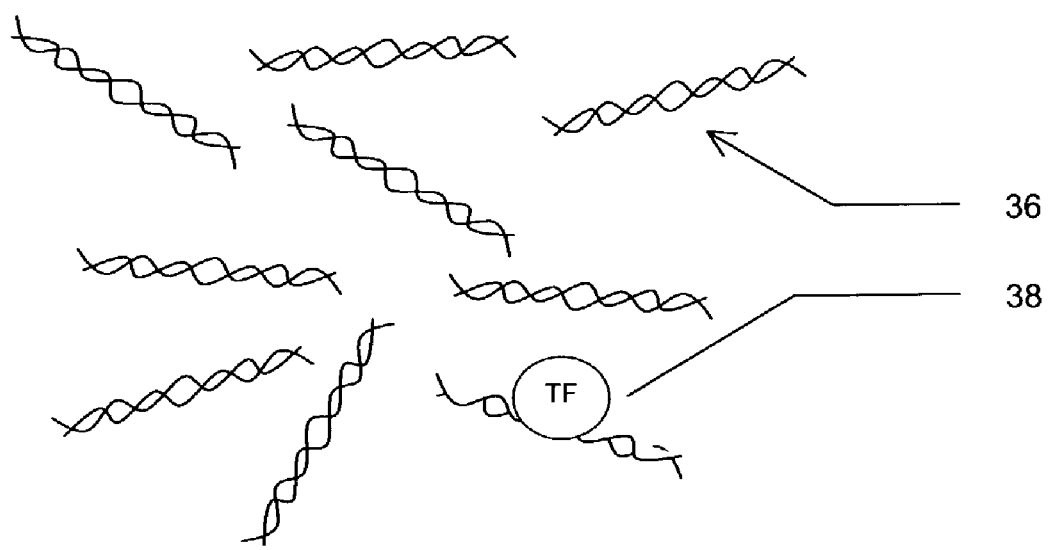
Figure 3:
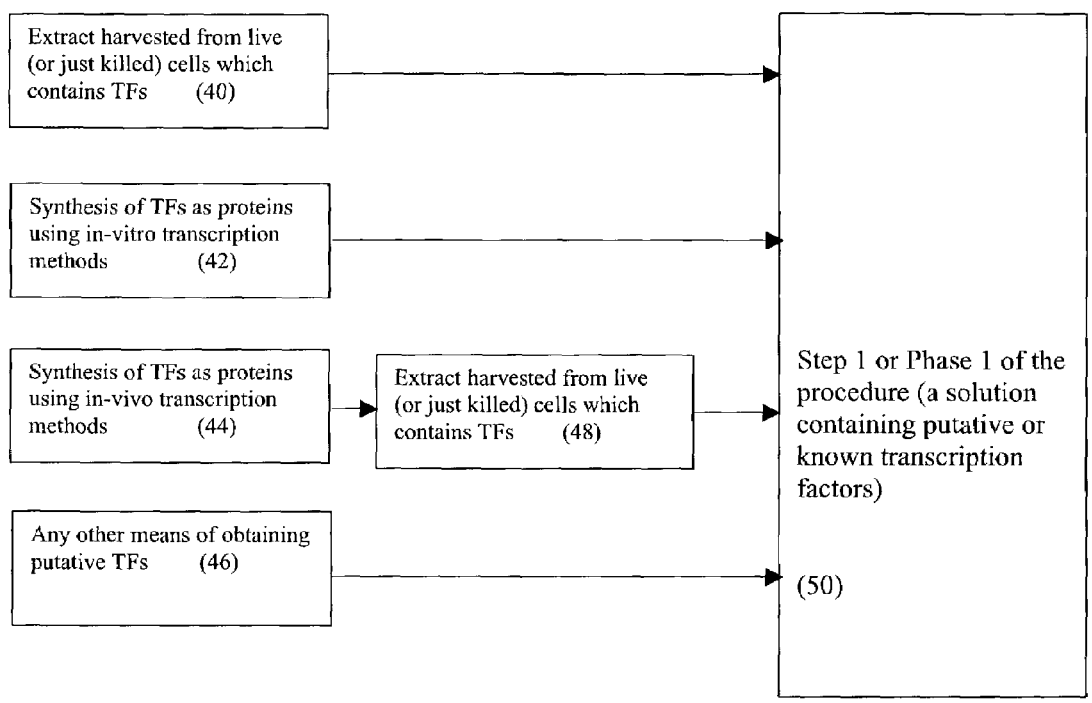
FIG. 3: Various ways to obtain the input solution to Step 1 of Phase 1 of the analysis (see FIG. 4).
Figure 4:
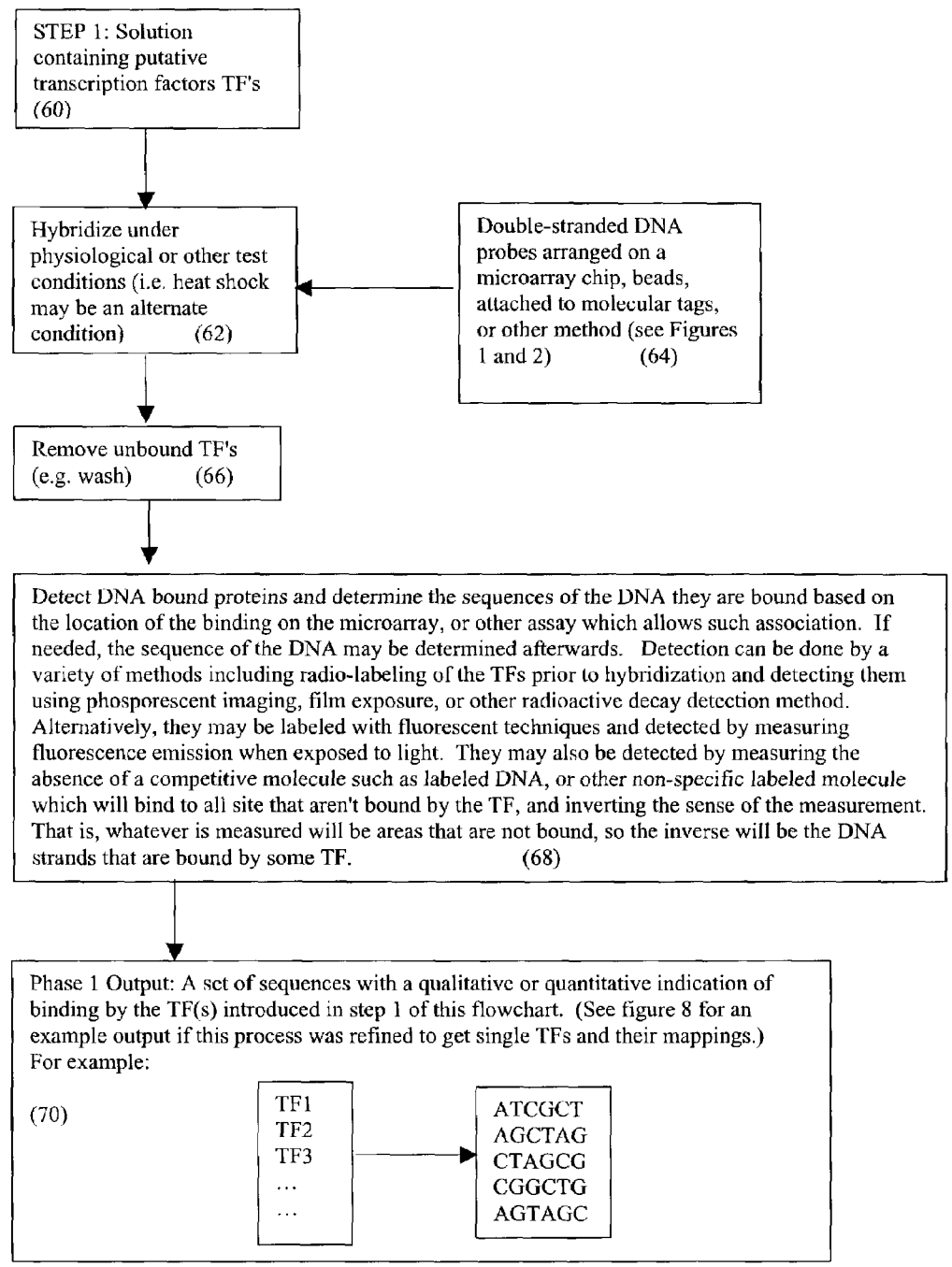
FIG. 4: Flowchart of Phase 1 of the analysis
Figure 5:
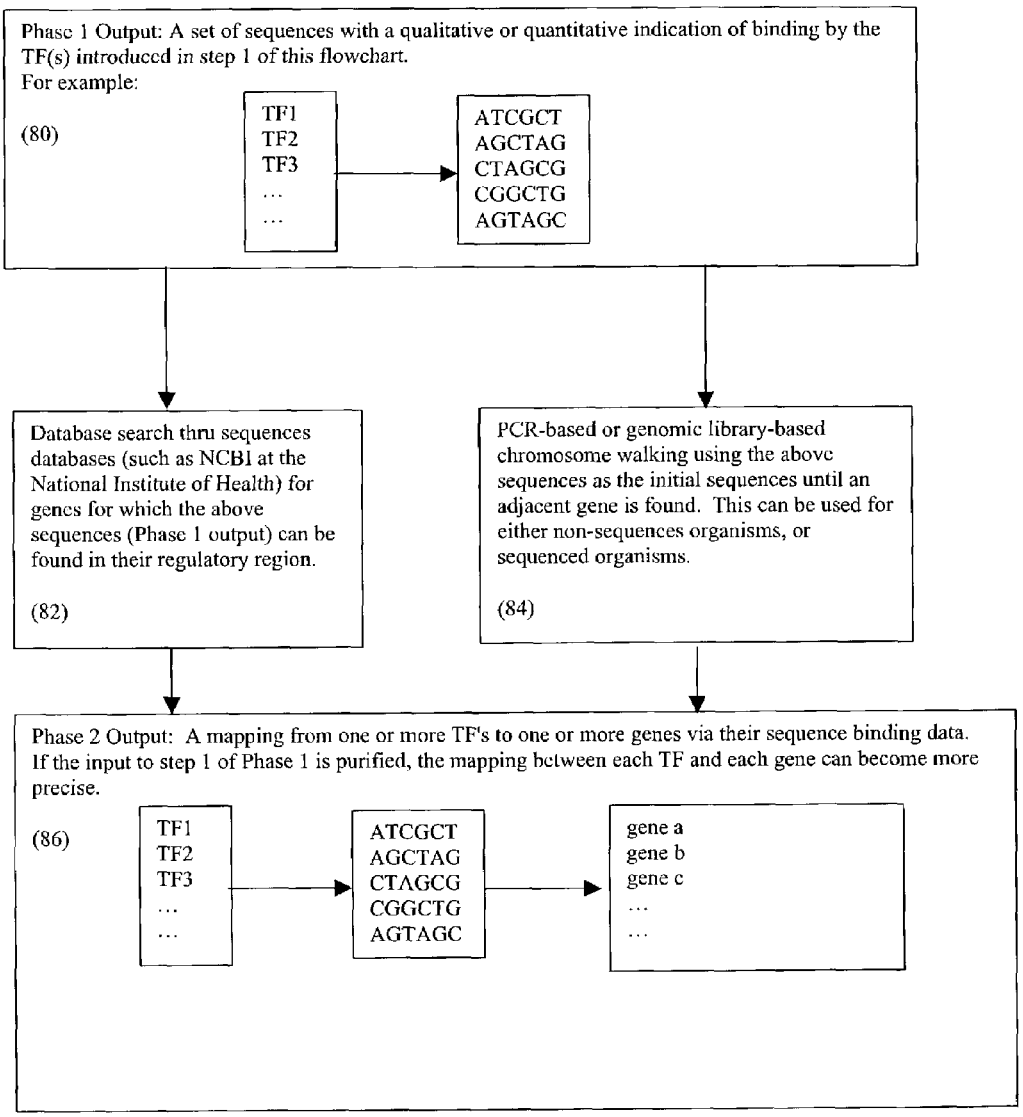
FIG. 5: Phase 2 of the analysis process—Forward analysis of potentially regulated genes
Figure 6:
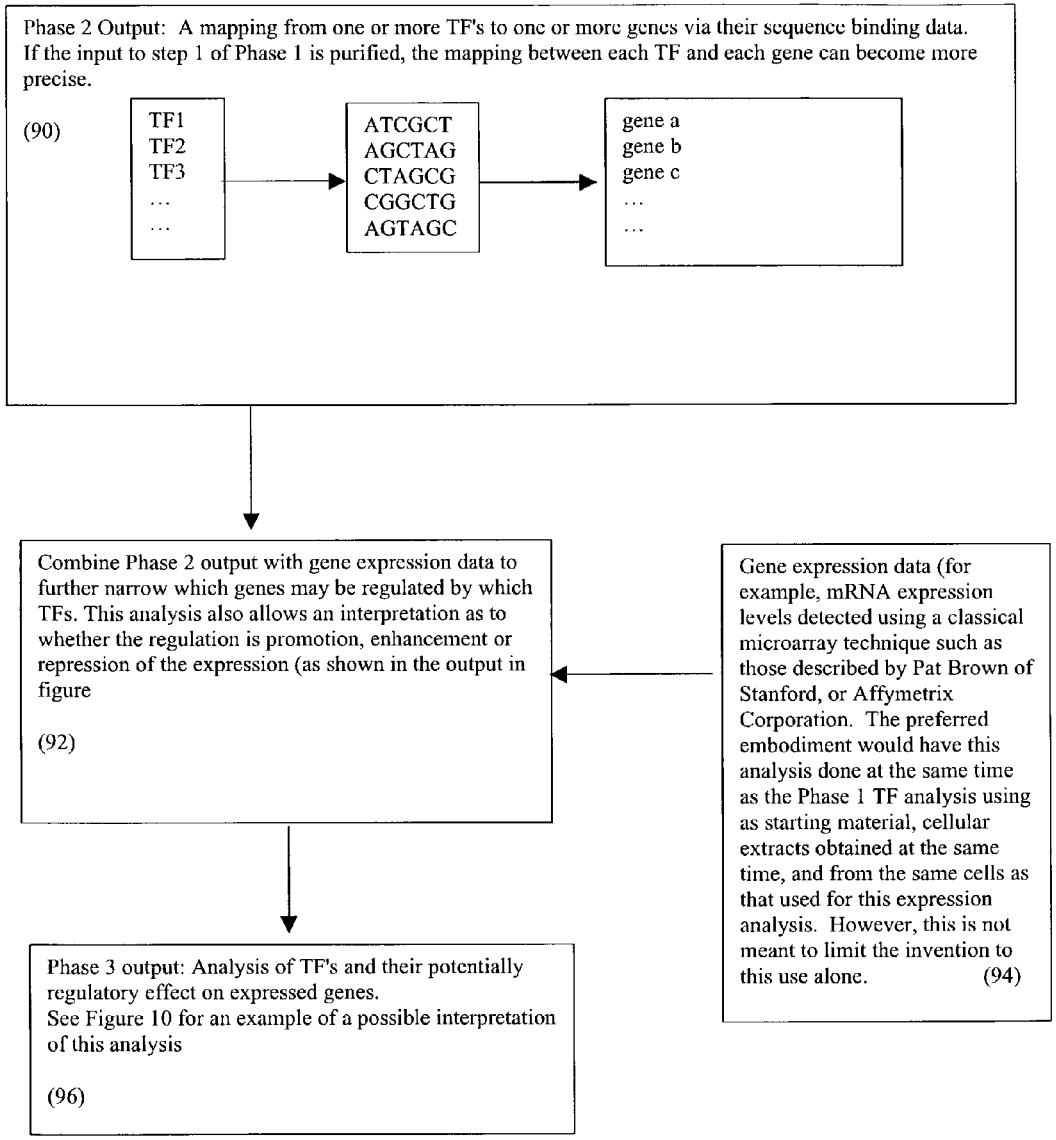
FIG. 6: Phase 3—Forward analysis combined with actual expression data to further refine potential TF→gene regulatory pathways.
Figure 7:
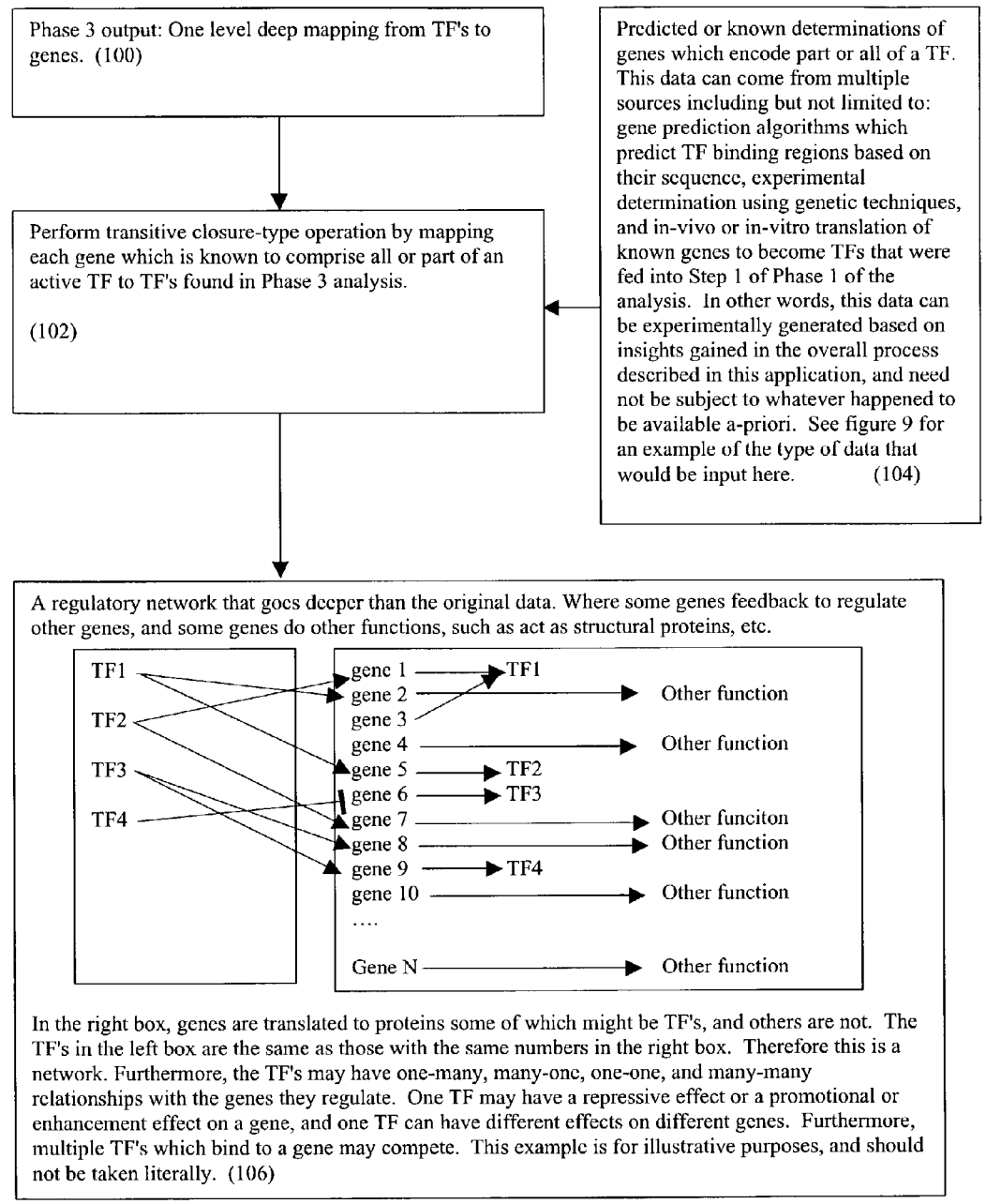
FIG. 7: Phase 4—Expansion of the regulatory network.
Figure 8:
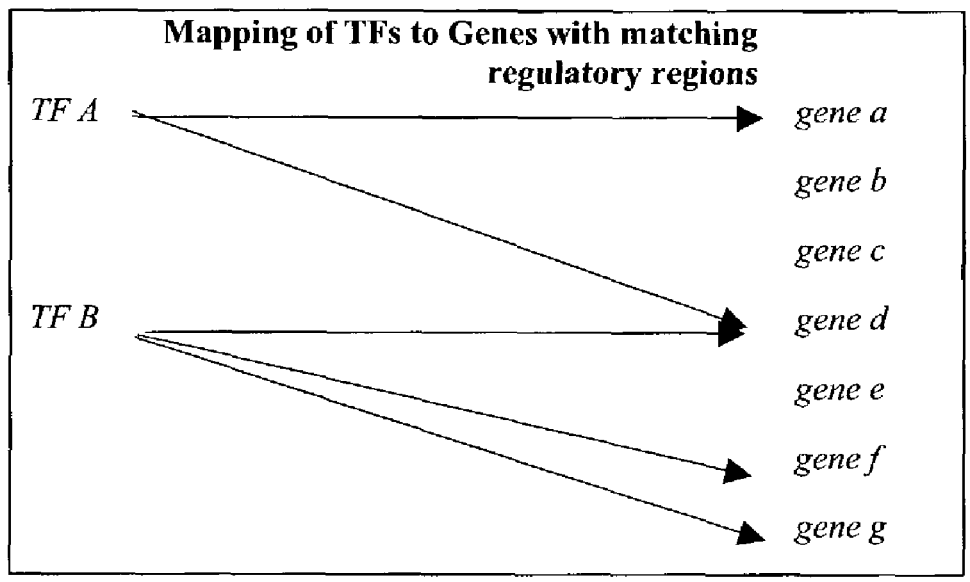
FIG. 8: TF's may be mapped to sequences in the promoter area of genes is a genomic sequence is known or if it is determined by chromosome walking techniques to determine nearby genes.
Figure 9:
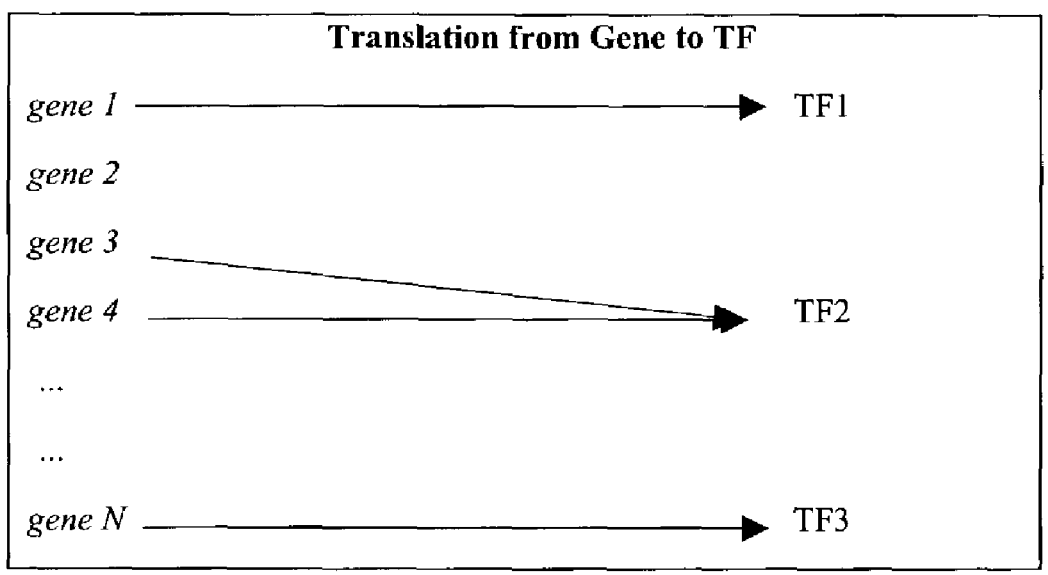
FIG. 9: Genes may be translated to TF's (which then bind to DNA)
Figure 11A:
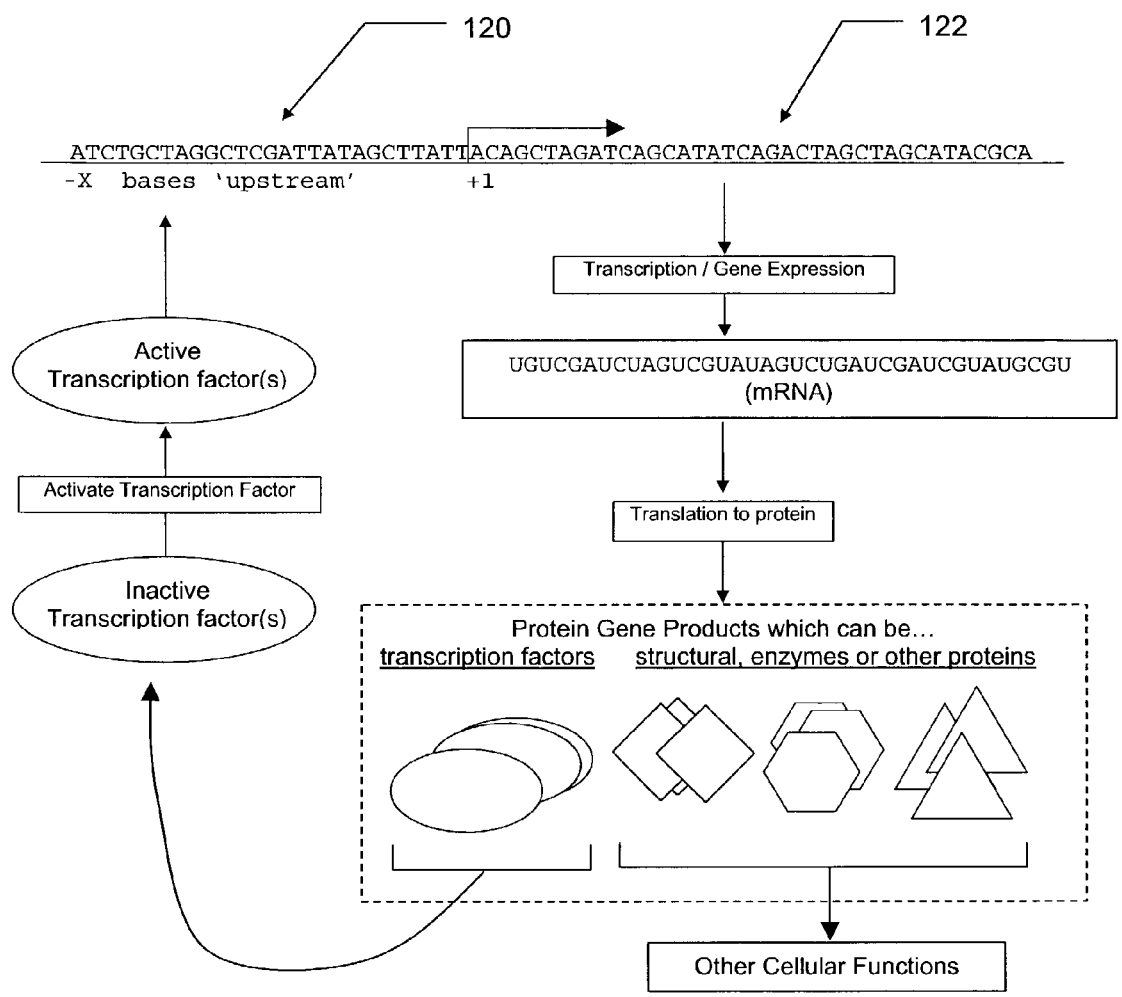
FIGS. 11A and FIG. 11B: Background on gene expression and regulation.
Figure 11B:
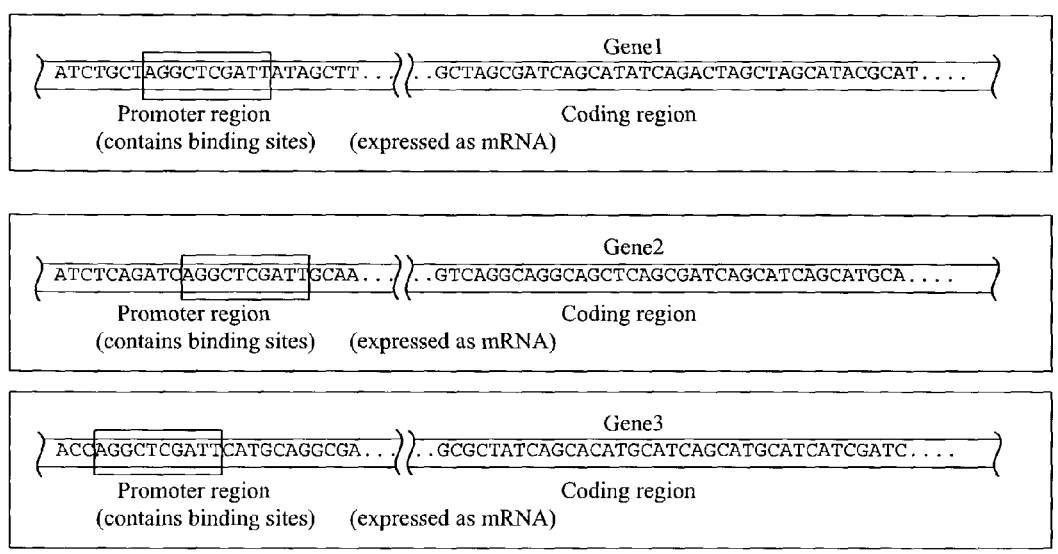
Figure 14:
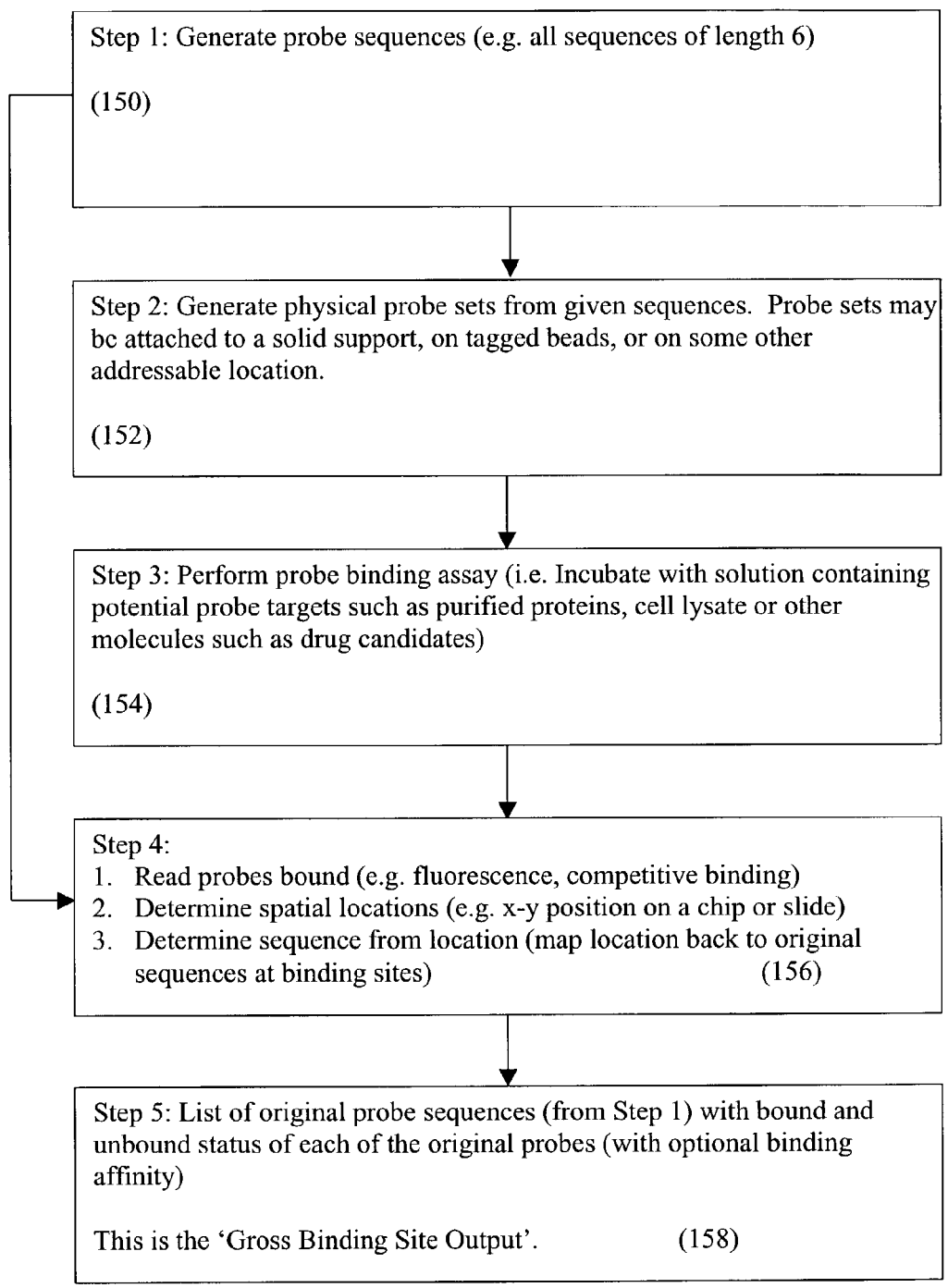
FIG. 14: Flowchart showing a method for determining the Gross Binding Site Output using methods permitting determination of probe sequences using a spatially addressable mechanism.
Figure 16:
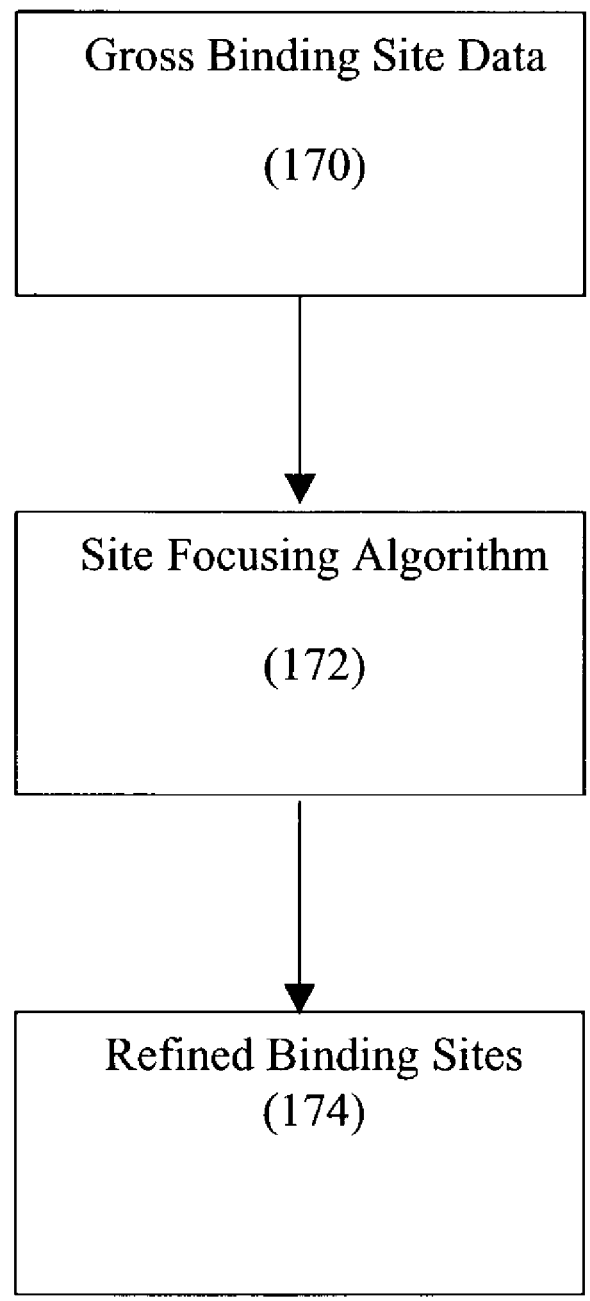
FIG. 16: Flowchart showing the focusing of Gross Binding Site Data (or Gross Binding Assay Data) into Refined Binding Sites.
Figure 17:
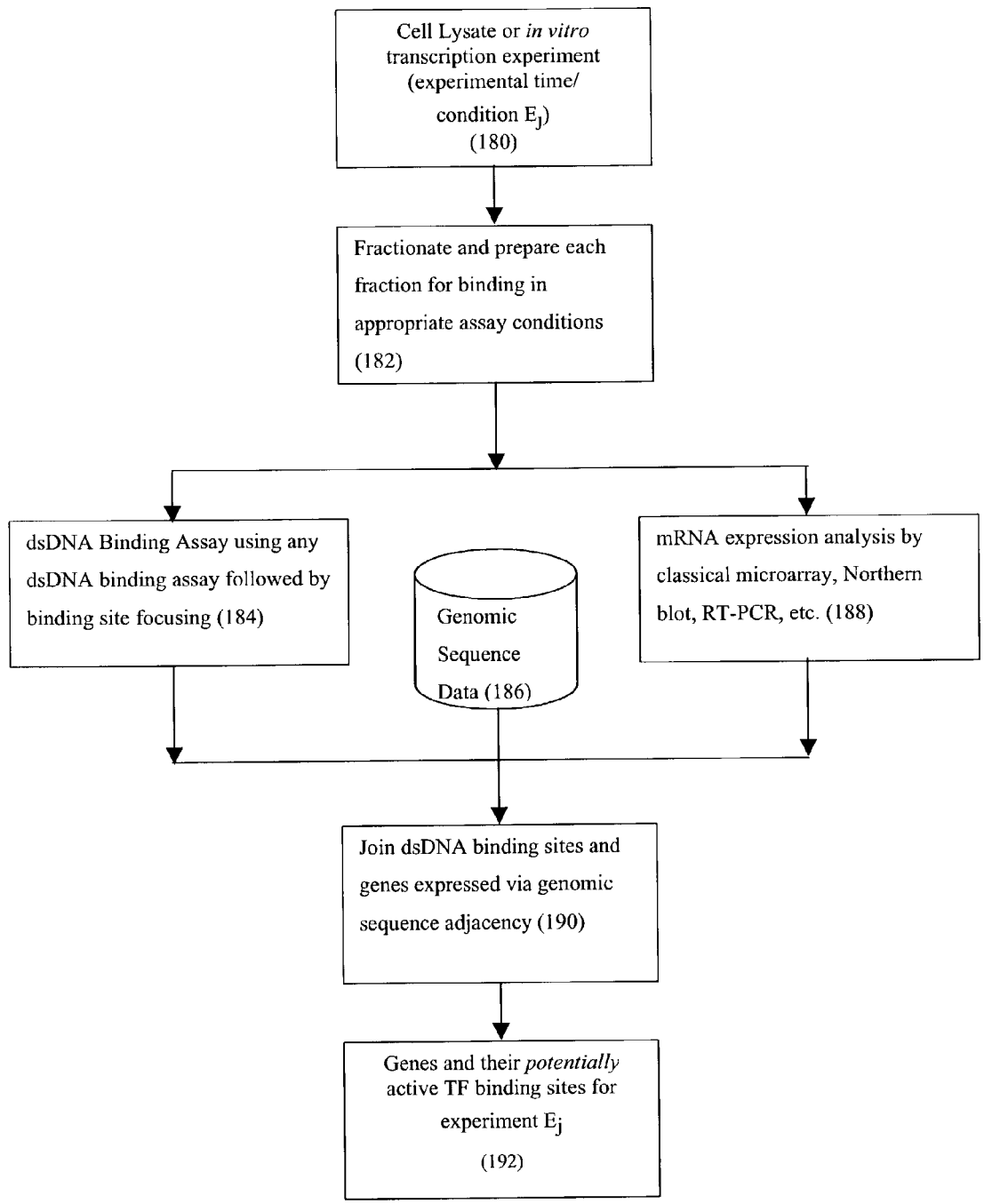
FIG. 17: Use of Genomic Sequence Data to join Binding Site and Gene Expression Data. The Genomic Sequence Data could come from a database for genes of interest that have already been sequenced. Many organisms have substantially all of their publicly known gene sequences available in a repository such as the NCBI database. This Genomic Sequence Data can also be obtained through the use of conventional methods (e.g. PCR amplification followed by sequencing, and, if necessary, chromosome walking.) For example, if the gene is known, one can use a unique primer from the gene's sequence to amplify and sequence the genes in the either direction from the gene to obtain, for instance, the standard Promoter Region sequence. If, Binding site sequences are known (such as from the discovery methods of this patent), and they are long enough, then these sequences can be used to create rare or unique primers to determine sequences of nearby genes.

The set of TF's derived from a cell, or collection of all cell types for an organism may be used as an initial screen in order to eliminate sequences on a chip (when I refer to chip here and in other parts of this application, it may mean beads or other methods of measuring DNA/protein binding described in FIGS. 1 and 2) used as a probe for TF's. This may allow the consolidation of probes which might otherwise have to be done using several sets of probes due to current state of the art in using more probes.

Replicates can be easily added to a given chip set for increased data reliability.

Extenders or spacer molecules may be added around the DNA sequences to allow for binding of TF's which might otherwise be hindered Inert extenders could be DNA, if inert DNA sequences were known. However, iteration of Phase 1 analysis (see Figures) will allow the identification of inert DNA sequences (if any exist) because they will not show up in the binding assay.

It may be that certain TF's won't bind without other TF's or related molecules such as the various components of RNA Pol II (or the main RNA or DNA polymerase for an organism). Adding it to the binding reaction may reveal patterns not seen without it or other factors.

In addition to the immediately forgoing, binding sites for these other sequences may need to be located in proximity to the target sequences. For example, a TATA region may be necessary if Pol II is to be recruited.

This invention exploits the experimental observation that an active transcription factor(s) which binds to a regulatory region and the expression (or repression) of a neighboring gene can be connected through the known or discoverable genomic sequence of the organism.

The elements of methods, devices and systems described and/or depicted in any flow diagram, and other elements disclosed herein are exemplary. A number of alternatives for each element have been disclosed, as have specific choices of alternatives comprising some specific preferred embodiments. To whatever degree these alternatives are not in conflict, any and all of the alternatives for any element are practiced, in any combination, with any and all of the alternatives for other elements, in order to create alternative preferred embodiments of the instant invention. Furthermore, certain steps or other elements may be arranged differently, combined, separated, modified or eliminated entirely, without deviating from the intended scope of the invention.

Further, these elements can be combined with elements of other technology, devices or processes now in existence or later developed without deviating from the intended scope of the invention. Similarly, any laboratory procedure, method of data collection, analysis or design of data processing programs, now known or later developed, which may be adapted to implement the instant invention, is intended to be within the scope of the instant invention.

The above examples are intended to be illustrative and not limiting in nature. Any of the elements disclosed herein may be combined with other techniques, elements, technology, processes and devices now known or later developed and such combinations and adaptations are considered to be within the scope of the instant invention. Any of the technology, elements, methods and processes described herein may be utilized in any combination.

The contents of the disclosure of this patent document is copyright to the inventor and/or assisting practitioner. The copyright owner has no objection to the facsimile reproduction of the patent document or the patent disclosure, as it appears as issued by the Patent and Trademark Office, to the extent permitted by law. Written permission of the copyright holder must be obtained for any other use. Copyright holder otherwise reserves all copyright rights whatsoever, including the right to excerpt, compile or otherwise alter or adapt, or make any other use of, this information.

In any event, any publication of or about any of the information contained herein must contain appropriate patent, trademark and copyright notices.

It will thus be seen that the objects set forth above, among those made apparent from the preceding description, are efficiently attained and certain changes may be made in carrying out the above method and in the construction set forth. Accordingly, it is intended that all matter contained in the above description or shown in the accompanying figures shall be interpreted as illustrative and not in a limiting sense.

Examples of Contemplated Uses of the Claimed Invention Include:

The use of a population of DNA fragments which are either known a-priori or which can be determined post-facto to which protein binding may be determined using other established methods for detecting the presence of protein, and the use of this information to screen for sequences which are bound by such proteins, and to determine which proteins bind to which sequences. In cases when a protein binds to more than one unique sequence comparison of the sequence data can be used to determine specificity of binding for particular portions of the sequence.

The use of the DNA sequence data obtained above to search for this region in DNA which may be in vitro or in DNA-containing organisms or material using biochemical means such as PCR amplification techniques or database search techniques in order to find the sequences and optionally to find what other DNA (typically genes) which may be in proximity to such sequences. In addition, with this information, proximal genes which may be candidates for regulation (suppression, promotion or enhancement) by such proteins may be located.

The use of in-vivo or in-vitro expression data determined using microarrays or other post-transcriptional assays to focus candidate genes enhanced or repressed by such proteins.

The use of the mapping between proteins and DNA binding sequences to determine proteins that may compete directly or indirectly for binding to a given sequence because they can bind to a sub-sequence of the given sequence, can bind to an overlapping sequence, or can bind to a neighboring sequence on the DNA such that there is some other reaction between proteins binding to such sequences.

The use of mapping information between proteins and DNA binding sequences combined with the location of these sequences in genomic DNA to determine potential proximal binding sites and potential co-regulatory proteins mediated by such proximal DNA sequences.

Several such experimental results may be combined to determine the larger gene expression regulatory networks based, in part, on the fact that such proteins are themselves subject to regulatory expression.

Another use is an improved method for determining protein bindings, wherein protein bindings are determined by otherwise standard methods for detecting the presence of protein, but improved by: the use of a population of DNA fragments, the composition of which may be known a-priori or determined post facto. The information derived from the method of above may be utilized to screen for sequences that are bound by such proteins. This sequence and protein identity information can be used to determine which proteins bind to which sequences. In one aspect, the method can be used where a protein binds to more than one unique sequence; and comparison of the sequence data is used to determine the specificity of binding for at least one particular portion of the sequence.

The DNA sequence data obtained may be utilized to search for said at least one particular portion in DNA material in order to find said sequences or to find other DNA sequences, typically genes, in proximity to such sequences, whether the search is done in vitro, or the DNA material is in a DNA-containing organism. DNA material may be in material obtained by utilizing biochemical means such as PCR amplification techniques. The DNA material may be a mathematical representation of a DNA sequence in a database, and said search is a performed by any database search technique. This information may be utilized to locate proximal genes that are candidates for regulation by such proteins, for example suppression, promotion, or enhancement.

Another use is a method whereby in-vivo or in-vitro expression data determined by the utilization of microarrays or other post-transcriptional assays to focus candidate genes enhanced or repressed by such proteins.

Another use is a method to determine proteins that potentially compete, either directly or indirectly, for binding to a given sequence through the use of the mapping between proteins and DNA binding sequences, wherein said determination is based on a finding that said DNA binding sequences bind to a sub-sequence of the given sequence.

Another use is a method to determine proteins that potentially compete, either directly or indirectly, for binding to a given sequence through the use of the mapping between proteins and DNA binding sequences, wherein said determination is based on a finding that said DNA binding sequences bind to an overlapping sequence.

Another use is a method to determine proteins that potentially compete, either directly or indirectly, for binding to a given sequence through the use of the mapping between proteins and DNA binding sequences, wherein said determination is based on a finding that said DNA binding sequences bind to a neighboring sequence on the DNA such that there is some other reaction between proteins binding to such sequences.

Another use is a method to determine potential proximal binding sites and potential co-regulatory proteins mediated by such proximal DNA sequences by the utilization in combination of: mapping information between proteins and DNA binding sequences; and, location information for these sequences in genomic DNA, and a method to determine larger gene expression regulatory networks based, at least in part, on knowledge that such proteins are themselves subject to regulatory expression; and combination of several experimental results obtained.

REFERENCES

The following are incorporated by reference unless otherwise indicated.

Books:

Benjamin Lewin, Genes VII, Oxford University Press and Cell Press, 2000

Carl Branden and John Tooze, Introduction to Protein Structure, $2^{nd}$ Edition, Garland Publishing, 1999

Mark Ptashne, A Genetic Switch, $2^{nd}$ Edition, Cell Press and Blackwell Scientific, 1992

David S. Latchman, Eukaryotic Transcription Factors, 3$^{rd}$ Edition, Academic Press, 1998

Luke Alphey, DNA Sequencing, Bios Scientific Publishers and Springer-Verlag (1997)

Michael Carey and Stephen T. Smale, Transcriptional Regulation in Eukaryotes: Concepts, Strategies, and Techniques, Cold Spring Harbor Laboratory Press, 2000

Greg T. Hermanson, A. Krishna Mallia and Paul K Smith, Immobilized Affinity Ligand Techniques, Academic Press, 1992

Current protocols in molecular biology, Frederick M. Ausubel et al. eds. Wiley-Interscience (1987)

Short protocols in molecular biology, 4$^{th}$ Edition, Frederick M. Ausubel et al. eds. John Wiley & Sons (1999)

Joseph Sambrook and David Russell, Molecular Cloning, a laboratory manual, 3$^{rd}$ Edition, Cold Spring Harbor Laboratory Press, 2001 (hererin "Sambrook 2001")

Microarray Biochip Technology, Mark Schena, Ed., Eaton Publishing (2000)

Scott F. Gilbert, Developmental Biology, 5$^{th}$ Edition. Sunderland: Sinauer Associates, 1997

E. Harlow et al., Using Antibodies: A Laboratory Manual, Cold Spring Harbor Laboratory Press, (1999).

Stryer, Biochemistry, Fourth Ed., (1995)

Oligonucleotide Synthesis: A Practical Approach, Gait, ed., IRL Press, Oxford (1984)

Protecting groups used herein can be any of those groups described in: Greene, et al., Protective Groups In Organic Chemistry, 2nd Ed., John Wiley & Sons, New York, N.Y., 1991

Antibody assays are described in:

L. Hood et al., Immunology, Benjamin/Cummings (1978), and E. Harlow et al., Antibodies. A Laboratory Manual, Cold Spring Harbor Laboratory, (1988).

PAPERS

Microarray papers:

Fodor S. P. A. et al. (1991) Light-Directed Spatially Addressable Parallel Chemical Synthesis. *Science* 251: 767-773.

Pease A. C. et al. (1994) Light-generated oligonucleotide arrays for rapid DNA sequence analysis. *PNAS* 91: 5022-5026.

Shalon D, Smith S J, Brown P O. (1996) A DNA microarray system for analyzing complex DNA samples using two-color fluorescent probe hybridization. *Genome Res.* 6: 639-45.

Schena M, Shalon D, Davis R W, Brown P O. (1995) Quantitative monitoring of gene expression patterns with a complementary DNA microarray. *Science* 270: 467-70.

dsDNA Arrays

Bulyk, M. et al. (1999) Quantifying DNA-protein interactions by double-stranded DNA arrays. *Nature Biotechnology* 17: 573-577.

ss BEAD Assays

Brenner S. et al. (2000) In vitro cloning of complex mixtures of DNA on microbeads: Physical separation of differentially expressed cDNAs. *PNAS* 97:1665-1670.

Brenner S. et al. (2000) Gene expression analysis by massively parallel signature sequencing (MPSS) on microbead arrays. *Nature Biotechnology* 18: 630-634.

Needels, M. C. et al. (1993) Generation and Screening of an Oligonucleotide-Encoded Synthetic Peptide Library. *PNAS* 90: 10700-10704.

Beads w/transcription factor sites paper:

Molina, D. et al, DNA-bound transcription factor complexes may be analysed by mass-spectrometry: binding of novel proteins to the human c-fos SRE and related sequences. *Nucleic Acids Research* 29: 479-487, 2001.

Sequencing:

Maxam, A. M., and Gilbert, W. (1977) A new method for sequencing DNA. *PNAS* 74:560-564.

Maxam, A. M., and Gilbert, W. (1980) Sequencing end-labelled DNA with base-specific cleavages. *Methods in Enzymology* 65: 499-560.

Sanger, F., Nicklen, S. and Coulson, A. R. (1977) DNA sequencing with chain-terminating inhibitors. *PNAS* 74: 5463-5467.

Eukaryotic Gene Regulation:

Rossi, F. M. V. et al. (2000) Transcriptional Control: Rheostat Converted to On/Off Switch. *Molecular Cell* 6:723-728

Arnone, M. and Davidson, E. (1997) The hardwiring of development: organization and function of genomic regulatory systems. *Development* 124: 1851-1864

Oligonucleotides may be prepared by methods described by:

Durand, et al. Nucleic Acids Res. 18:6353-6359 (1990)

Thomson, et al. Nucleic Acids Res. 21:5600-5603 (1993)

Beaucage and Carruthers, Tetrahedron Lett., 22:1859-1862 (1981)

Matteucci, et al., J. Am. Chem. Soc., 103:3185 (1981)

Footprint analysis using Gels:

Galas et al., Nucleic Acid Res. 5:3157 (1978).

Misc:

Schuldiner O, Yanover C, Benvenisty N. (1998) Computer analysis of the entire budding yeast genome for putative targets of the GCN4 transcription factor. *Curr Genet* 33:16-20.

Dervan, P. B. and Burli, R. W. (1999) Sequence-specific DNA recognition by polyamides, *Current Opinion in Chemical Biology* 3:688-693.

Schevchenko, A. et al. (1996) Mass Spectrometric Sequencing of Proteins from Silver-Stained Polyacrylamide Gels. *Anal. Chem.* 68: 850-858

Special Issue on (strept)avidin-biotin (1999) *Biomolecular Engineering* volume 16

Patents:

Surface-bound unimolecular, double-stranded DNA: U.S. Pat. No. 5,556,752 Lockhart, et al. Sep. 17, 1996

Large Scale Photolithographic solid phase synthesis of polypeptides and receptor binding screening thereof: U.S. Pat. No. 5,143,854 Pirrung, et al. Sep. 1, 1992

Massively Parallel Signature Sequencing by Ligation of Encoded Adapters: U.S. Pat. No.: 6,013,445, Albrecht et al., Jan. 11, 2000

Methods for Sorting Polynucleotides Using Oligonucleotide Tags: U.S. Pat. No. 5,604,097, Brenner, Feb 18, 1997

Oligonucleotide Tags for Sorting and Identification: U.S. Pat. No. 5,846,719, Brenner et al., Dec. 8, 1998

APPENDIX I

```perl
#!/usr/bin/perl

###############################################################
# Copyright (c) 2002 Michael F Chou - All rights reserved
###############################################################
# This program written in Perl, first generates simulated binding
# site data (i.e Gross Binding Site Output) for a given binding
# site by a DNA-binding protein whose sequence is given by the
# truesite variable set immediately below.
###############################################################

$truesite = "gatt";

###############################################################
# The program then perfoms the algorithm described in the
# application known as Algorithm 1. See comment below indicating
# the true start of alrgorithm 1, which would, in fact use real
# experimental data from dsDNA-protein binding assays.

# The final output of the program, correctly identifies the
# truesite used to generate the data, and shows the 'truesite'
# and its reverse complement which would be found on any probes
# with the reverse complement sequence.
###############################################################

# Generate the sequence of all possible probes of length N.
in the following case, N is 6, but could be any practical length @aaa = ("a", "c", "g", "t");

@searchlist = (@aaa);
        @tempprod = cartprod (\@aaa, \@aaa);
        push(@searchlist, @tempprod);
        @prod = @tempprod;

@tempprod = cartprod (\@prod, \@aaa);
        push(@searchlist, @tempprod);
        @prod = @tempprod;

@tempprod = cartprod (\@prod, \@aaa);
        push(@searchlist, @tempprod);
        @prod = @tempprod;

@tempprod = cartprod (\@prod, \@aaa);
        push(@searchlist, @tempprod);
        @prod = @tempprod;

@tempprod = cartprod (\@prod, \@aaa);
        push(@searchlist, @tempprod);
        @prod = @tempprod;

# The array @prod now contains sequences of length N, and
# the array @searchlist contains all sequences of length N or
# fewer bases.
```

```
################################################################
# Following is a simulated binding site assay experiment
# of all probes of length N being exposed to the TF that
# recognizes the site in 'truesite':
################################################################

$c = 0;

foreach $z (@prod) {
                my($zz) = "$z - " . revcom($z);
                if ($z eq revcom($z)) {
                        $c++;
                        }
                $z = $zz;
                }

$l = length("$#prod");

foreach $i (0..$#prod) {
                $l2 = length("$i");
                $i2 = " " x ($l - $l2) . "$i";
                } print "\nOut of " . scalar(@prod) .
                " probes, $c Palindromes were found\n\n";

@expdata = ();

foreach $x (@prod) {
                if ($x =~ /$truesite/) {
                        push (@expdata, $x);
                        }
                } print "Simulation Results:\n\n";
        print "The site '$truesite' matches to " .
                scalar(@expdata) . " sites out of " .
                scalar(@prod) . " probes\n\n";

print "Following is Simulated Gross Binding SiteData for\n";
        print "a protein that binds to sequence '$truesite'.\n\t";
        print "forward - reverse\n\n\t";
        print join ("\n\t", @expdata) . "\n";

################################################################
# This is the end of the simulated Binding Experiment, and
# the array @expdata now contains the equivalent of
# the Gross Binding Site Data described in the application
# Following, now is the algorithm described in the
# application.
########################################################## print "\n\nBased upon the Algorithm to determine Binding
Sites\n";
        print "from Gross Binding Site Data, following is a list of\n";
        print "all matching sites:\n\t";
```

```
        @matching = determine_site(\@prod, \@searchlist);

# This is the list of all possible site <= length N
        # which is consistent with the experimental data print join ("\n\t", sort @matching);
        print "\n\n";

PRUNE THE BINDING SITE DATA TO ELIMINATE REDUNDANCY

@matching = prune(@matching);

print "After Pruning, here is the focused list of binding
sites:\n";
        print "All matching sites:\n\t";
        print join ("\n\t", sort @matching);
        print "\n";

exit;

###################################################################
# End of Main Program
###################################################################

###################################################################
# Begining of support routines
###################################################################
# simulates binding to each of the probes in the set, and tests
# if the simulated binding data is consistent with the actual
# bound data set by testing if the set of probes simulated to
# bind is a subset of the actual set of bound probes
###################################################################
sub determine_site {
        my ($a, $b) = @_;
        my (@prod) = @$a;
        my (@searchlist) = @$b;
        my (@matching) = ();

foreach $s (@searchlist) {
                my (@putative) = ();

foreach $x (@prod) {
                        if ($x =~ /$s/) {
                                push (@putative, $x);
                                }
                        } if (scalar(@putative) > 0 and
                    subset(\@putative, \@expdata) == 1) {

# Pattern $s agrees with the experimental data
                        push (@matching, $s);
                        }
                }
```

```perl
        return (@matching);
}

################################################################
# Prune the matching data set to remove redundant superstrings
################################################################
sub prune {
        my (@list) = @_;
        my (%remaining) = ();

foreach $e (@list) {
                $remaining{$e}++;
                } foreach $e (@list) {
                foreach $r (keys %remaining) {
                        if ($r ne $e and $r =~ /$e/) {
                                delete $remaining{$r};
                                }
                        }
                } return (sort keys %remaining);
}

################################################################
# Test if (Set A contined in Set B)
################################################################
sub subset {
        my ($list1, $list2) = @_;
        my (@lista) = @$list1;
        my (@listb) = @$list2;
        my ($x) = ();
        my (%b) = ();

foreach $x (@listb) {
                $b{$x}++;
                } foreach $x (sort @lista) {
                if (!exists $b{$x}) { return 0; }
                }

1;
}

################################################################
# Perform a cartesian product between two sequences to produce a
# third
################################################################
sub cartprod {
        my ($list1, $list2) = @_;
        my (@lista) = @$list1;
```

```perl
        my (@listb) = @$list2;
        my (@listc) = ();
        my ($x, $y) = ();

foreach $x (@lista) {
                foreach $y (@listb) {
                        push(@listc, "$x$y");
#                       print "$x$y\n";
                        }
                }
        @listc;
}

################################################################
# generate the reverse complement sequence
################################################################
sub revcom {
        my ($watson) = @_;
        my $crick = '';
        my $len = 0;

$len = length($watson);

for ($i=($len-1); $i>=0; $i--) {
            $crick .= substr($watson, $i, 1);
            }

$crick =~ tr/ATGC/atgc/;
        $crick =~ tr/atgc/tacg/;

return ($crick);
}

################################################################
# generate the reverse string
################################################################
sub revstr {
        my ($watson) = @_;
        my $crick = '';
        my $len = 0;

$len = length($watson);

for ($i=($len-1); $i>=0; $i--) {
            $crick .= substr($watson, $i, 1);
            } return ($crick);
}
```

Following is a sample output from an execution of the program:

Out of 4096 probes, 64 Palindromes were found

Simulation Results:

The site 'gatt' matches to 96 sites out of 4096 probes

Following is Simulated Gross Binding SiteData for
a protein that binds to sequence 'gatt'.
```
      forward - reverse aaaatc - gatttt
    aaatca - tgattt
    aaatcc - ggattt
    aaatcg - cgattt
    aaatct - agattt
    aagatt - aatctt
    aatcaa - ttgatt
    aatcac - gtgatt
    aatcag - ctgatt
    aatcat - atgatt
    aatcca - tggatt
    aatccc - gggatt
    aatccg - cggatt
    aatcct - aggatt
    aatcga - tcgatt
    aatcgc - gcgatt
    aatcgg - ccgatt
    aatcgt - acgatt
    aatcta - tagatt
    aatctc - gagatt
    aatctg - cagatt
    aatctt - aagatt
    acaatc - gattgt
    acgatt - aatcgt
    agaatc - gattct
    agatta - taatct
    agattc - gaatct
    agattg - caatct
    agattt - aaatct
    aggatt - aatcct
    ataatc - gattat
    atgatt - aatcat
    caaatc - gatttg
    caatca - tgattg
    caatcc - ggattg
    caatcg - cgattg
    caatct - agattg
    cagatt - aatctg
    ccaatc - gattgg
    ccgatt - aatcgg
    cgaatc - gattcg
    cgatta - taatcg
    cgattc - gaatcg
    cgattg - caatcg
```

```
cgattt - aaatcg
cggatt - aatccg
ctaatc - gattag
ctgatt - aatcag
gaaatc - gatttc
gaatca - tgattc
gaatcc - ggattc
gaatcg - cgattc
gaatct - agattc
gagatt - aatctc
gattaa - ttaatc
gattac - gtaatc
gattag - ctaatc
gattat - ataatc
gattca - tgaatc
gattcc - ggaatc
gattcg - cgaatc
gattct - agaatc
gattga - tcaatc
gattgc - gcaatc
gattgg - ccaatc
gattgt - acaatc
gattta - taaatc
gatttc - gaaatc
gatttg - caaatc
gatttt - aaaatc
gcaatc - gattgc
gcgatt - aatcgc
ggaatc - gattcc
ggatta - taatcc
ggattc - gaatcc
ggattg - caatcc
ggattt - aaatcc
gggatt - aatccc
gtaatc - gattac
gtgatt - aatcac
taaatc - gattta
taatca - tgatta
taatcc - ggatta
taatcg - cgatta
taatct - agatta
tagatt - aatcta
tcaatc - gattga
tcgatt - aatcga
tgaatc - gattca
tgatta - taatca
tgattc - gaatca
tgattg - caatca
tgattt - aaatca
tggatt - aatcca
ttaatc - gattaa
ttgatt - aatcaa
```

Based upon the Algorithm to determine Binding Sites from Gross Binding Site Data, following is a list of all matching sites:

aaaatc
aaatc
aaatca
aaatcc
aaatcg
aaatct
aagatt
aatc
aatca
aatcaa
aatcac
aatcag
aatcat
aatcc
aatcca
aatccc
aatccg
aatcct
aatcg
aatcga
aatcgc
aatcgg
aatcgt
aatct
aatcta
aatctc
aatctg
aatctt
acaatc
acgatt
agaatc
agatt
agatta
agattc
agattg
agattt
aggatt
ataatc
atgatt
caaatc
caatc
caatca
caatcc
caatcg
caatct
cagatt
ccaatc
ccgatt
cgaatc
cgatt
cgatta
cgattc
cgattg
cgattt
cggatt
ctaatc
ctgatt gaaatc
gaatc
gaatca
gaatcc
gaatcg
gaatct
gagatt
gatt
gatta
gattaa
gattac
gattag
gattat
gattc
gattca
gattcc
gattcg
gattct
gattg
gattga
gattgc
gattgg
gattgt
gattt
gattta
gatttc
gatttg
gatttt
gcaatc
gcgatt
ggaatc
ggatt
ggatta
ggattc
ggattg
ggattt
gggatt
gtaatc
gtgatt
taaatc
taatc
taatca
taatcc
taatcg
taatct
tagatt
tcaatc
tcgatt
tgaatc
tgatt
tgatta
tgattc
tgattg
tgattt
tggatt
ttaatc
ttgatt After Pruning, here is the focused list of binding sites:
All matching sites:
    aatc
    gatt

What is claimed is:

1. A method for determining the nucleic acid subsequence specificity of at least one putative double-stranded DNA-binding protein, which comprises:

(a) providing a plurality of double-stranded nucleic acid probes which represent substantially all combinations of sequences of length N in solution or immobilized on a solid support, wherein N is at least three and substantially all combinations of sequences of length N is $4^N$ different sequences;

(b) contacting said double-stranded nucleic acid probes with said at least one putative double-stranded DNA-binding protein under conditions in which DNA-binding proteins bind to double-stranded nucleic acid;

(c) determining whether said at least one putative double-stranded DNA-binding protein has bound to a double-stranded nucleic acid sequence, thus determining if said at least one putative double-stranded DNA-binding protein is a double-stranded DNA-binding protein;

(d) determining gross binding site data, wherein said gross binding site data comprises nucleic acid sequences of substantially all double-stranded nucleic acid probes, wherein said nucleic acid sequences comprise nucleic acid sequences of bound probes and unbound probes; and (e) using said gross binding site data to determine the subsequences common to the double-stranded nucleic acid probes to which said DNA-binding protein has bound in step (b); thus determining the nucleic acid subsequence specificity of the at least one DNA-binding protein.

2. A method of claim 1 wherein the solid support is an array.

3. A method of claim 1 wherein the solid support is beads.

4. A method of claim 1 wherein N is a number from three through ten.

5. A method of claim 1 wherein N is a number from eleven through sixteen.

6. A method of claim 1 wherein N is a number from sixteen through twenty-five.

7. A method of claim 1 wherein, as part of step (a), the double-stranded nucleic acid binding probes are prescreened to remove those probes which are known not to bind to the DNA-binding protein whose specificity is to be determined.

8. A method of claim 1 wherein the double-stranded nucleic acid probes are attached to the solid support by a double-stranded nucleic acid linker which are known to lack any binding site for the DNA-binding protein whose specificity is to be determined.

9. A method of claim 1 wherein the double-stranded nucleic acid probes are attached to the solid support a by double-stranded nucleic acid linker whose sequence is known and can therefore be discounted if bound by a DNA binding protein.

10. A method of claim 1 wherein N is selected to be longer than the expected length of the binding site of the DNA-binding protein whose specificity is to be determined.

11. A method of claim 10 also comprising step (f) in which the nucleic acid sequence specificity of the DNA-binding protein which has bound to a set of probes longer than its natural binding site is determined to provide the sequence of the natural binding site.

12. A method for determining whether two double-stranded DNA-binding proteins bind to the same binding sites which comprises the process of applying the method of claim 1 to each of two proteins and, in addition:
(a) narrowing the binding sites for each protein by analysis of the probe sequences; and,
(b) determining whether the two proteins bind to the same binding site by determining whether the two proteins have bound to the same subsequences of any bound probes.

13. A method employing two instances of the method of claim 1 to determine the binding of DNA-binding proteins to double-stranded DNA binding site sequences, and in addition two instances of mRNA expression analysis, resulting in a determination of a correspondence between the expression levels of genes and binding of DNA-binding proteins to double-stranded binding site sequences, which method comprises the steps of:
(a) running essentially simultaneously from portions of the same first sample a first mRNA expression analysis and a first double-stranded DNA binding analysis of claim 1;
(b) running essentially simultaneously from portions of the same second sample a second mRNA expression analysis and a second double-stranded DNA binding analysis of claim 1;
(c) comparing the change in results between said first mRNA analyses and said second mRNA analyses to identify a set G of genes which have changed in their expression level; and,
(d) comparing the change in results between said first double-stranded DNA analyses of claim 1 and said second double-stranded DNA analyses of claim 1 to identify a set B of binding sites which have changed in their level of binding.

14. A process of claim 13 for determining a correspondence between the expression levels of genes and potential genomic binding sites, further comprising:
(e) searching, in the promoter regions of each of the genes in set G, for each of the binding sites in set B, in order to create a mapping BG from individual binding sites in B and individual genes in G.

15. A process of claim 14 for determining a correspondence between transcription factor proteins and genomic binding sites, further comprising:
(f) data, comprising a correspondence between a set of transcription factors T and their binding sites, is consulted to create a mapping TB from individual transcription factor proteins and individual genomic binding sites; and,
(g) combining, via common set B, map TB and map BG to create map TG of potential transcription factors responsible for control of gene expression.

16. A process of claim 15, wherein said data of step (f) is derived by assaying at least one purified protein using at least one library of double-stranded DNA probes.

17. A process of claim 16, wherein at least one of said at least one library comprises substantially all possible sequences of double-stranded DNA probes of length N.

18. A method employing one instance of the method of claim 1 to determine the binding of DNA-binding proteins to double-stranded DNA binding site sequences, and in addition one instance of mRNA expression analysis, resulting in a determination of sequences containing the sequences of promoters of genes activated in a cell at a moment in time, which method comprises:
(a) contacting total mRNA isolated from said cell at said moment in time with a plurality of single-stranded total genomic nucleic acid probes in solution or in an immobilized state on a solid support and determining from analysis of said plurality which genes of the cell are being expressed;
(b) contacting the total protein population isolated from said cell at said moment in time with a plurality of double-stranded nucleic acid probes, as by the method of claim 1, which represent substantially all combinations of sequences of length N in solution or in an immobilized state on a solid support and determining from analysis of said plurality the double-stranded nucleic acid probes which have been bound by a DNA-binding protein from the total protein population of the cell; and,
(c) determining the nucleic acid sequences of the bound double-stranded nucleic acid probes, as determined by the method of claim 1, and thereby obtaining sequences containing the sequences of promoters activated in a cell at said moment in time.

19. A method employing two instances of the method of claim 1 to determine the binding of DNA-binding proteins to double-stranded DNA binding site sequences, and in addition two instances of mRNA expression analysis, resulting in a comparison between the gene activation in a first cell and the gene activation in a second cell, which method comprises:
(a) contacting total mRNA isolated from a first cell with a plurality of single-stranded total genomic nucleic acid probes in solution or in an immobilized state on a solid support and determining from analysis of said plurality which genes of the cell are being expressed and contacting total mRNA isolated from a second cell with a plurality of single-stranded total genomic nucleic acid probes in solution or in an immobilized state on a solid support and determining from analysis of said plurality which genes of the cell are being expressed;
(b) contacting the total protein population isolated said first cell with a plurality of double-stranded nucleic acid probes which represent substantially all combinations of sequences of length N in solution or in an immobilized state on a solid support and determining from analysis, as by the method of claim 1, of said plurality the double-stranded nucleic acid probes which have been bound by a DNA-binding protein from the total protein population of said first cell; and contacting the total protein population isolated from said second cell with a plurality of double-stranded nucleic acid probes which represent substantially all combinations of sequences of length N in solution or in an immobilized state on a solid support and determining from analysis, as by the method of claim 1, of said plurality the double-stranded nucleic acid probes which have been bound by a DNA-binding protein from the total protein population of said second cell;

(c) determining the nucleic acid sequences of the bound double-stranded nucleic acid probes for said first cell, as by the method of claim 1, and thereby obtaining sequences containing the sequences of promoters activated in said first cell and determining the nucleic acid sequences of the bound double-stranded nucleic acid probes for said second cell, as by the method of claim 1, and thereby obtaining sequences containing the sequences of promoters activated in said second cell; and, (d) comparing the sequences obtained for said first cell with the sequences obtained for said second cell to determine gene activation in the first cell and in the second cell.

20. A method as in claim 1 wherein said at least one protein is at least one transcription factor and step (b) is performed under conditions such that said transcription factor binds to a specific double-stranded nucleic acid sequence of the plurality of double-stranded nucleic acid probes provided in step (a).

21. A method of claim 20 wherein the double-stranded nucleic acid probes represent all possible four base pair sequence to all possible eight base pair sequences.

22. The method of claim 1, wherein said gross binding site data is determined using iterative sanger sequencing.

* * * * *